US012691146B2

(12) United States Patent　　　　(10) Patent No.: US 12,691,146 B2
Bonifant et al.　　　　　　　　　(45) Date of Patent: Jul. 28, 2026

(54) ENGINEERED IMMUNE CELLS TO TARGET SARS-CoV2

(71) Applicant: The Johns Hopkins University, Baltimore, MD (US)

(72) Inventors: Challice Bonifant, Baltimore, MD (US); Ilias Christodoulou, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 609 days.

(21) Appl. No.: 18/029,592

(22) PCT Filed: Sep. 30, 2021

(86) PCT No.: PCT/US2021/053042
§ 371 (c)(1),
(2) Date: Mar. 30, 2023

(87) PCT Pub. No.: WO2022/072748
PCT Pub. Date: Apr. 7, 2022

(65) Prior Publication Data
US 2025/0268937 A1　　　Aug. 28, 2025

Related U.S. Application Data

(60) Provisional application No. 63/085,937, filed on Sep. 30, 2020.

(51) Int. Cl.
| *A61K 40/31* | (2025.01) |
| *A61K 35/17* | (2015.01) |
| *A61K 40/11* | (2025.01) |
| *A61K 40/15* | (2025.01) |
| *A61K 40/48* | (2025.01) |
(Continued)

(52) U.S. Cl.
CPC .............. *A61K 35/17* (2013.01); *A61K 40/11* (2025.01); *A61K 40/15* (2025.01); *A61K 40/31* (2025.01); *A61K 40/48* (2025.01); *A61K 47/6803* (2017.08); *A61P 31/14* (2018.01); *A61P 35/00* (2018.01); *C07K 16/16* (2013.01); *A61K 2239/13* (2023.05)

(58) Field of Classification Search
None
See application file for complete search history.

(56) References Cited

U.S. PATENT DOCUMENTS

| 5,034,506 A | 7/1991 | Summerton et al. |
| 5,235,033 A | 8/1993 | Summerton et al. |
| (Continued) |

FOREIGN PATENT DOCUMENTS

| EP | 45665 A1 | 2/1982 |

OTHER PUBLICATIONS

André S, et al. Lectins: getting familiar with translators of the sugar code. Molecules. 2015, 1788-823, 20(2).
(Continued)

*Primary Examiner* — Daniel C Gamett
(74) *Attorney, Agent, or Firm* — Lisa Mueller; Casimir Jones SC

(57) ABSTRACT

Provided herein are, inter *alia*, methods, compositions and kits for treating or preventing coronaviruses, e.g., SARS-CoV-2. Also included herein are kits for treating or preventing coronaviruses, e.g., SARS-CoV-2.

17 Claims, 11 Drawing Sheets

Specification includes a Sequence Listing.

SARS-COV2

Chimeric Antigen Receptor

NK Cell

Infected cell displaying viral envelope proteins

(51) Int. Cl.

| | |
|---|---|
| *A61K 47/68* | (2017.01) |
| *A61P 31/14* | (2006.01) |
| *A61P 35/00* | (2006.01) |
| *C07K 16/16* | (2006.01) |

(56) References Cited

U.S. PATENT DOCUMENTS

| | | | |
|---|---|---|---|
| 9,481,717 B2 | 11/2016 | Markovitz et al. | |
| 9,834,753 B2 | 12/2017 | Min et al. | |
| 2020/0247868 A1 | 8/2020 | Bonifant et al. | |
| 2021/0369811 A1* | 12/2021 | Manyak | C12Q 1/6883 |

OTHER PUBLICATIONS

Gabius HJ et al. From lectin structure to functional glycomics: principles of the sugar code. Trends in biochemical sciences. 2011, 298-313, 36(6).

Smith TF, Waterman MS. Comparison of biosequences. Advances in applied mathematics. 1981, 482-9, 2(4).

Needleman SB, Wunsch CD. A general method applicable to the search for similarities in the amino acid sequence of two proteins. Journal of molecular biology. 1970, 443-53, 48(3).

Pearson WR, Lipman DJ. Improved tools for biological sequence comparison. Proceedings of the National Academy of Sciences. 1988, 2444-8, 85(8).

Altschul SF, et al. Gapped BLAST and PSI-BLAST: a new generation of protein database search programs. Nucleic acids research. 1997, 3389-402, 25(17).

Altschul SF, et al. Basic local alignment search tool. Journal of molecular biology. 1990, 403-10, 215(3).

Henikoff S, Henikoff JG. Amino acid substitution matrices from protein blocks. Proceedings of the National Academy of Sciences. 1992, 10915-9, 89(22).

Weinstein MI. Existence and dynamic stability of solitary wave solutions of equations arising in long wave propagation. Communication in Partial Differential Equation. 1987, 1133-73, 12(10).

Hudson D et al. Methionine enkephalin and isosteric analogues I. Synthesis on a phenolic resin support. International Journal of Peptide and Protein Research. 1979, 177-85, 14(3).

Morley JS. Modulation of the action of regulatory peptides by structural modification. Trends in Pharmacological Sciences. 1980, 463-8, 1(2).

Spatola AF et al. Structure-activity relationships of enkephalins containing serially replaced thiomethylene amide bond surrogates. Life Sciences. 1986, 1243-9, 38(14).

Hann MM, et al. On the double bond isostere of the peptide bond: preparation of an enkephalin analogue. Journal of the Chemical Society, Perkin Transactions 1. 1982, 307-14.

Jennings-White C, Almquist RG. Synthesis of ketomethylene analogs of dipeptides. Tetrahedron Letters. 1982, 2533-4, 23(25).

Holladay MW, Rich DH. Synthesis of hydroxyethylene and ketomethylene dipeptide isosteres. Tetrahedron Letters. 1983, 4401-4, 24(41).

Hruby VJ. Conformational restrictions of biologically active peptides via amino acid side chain groups. Life sciences. 1982, 189-99, 31(3).

Koshte VL, et al. Isolation and characterization of BanLec-I, a mannoside-binding lectin from *Musa paradisiac* (banana). Biochemical journal. 1990, 721-6, 272(3).

Hopper JT, et al. The tetrameric plant lectin BanLec neutralizes HIV through bidentate binding to specific viral glycans. Structure. 2017, 773-82, 25(5).

Li W, et al. Angiotensin-converting enzyme 2 is a functional receptor for the SARS coronavirus. Nature. 2003, 450-4, 426(6965).

Wrapp D, et al. Cryo-EM structure of the 2019-nCoV spike in the prefusion conformation. Science. 2020, 1260-3, 367 (6483).

Watanabe Y, et al. Site-specific glycan analysis of the SARS-CoV-2 spike. Science. 2020, 330-3, 369(6501).

Zhang Y, et al. Site-specific N-glycosylation characterization of recombinant SARS-CoV-2 spike proteins. Molecular & Cellular Proteomics. 2021, 20.

Shajahan A, et al. Deducing the N-and O-glycosylation profile of the spike protein of novel coronavirus SARS-CoV-2. Glycobiology. 2020, 981-8, 30(12).

Covés-Datson EM, et al. A molecularly engineered antiviral banana lectin inhibits fusion and is efficacious against influenza virus infection in vivo. Proceedings of the National Academy of Sciences. 2020, 2122-32, 117(4).

Swanson MD, et al. A lectin isolated from bananas is a potent inhibitor of HIV replication. Journal of Biological Chemistry. 2010, 8646-55, 285(12).

Mitchell CA, et al. Antiviral lectins: Selective inhibitors of viral entry. Antiviral research. 2017, 37-54, 142.

Swanson MD, et al. Engineering a therapeutic lectin by uncoupling mitogenicity from antiviral activity. Cell. 2015, 746-58, 163(3).

Imai C, et al. Genetic modification of primary natural killer cells overcomes inhibitory signals and induces specific killing of leukemic cells. Blood. 2005, 376-83, 106(1).

Liu E, et al. Use of CAR-transduced natural killer cells in CD19-positive lymphoid tumors. New England Journal of Medicine. 2020, 545-53, 382(6).

Bonifant CL, et al. Toxicity and management in CAR T-cell therapy. Molecular Therapy-Oncolytics. 2016, 16011, 3.

Bonifant CL, et al. CD123-engager T cells as a novel immunotherapeutic for acute myeloid leukemia. Molecular Therapy. 2016, 1615-26, 24(9).

Krawczyk E, et al. T-cell Activity against AML Improved by Dual-Targeted T Cells Stimulated through T-cell and IL7 ReceptorsCLEC12AENG/CD123IL7Rα T Cells Exhibit Anti-AML Activity. Cancer immunology research. 2019, 683-92, 7(4).

Zolov SN, et al. Programmed cell death protein 1 activation preferentially inhibits CD28. CAR-T cells. Cytotherapy. 2018, 1259-66, 20(10).

Giamarellos-Bourboulis EJ, et al. Complex immune dysregulation in COVID-19 patients with severe respiratory failure. Cell host & microbe. 2020, 992-1000, 27(6).

Wang F, et al. Characteristics of peripheral lymphocyte subset alteration in COVID-19 pneumonia. The Journal of infectious diseases. 2020, 1762-9, 221(11).

Qin C, et al. Dysregulation of immune response in patients with coronavirus 2019 (COVID-19) in Wuhan, China. Clinical infectious diseases. 2020, 762-8, 71(15).

Siegler EL, et al. Off-the-shelf CAR-NK cells for cancer immunotherapy. Cell stem cell. 2018, 160-1, 23(2).

Steentoft C, et al. Glycan-directed CAR-T cells. Glycobiology. 2018, 656-69, 28(9).

Mohamadian M, et al. COVID-19: Virology, biology and novel laboratory diagnosis. The journal of gene medicine. 2021, e3303, 23(2).

Baden LR et al. Efficacy and safety of the mRNA-1273 SARS-CoV-2 vaccine. New England journal of medicine. 2021, 403-16, 384(5).

Polack FP, et al. Safety and efficacy of the BNT162b2 mRNA Covid-19 vaccine. New England journal of medicine. 2020, 2603-15, 383(27).

Files JK, et al. Sustained cellular immune dysregulation in individuals recovering from SARS-CoV-2 infection. The Journal of Clinical Investigation. 2021, 131(1).

Cizmecioglu A, et al. Apoptosis-induced T-cell lymphopenia is related to COVID-19 severity. Journal of medical virology. 2021, 2867-74, 93(5).

Diao B, et al. Reduction and functional exhaustion of T cells in patients with coronavirus disease 2019 (COVID-19). Frontiers in immunology. 2020,827.

Liu J, et al. Longitudinal characteristics of lymphocyte responses and cytokine profiles in the peripheral blood of SARS-CoV-2 infected patients. EBioMedicine. 2020, 102763, 55.

Wilk AJ, et al. A single-cell atlas of the peripheral immune response in patients with severe COVID-19. Nature medicine. 2020, 1070-6, 26(7).

(56) References Cited

OTHER PUBLICATIONS

Hammer Q, et al. Natural killer cell specificity for viral infections. Nature immunology. 2018, 800-8, 19(8).

Lam VC, Lanier LL. NK cells in host responses to viral infections. Current opinion in immunology. 2017, 43-51, 44.

Martinet L, Smyth MJ. Balancing natural killer cell activation through paired receptors. Nature Reviews Immunology. 2015, 243-54, 15(4).

Prager I, Watzl C. Mechanisms of natural killer cell-mediated cellular cytotoxicity. Journal of leukocyte biology. 2019, 1319-29, 105(6).

Koutsakos M, et al. Downregulation of MHC class I expression by influenza A and B viruses. Frontiers in immunology. 2019, 1158, 10.

Lodoen MB, Lanier LL. Viral modulation of NK cell immunity. Nature Reviews Microbiology. 2005, 59-69, 3(1).

Brandstadter JD, Yang Y. Natural killer cell responses to viral infection. Journal of innate immunity. 2011, 274-9, 3(3).

Ma M, et al. CAR-NK cells effectively target the D614 and G614 SARS-CoV-2-infected cells. BioRxiv. 2021, Jan. 2021.

Wei J, et al. Target selection for CAR-T therapy. Journal of hematology & oncology. 2019, 1-9,12.

Li Q, et al. The impact of mutations in SARS-CoV-2 spike on viral infectivity and antigenicity. Cell. 2020, 1284-94, 182 (5).

Barton C, et al. Pharmacokinetics of the antiviral lectin griffithsin administered by different routes indicates multiple potential uses. Viruses. 2016, 331, 8(12).

Eyquem J, et al. Targeting a CAR to the TRAC locus with CRISPR/Cas9 enhances tumour rejection. Nature. 2017, 113-7, 543(7643).

Long AH, et al. 4-1BB costimulation ameliorates T cell exhaustion induced by tonic signaling of chimeric antigen receptors. Nature medicine. 2015, 581-90, 21(6).

Gheblawi M, et al. Angiotensin-converting enzyme 2: SARS-CoV-2 receptor and regulator of the renin-angiotensin system: celebrating the 20th anniversary of the discovery of ACE2. Circulation research. 2020, 1456-74, 126(10).

Crawford KH, et al. Protocol and reagents for pseudotyping lentiviral particles with SARS-CoV-2 spike protein for neutralization assays. Viruses. 2020, 513, 12(5).

Biron CA, et al. Natural killer cells in antiviral defense: function and regulation by innate cytokines. Annual review of immunology. 1999, 189-220, 17(1).

Orange JS, et al. Viral evasion of natural killer cells. Nature immunology. 2002, 1006-12, 3(11).

Taefehshokr N, et al. Covid-19: perspectives on innate immune evasion. Frontiers in immunology. 2020, 580641,11.

Xu Y, et al. 2B4 costimulatory domain enhancing cytotoxic ability of anti-CD5 chimeric antigen receptor engineered natural killer cells against T cell malignancies. Journal of hematology & oncology. 2019, 1-3,12.

Shimasaki N, et al. A clinically adaptable method to enhance the cytotoxicity of natural killer cells against B-cell malignancies. Cytotherapy. 2012, 830-40, 14(7).

Chu Y, et al. Targeting CD20+ aggressive B-cell non-Hodgkin lymphoma by anti-CD20 CAR mRNA-modified expanded natural killer cells in vitro and in NSG mice. Cancer immunology research. 2015, 333-44,3(4).

Zheng M, et al. Functional exhaustion of antiviral lymphocytes in COVID-19 patients. Cellular & molecular immunology. 2020, 533-5, 17(5).

Ciurea SO, et al. Phase 1 clinical trial using mbIL21 ex vivo-expanded donor-derived NK cells after haploidentical transplantation. Blood, The Journal of the American Society of Hematology. 2017 , 1857-68, 130(16).

Vera J, et al. T lymphocytes redirected against the k light chain of human immunoglobulin efficiently kill mature B lymphocyte-derived malignant cells. Blood. 2006, 3890-7, 108(12).

Büeler H, Mulligan RC. Induction of antigen-specific tumor immunity by genetic and cellular vaccines against MAGE: enhanced tumor protection by coexpression of granulocyte-macrophage colony-stimulating factor and B7-1. Molecular Medicine. 1996, 545-55, 2(5).

Kunz A, et al. Optimized assessment of qPCR-based vector copy numbers as a safety parameter for GMP-grade Car T cells and monitoring of frequency in patients. Molecular Therapy-Methods & Clinical Development. 2020, 448-54, 17.

Murphy GJ, et al. Exogenous control of mammalian gene expression via modulation of translational termination. Nature medicine. 2006, 1093-9, 12(9).

Procko E. The sequence of human ACE2 is suboptimal for binding the S spike protein of SARS coronavirus 2. BioRxiv. 2020.

Fujisaki H, et al. Expansion of highly cytotoxic human natural killer cells for cancer cell therapy. Cancer research. 2009, 4010-7, 69(9).

Bonifant CL, Tasian SK. The future of cellular immunotherapy for childhood leukemia. Current opinion in pediatrics. 2020, 13, 32(1).

Golchin A, et al. Mesenchymal stem cell therapy for COVID-19: present or future. Stem cell reviews and reports. 2020, 427-33, 16.

Shi Y, et al. COVID-19 infection: the perspectives on immune responses. Cell Death & Differentiation. 2020, 1451-4, 27(5).

Sanders JM, et al. Pharmacologic treatments for coronavirus disease 2019 (COVID-19): a review. Jama. 2020, 1824-36, 323(18).

Guedan S, et al. Engineering and Design of Chimeric Antigen Receptors. Molecular therapy—Methods & Clinical Development Review. 2019, vol. 12, 145-155.

Harvey WT, et al. SARS-CoV-2 variants, spike mutations and immune escape. Nature Review—Microbiology, vol. 19, 409-424 (Jul. 2021).

Moore JB, et al. Cytokine release syndrome in severe COVID-19. Science. 368(6490) 473-474 (May 2020).

Mitchell et al. Selective inhibitors of viral entry. Antiviral Res. Jun. 2017; vol. 142, pp. 37-54. Especially p. 46 col. 1 para 3 continued to p. 46 col. 2 para 3, p. 46 fig 5.

International Search Report mailed Jan. 18, 2022 in PCTUS2153042.

\* cited by examiner

ENGINEERED IMMUNE CELLS TO TARGET SARS-CoV2

CROSS-REFERENCE TO RELATED APPLICATIONS

This application is a 35 U.S.C. § 371 national phase entry of International Patent Application No. PCT/US21/53042 filed Sep. 30, 2021, which claims priority to U.S. Provisional Application No. 63/085,938 filed Sep. 30, 2020, the disclosures of which are incorporated herein by reference in their entireties.

SEQUENCE LISTING

This application contains a Sequence Listing which has been submitted electronically in ASCII format and is hereby incorporated by reference in its entirety. Said ASCII copy, created on Mar. 30, 2023, is named 348358.08301.txt, and is 7,963 bytes in size.

BACKGROUND

New compositions and methods for treating coronaviruses, specifically SARS-CoV-2 (severe acute respiratory syndrome coronavirus 2) are needed.

BRIEF SUMMARY

Provided herein are, inter *alia*, methods, compositions and kits for treating and preventing coronaviruses, e.g., SARS-CoV-2. Also included herein are kits for treating coronaviruses, e.g., SARS-CoV-2.

More particularly, in a first aspect, engineered immune cell are provided that can express a chimeric antigen receptor (CAR) polypeptide comprising an extracellular banana lectin (BanLec) domain.

In one preferred aspect, the BanLc domain comprises an acid sequence having an H84T substitution (i.e. replacing histidine 84 with a threonine).

Preferred cells include those that express a chimeric antigen receptor (CAR) polypeptide comprising an extracellular banana lectin (BanLec) domain, wherein the BanLec domain comprises the amino acid sequence having at least 70, 75 80, 85, 90, 92, 93, 94, 95, 96, 97, 98, 99 or 100% identity with an amino acid sequence of SEQ ID NO: 3 or a fragment thereof, and/or wherein the BanLec domain is encoded by a polynucleotide sequence having at least 70, 75, 80, 85, 90, 92, 93, 94, 95, 96, 97, 98, 99 or 100% identity with the nucleic acid sequence of SEQ ID NO: 4.

Further preferred are engineered immune cells include those where the CAR polypeptide comprises the amino acid sequence having at least 70, 75, 80, 85, 90, 92, 93, 94, 95, 96, 97, 98, 99 or 100% identity with an amino acid sequence of SEQ ID NO: 6 OR SEQ ID NO: 7, and/or wherein the CAR polypeptide is encoded by a sequence that has at least 70, 75, 80, 85, 90, 92, 93, 94, 95, 96, 97, 98, 99 or 100% identity with SEQ ID NO: 8 or SEQ ID NO: 10.

In certain aspects, the immune cells may comprise a natural killer (NK) cell, a T-cell, a B-cell, a macrophage or other myeloid lineage cell, or a mesenchymal stem cell.

In additional aspects, methods are provided for preventing or treating a viral infection, the method comprising: administering to a subject a composition comprising a population of engineered immune cells as described herein expressing a chimeric antigen receptor (CAR) polypeptide comprising an extracellular banana lectin (BanLec) domain, wherein the BanLec domain comprises an amino acid sequence having at least 70, 80, 85, 90, 92, 93, 94, 95, 96, 97, 98, 99 or 100% identity with an amino acid sequence of SEQ ID NO: 3 or a fragment thereof, thereby preventing or treating the viral infection.

In certain aspects, the expressed CAR polypeptide of the cells has at least 70, 75, 80, 85, 90, 92, 93, 94, 95, 96, 97, 98, 99 or 100% identity of SEQ ID NO: 4 or SEQ ID NO: 6.

In certain aspects, the viral infection may be a coronavirus infection, including severe acute respiratory syndrome coronavirus 2 (SARS-CoV-2).

The administered population of engineered immune cells suitably may be autologous or allogenic to the subject.

In certain aspects, the population of engineered immune cells are frozen prior to administrating to the subject.

In preferred methods, one or more additional, distinct antiviral agents can be administered to subject.

In a particular aspect, a chimeric antigen receptor (CAR) that incorporates H84T-BanLec (Banana Lectin (BanLec) that has a H84T point mutation) as the extracellular moiety is provided. In one aspect, a preferred banana lectin (BanLec) has a single point mutation, particularly at position 84 from histidine to threonine, which may be referred to as H84T BanLec, In one aspect, a H84T-BanLec CAR as provided herein can specifically direct NK cell binding of SARS-CoV-2 envelope glycosites to promote viral clearance. In particular aspects, the H84T-BanLec CAR can be stably expressed at high density such as on primary human NK cells during ex vivo expansion. Preferred H84T-BanLec CAR-NK cells can inhibit viral entry of S-protein pseudotyped lentivirus into 293T cells expressing ACE2, the receptor for SARS-CoV-2. NK cells can be activated to secrete inflammatory cytokines when in culture with virally infected cells. The present H84T-BanLec CAR-NK cells therefore can be an effective cell therapy for patients suffering from COVID-19.

Kits are also provided that suitably may include 1) a population of engineered immune cells expressing a chimeric antigen receptor (CAR) polypeptide comprising an extracellular banana lectin (BanLec) domain and optionally 2) instructions for therapeutic use of the cells, such as to treat a subject suffering or suspected of a coronavirus infection.

Other aspects of the invention are disclosed infra.

DESCRIPTION OF THE DRAWINGS

FIG. 2A are histogram plots showing the transduction efficiency of NK-CARs. Flow cytometric detection using rhCD123-His and αHis-APC was used. Isotype: blue, CAR-NK, purple/pink. FIG. 2B is a bar graph showing NK activation measured with co-culture and ELISA for IFNγ secretion. Raji (CD123–), and MV4-11 (CD123+) used as target cells. Bar height represents percent change of IFNγ present in supernatant of co-culture as compared to cells cultured in the absence of target. FIG. 2C is a bar graph showing cytotoxicity evaluated in 72 hr co-culture assays using FACS-based cell counting. Raji Effector:Target cell ratio 1:1, MV-4-11 E:T as noted.

FIG. 3A depict images of blots showing the detection of CAR. Western blot performed with H84T-BanLec antibody. GAPDH used as loading control. FIG. 3B is a graph showing the cytotoxicity of H84T-BanLec CAR T cells to A549 lung cancer cell line. NT (non-transduced) T cells and MRC5 normal lung fibroblast cell line used as controls. Experiments were performed with Incucyte imager using 4 images per well, 3 wells per condition, effector:target ratio of 1:1. The NT T cells are the same T cell population as the CAR, but without CAR expression.

FIG. 6A are histogram plots showing data depicting 293T cell line engineered for hACE expression. Grey: Parental cells, Red: 293T.hACE2. FIG. 6B is a bar graph showing infectivity of replication incompetent retrovirus carrying human firefly Luciferase pseudotyped with the SARS-CoV-2 Spike protein. This viral vector was used to transduce 293T and 293T.hACE2 cells at different viral titers (neat, 1:5, 1:25, 1:125). Viral entry measured by detection of bioluminescence.

FIG. 7 (includes FIGS. 7A-7E). H84T-BanLec.4-1BB.ζ CAR expression in human NK cells.

FIG. 8 (includes FIGS. 8A-8C). Recombinant SARS-CoV-2 proteins bind hACE2.293T.

FIG. 9 (includes FIGS. 9A-9E). CAR-NK cells decrease infectivity of S-protein pseudotyped virus.

and pseudovirus at indicated effector to target (E:T) ratios. Percent infectivity calculated using condition with 293T.ACE2 and pseudovirus alone. (E:T=0.4, p=0.03; E:T=1, p=0.05, n=6, 2 separate experiments using 3 independent NK cell donors, each experiment performed in triplicate).

FIG. 10 (includes FIGS. 10A-10C). Unmodified and BanLec CAR-NK cells are equally cytotoxic against hACE2.293T targets in the absence of pseudovirus.

DETAILED DESCRIPTION

Figure 1:
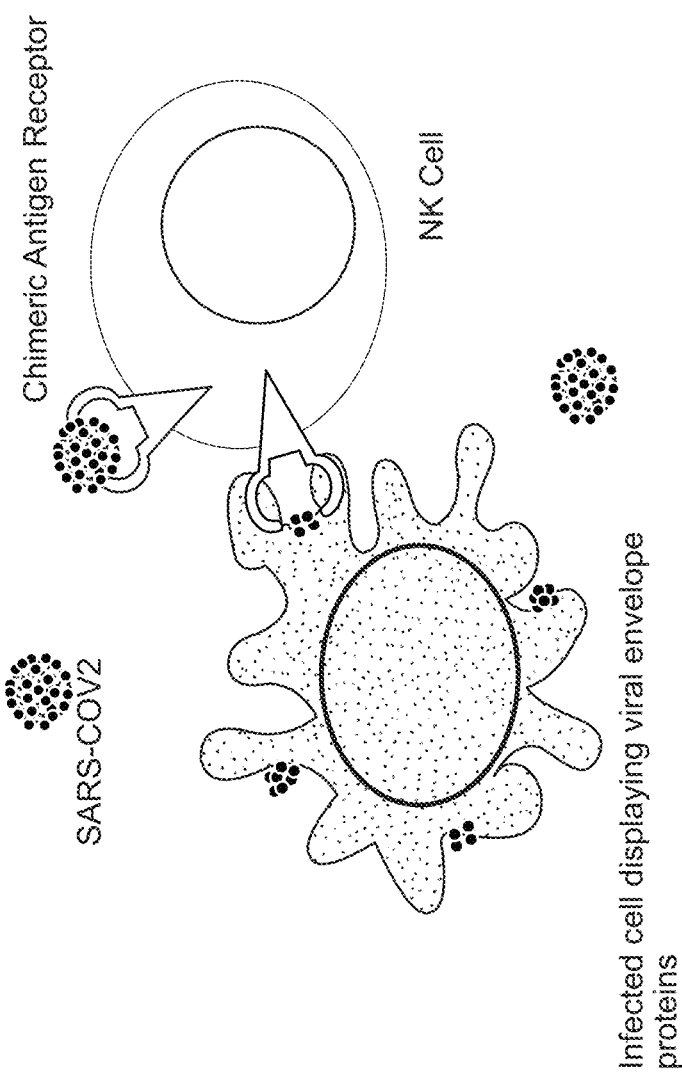
FIG. 1 depicts a schematic of CAR-NK targeting of SARS-COV2 and infected human cells. The schematic depicts that engineered H84T-BanLec. CAR NK cells specifically bind viral envelope and virus-infected cells.

Provided herein are, inter *alia*, methods, compositions and kits for treating and preventing coronaviruses, e.g., SARS-CoV-2.

SARS-CoV-2 is the virus responsible for the COVID-19 global pandemic. H84T-BanLec is a lectin that specifically binds viral glycoproteins, including those of SARS-CoV-2. Though H84T-BanLec a promising antiviral agent, pharmaceutical development is hindered by predicted in vivo chemical and biological degradation. In addition, critically ill patients have immunodysfunction likely to prevent complete virus eradication, even if BanLec binding diminishes infectivity. Provided herein is the use of the binding properties of H84T-BanLec to stimulate powerful NK-cell anti-SARS-CoV-2 activity. Healthy NK (natural killer) cells are genetically engineered to express a receptor coupling glycoprotein recognition with NK activation. T cells were engineered to express a chimeric antigen receptor (CAR) with an H84T-BanLec extracellular domain (BanLec-CAR). BanLec-CAR T cells demonstrates antigen-specific activation and cytotoxicity. However, when adoptively transferred, donor T cells carry the risk of severe graft-versus-host disease. NK cells are an alternate immune effector cell with a critical role in the clearance of viral infections. The infusion of allogeneic donor NK cells has been shown safe in a number of clinical trials.

BanLec CAR-NK cells are used to target SARS-CoV-2 virus and virally infected cells. H84T-BanLec.CAR NK cells are generated. The binding to SARS-CoV-2, specific NK-cell activation, and cytotoxicity against infected cells decorated with SARS-CoV-2 envelope glycoproteins is evaluated. H84T-BanLec.CAR NK cells are tested in animal models of SARS-CoV-2 infection. These cells may represent an off-the-shelf cell therapy for patients suffering from COVID-19 or other coronaviruses.

Significance and Advantages of the Invention

Since late December 2019, SARS-CoV-2, a novel beta-coronavirus, emerged in Wuhan, China and has spread rapidly across the globe. COVID-19, the respiratory infection caused by this virus, has thus far killed over 999,000 and infected over 33.2 million people throughout the world, resulting in one of the deadliest pandemics humanity has ever faced. COVID-19 infection can be severe, with resultant respiratory failure and death. At present, no drug or therapy has been effective in clearance of the viral infection and afflicted patients receive only symptomatic management. The toll on humanity has been enormous. In addition to the disease itself, preventive measures have profoundly altered societal norms and disrupted the global economy. Thus, there is a great need for an effective treatment.

Those critically ill with COVID-19 exhibit immune dysregulation that impairs their capability to clear severe infection. Patients with COVID-19 pneumonia or respiratory failure are lymphopenic with profoundly decreased levels of B, CD4+T, CD8+T, and NK cells. The degree of observed lymphopenia correlates with disease severity. Transfer of healthy donor immune cells to these patients is therefore a strategy with promise. Both T and NK cells are immune effectors with important biological functions in the clearance of pathogens. Acute deterioration with COVID-19 requires emergency treatment options available at the ready.

In comparison to T cells, which must be manufactured from autologous cells in order to prevent graft-versus-host disease, NK cells can be infused from allogeneic donors without this risk. Because of this, a bank of cells collected from healthy donors and frozen can be stored as an off-the-shelf cellular product. These would then be readily available for infusion when needed.

NK cells can be isolated from healthy donors' peripheral blood and expanded ~300-fold ex-vivo after 3 weeks. Once activated, NK cells can then be genetically engineered to specifically target surface antigens using chimeric antigen receptors (CARs). Aliquots of manufactured CAR-NK cells can then be frozen, to establish a master cell bank capable of treating patients suffering from COVID-19 and in need of adequate immune function. Indeed, there are open clinical trials in China investigating the potential role of NK cell (clinicaltrials.gov: NCT04280224) and CAR-NK cell (clinicaltrials.gov: NCT04324996) adoptive transfer as COVID-19 treatment. Expression of a CAR on the surface of NK cells can potentiate enhanced antigen-specific activation and target killing. This boosted function may render CAR-NK cells superior effectors in clearing circulating virus and virally infected cells. Optimal CAR design is essential in modifying NK cell behavior. Appropriate antigen targeting as well as a precise combination of intracellular signaling domains are critical.

Effective transmembrane and intracellular CAR components for NK cell activation were identified. Moreover, instead of targeting a specific antigenic peptide, glycosylation patterns common to viral envelopes are targeted. Decreased expression of target peptides is a mechanism employed by cancer cells to evade targeted immunotherapies. The flexibility in viral targeting diminishes the potential risk of antigen downregulation. At the same time, the specificity in recognition of virally infected cells and viral particles is maintained.

The H84T-BanLec. CAR NK cells are used as specific binders of the SARS-CoV-2 viral envelope. These engineered cells not only bind and eliminate circulating virus, but also clear infected respiratory epithelial cells. Animal testing and further therapeutic development is performed. Given the paucity of treatments available for patients suffering from COVID-19, a cell therapy product providing effector cell function with exquisite antiviral specificity would have profound impact.

BanLec (Banana Lectin)

BanLec is a member of the mannose-specific jacalin-related lectin (mJRL) group that functions as a potent T-cell mitogen. It forms a dimer with two carbohydrate-binding sites (CBS I and CBS II) in each protein subunit. BanLec associates with high-mannose-type N-glycans on the HIV-1 envelope and can thus block viral entry into cells. BanLec has a number of similarities to Concanavalin A and binds to mannose-related carbohydrate structures. It has highly immunogenic properties, including, for example that it induces a strong IgG4 antibody response, and appears to be an important antigen involved in banana allergies.

BanLec Binding of Novel Coronavirus

BanLec is a lectin extracted from the fruit of bananas (Musa acuminate) that binds high mannose glycans. The novel coronavirus, SARS-CoV-2, mediates cell entry via association of its trimeric spike protein with the human Angiotensin-converting enzyme 2 (ACE2) receptor. The spike protein is decorated with underprocessed oligomannose, as is common in other viruses. In the case of SARS-CoV-2, virus-specific high mannose glycosites are in proximity and shield the receptor binding site of the spike protein. They are therefore not likely to be mutagenic hotspots. Notably, BanLec has been experimentally determined to bind HIV, influenza, and other coronaviruses. This binding has an antiviral effect, but wild-type BanLec is also strongly mitogenic and induces unspecific T cell activation. BanLec mitogenicity can be divorced from antiviral activity via a point mutation. A single amino acid substitution (H84T), retains the binding capacity of this BanLec to monosaccharides (responsible for glycoprotein binding), but diminishes the multivalent interactions that drive T-cell activation. Importantly, H84T-BanLec has been shown to inhibit SARS-CoV-2 viral infectivity when tested using the highly susceptible African green monkey Vero-E6 cell line.

An exemplary BanLec amino acid sequence is publically available at the NCBI database under accession number 2BN0_A, incorporated herein by reference in its entirety (SEQ ID NO: 1). The amino acid, H84, is bold and underlined.

```
  1  mngaikvgaw ggnggsafdm gpayriisvk ifsgdvvdgv dvtftyygkt etrhyggsgg
 61  tpheivlqeg eylvgmagev anyhgavvlg klgfstnkka ygpfgntggt pfslpiaagk
121  isgffgrggk fldaigvyle p
```

An exemplary BanLec nucleic acid sequence is publically available at the NCBI database under accession number: AY103481.1, incorporated hereby reference in its entirety (SEQ ID NO: 2). The start and stop codons are bold and underlined.

```
  1  atgaacggag cgatcaaggt gggagcatgg ggagggaacg gagggtcggc cttcgacatg 61  ggacctgctt atcgtatcat cagcgtcaag attttttccg gagacgtggt cgacgccgtg 121  gacgtcacct tcacctacta cgggaagacg gagacccgac acttcggtgg cagcggtggt 181  actccccacg aggtttgcat cactaccaat ctcaaagctc atagctgact gcagattaat 241  ggcttctact tggatgcaga ttgttctgca ggagggcgag tatctggtgg gaatgaaggg 301  agaatttggt aactaccatg gagtggtggt ggtgggggaag cttggcttca gcaccaacaa 361  gaaatcctac ggacctttcg gcaacacggg agggactccc ttctcccttc ctatagcagc 421  aggcaagatc tctggcttct tcggccgtgg cggcgatttt attgacgcca ttggggtcta 481  cttggagcca taattggcca ctgcagtaaa tcacaagagt tgctatgtgc tacttggagt 541  gatgagatga agaatgtctg caataaatgg atcgg
```

An exemplary BanLec amino acid sequence comprising a single amino acid substitution (H84T) that retains binding capacity to monosaccharides, responsible for glycoprotein binding, but diminishes the multivalent interactions that drive T-cell activation is provided below (SEQ ID NO: 3). H84T is bold and underlined.

```
  1  mngaikvgaw ggnggsafdm gpayriisvk ifsgdvvdgv dvtftyygkt etrhyggsgg 61  tpheivlqeg eylvgmagev anytgavvlg klgfstnkka ygpfgntggt pfslpiaagk 121  isgffgrggk fldaigvyle p
```

An H84T BanLec nucleic acid sequence is provided as follows (SEQ ID NO: 4):

```
AATGGCGCTATCAAAGTTGGAGCCTGGGGCGGCAATGGCGGCAGCGCTT

TTGATATGGGCCCTGCCTACCGGATCATCAGCGTGAAGATCTTTAGCGG

CGACGTGGTGGATGGCGTGGACGTGACCTTTACCTACTACGGCAAGACC

GAGACACGGCACTATGGCGGAAGCGGAGGAACACCTCACGAGATCGTTC

TGCAAGAGGGCGAGTACCTCGTTGGAATGGCTGGCGAGGTGGCCAACTA

TACAGGTGCTGTGGTGCTGGGCAAGCTGGGCTTCAGCACCAACAAGAAG

GCCTACGGACCCTTCGGCAATACCGGCGGCACACCTTTTAGCCTGCCTA

TTGCCGCCGGAATCAGCGGCTTTTTTGGCAGAGGCGGCAAGTTCCTGGA

TGCCATCGGAGTGTATCTGGAACCC
```

An H84T BanLec amino acid sequence is provided as follows (SEQ ID NO: 5):

```
NGAIKVGAWGGNGGSAFDMGPAYRIISVKIFSGDVVDGVDVTFTYYGKT

ETRHYGGSGGTPHEIVLQEGEYLVGMAGEVANYTGAVVLGKLGFSTNKK

AYGPFGNTGGTPFSLPIAAGISGFFGRGGKFLDAIGVYLEP
```

NK (Natural Killer) Cells in Viral Infections

NK cells are innate lymphocytes that are important in the control of viral infections. NK cell activation and resultant cytotoxicity is regulated by the interplay of inhibitory and activating receptors. Virally infected cells downregulate the expression of MHC class I molecules, the ligands of NK cell inhibitory receptors. In addition, virus-derived products and stress-induced ligands are expressed on infected cells. These can stimulate NK cell activating receptors and add to the strength of signal initiated by loss of inhibition. These combined signals ultimately control NK cell cytotoxicity against cells under stress and infected with viruses.

CAR-NK Cell Therapy

Engineering NK cells to express chimeric antigen receptors (CARs) can induce antigen-specific activation and killing. (FIG. 1) NK cells do not cause GvHD (graft versus host disease) and do not require HLA (human leukocyte antigen) matching when donor cells are infused. Thus, treatment with allogeneic CAR-NK cells has been shown to be safe in human clinical trial. Severe toxicities associated with CAR-T cell therapy are cytokine release syndrome (CRS) and immune effector cell associated neurotoxicity syndrome (ICANS). These have not been seen in the clinical use of CAR-NK cells.

Figure 2A:
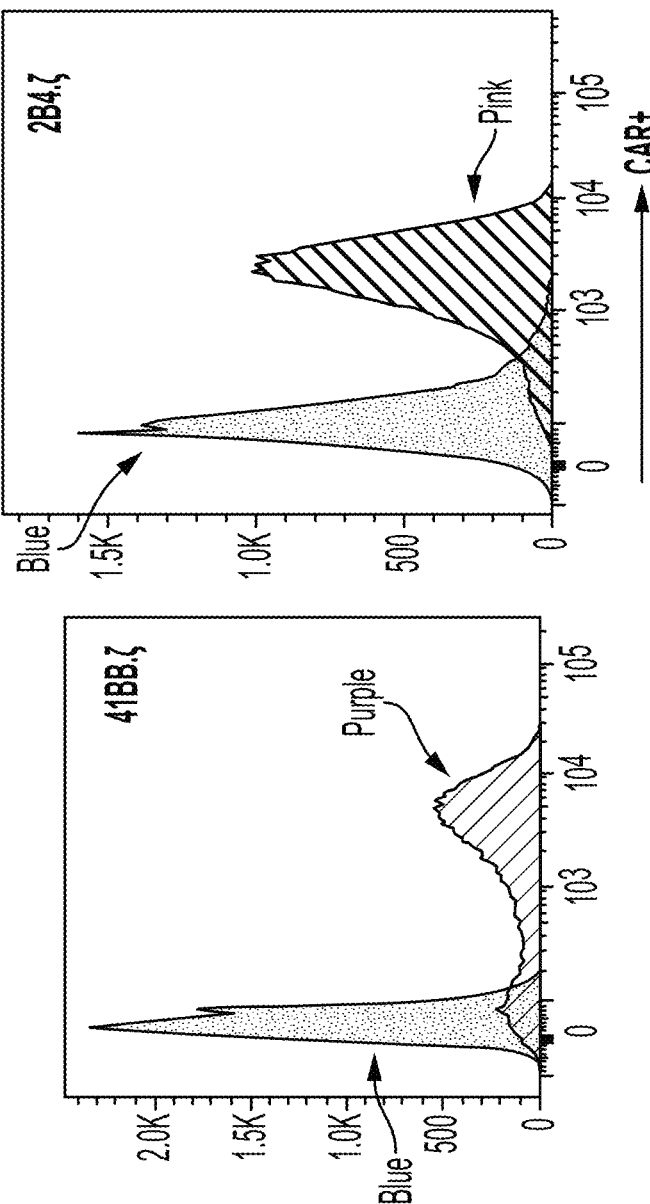
FIGS. 2A-2C are data depicting that 2B4.ζ and e 41BB.z cells are activated by AML targets.
Figures 2B, 2C:
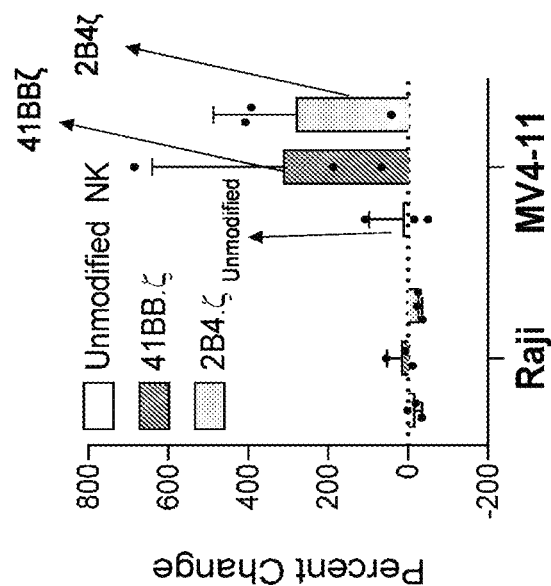

As provided herein, cell engineering is used to design several CARs that augment NK-cell activation. In preclinical evaluation, two CAR structures were observed to be superior for specific activation and cytotoxicity (FIGS. 2A-2C).

Exemplary amino acid sequences of the CARs are shown below: Underlined: Leader sequence; Bold: H84T BanLec, Italic: hinge-transmembrane, Bold and underlined: 41BB, Bold and italic: 2B4, Bold and italic and underlined: TCRζ (zeta).

```
H84T-BanLec.41BB.ζ
                                     (SEQ ID NO: 6)
MDWIWRILFLVGAATGAHSNGAIKVGAWGGNGGSAFDMGPAYRIISVKI

FSGDVVDGVDVTFTYYGKTETRHYGGSGGTPHEIVLQEGEYLVGMAGEV

ANYTGAVVLGKLGFSTNKKAYGPFGNTGGTPFSLPIAAGISGFFGRGGK

FLDAIGVYLEPGGGGSTTTPAPRPPTPAPTIASQPLSLRPEACRPAAGG

AVHTRGLDFACDIYIWAPAGTCGVLLLSLVITLYCKRGRKKLLYIFKQP

FMRPVQTTQEEDGCSCRFPEEEEGGCELRVKFSRSADAPAYQQGQNQLY

NELNLGRREEYDVLDKRRGRDPEMGGKRKNPQEGLYNELQKDKMAEAYS

EIGMKGERRRGKGHDGLYQGLSTATKDTYDALHMQALPPR
```

-continued

H84T-BanLec.2B4.ζ

(SEQ ID NO: 7)

MDWIWRILFLVGAATGAHSNGAIKVGAWGGNGGSAFDMGPAYRIISVKI

FSGDVVDGVDVTFTYYGKTETRHYGGSGGTPHEIVLQEGEYLVGMAGEV

ANYTGAVVLGKLGFSTNKKAYGPFGNTGGTPFSLPIAAGISGFFGRGGK

FLDAIGVYLEPGGGGSQDCQNAHQEFRFWPFLVIIVILSALFLGTLACF

CVWRRKRKEKQSETSPKEFLTIYEDVKDLKTRRNHEQEQTFPGGGSTIY

SMIQSQSSAPTSQEPAYTLYSLIQPSRKSGSRKRNHSPSFNSTIYEVIG

KSQPKAQNPARLSRKELENFDVYSGAGRVKFSRSADAPAYQQGQNQLYN

ELNLGRREEYDVLDKRRGRDPEMGGKPQRRKNPQEGLYNELQKDKMAEA

YSEIGMKGERRRGKGHDGLYQGLSTATKDTYDALHMQALPPR

In examples, the leader sequence (alternatively "signal peptide") depicted in the CAR peptides above is an N-terminal portion of the protein that assists it across the membrane of the rough endoplasmic reticulum, where it is synthesized, but which is cleaved from the protein even before the synthesis of the protein is complete, thereby producing a mature peptide (e.g., without the leader sequence).

Exemplary nucleic acid sequences and amino acid sequences of the CARs are shown below as SEQ ID NO:8 and SEQ ID NO:9 respectively:

2B4.z CAR (SEQ ID NO: 8):

ATGGACTGGATCTGGCGCATCCTGTTTCTTGTGGGAGCCGCCACAGGCG

CCCATAGCAATGGCGCTATCAAAGTTGGAGCCTGGGGCGGCAATGGCGG

CAGCGCTTTTGATATGGGCCCTGCCTACCGGATCATCAGCGTGAAGATC

TTTAGCGGCGACGTGGTGGATGGCGTGGACGTGACCTTTACCTACTACG

GCAAGACCGAGACACGGCACTATGGCGGAAGCGGAGGAACACCTCACGA

GATCGTTCTGCAAGAGGGCGAGTACCTCGTTGGAATGGCTGGCGAGGTG

GCCAACTATACAGGTGCTGTGGTGCTGGGCAAGCTGGGCTTCAGCACCA

ACAAGAAGGCCTACGGACCCTTCGGCAATACCGGCGGCACACCTTTTAG

CCTGCCTATTGCCGCCGGAATCAGCGGCTTTTTTGGCAGAGGCGGCAAG

TTCCTGGATGCCATCGGAGTGTATCTGGAACCCGGAGGGGGCGGATCCC

AGGATTGCCAGAATGCCCACCAAGAGTTCCGGTTCTGGCCCTTCCTGGT

CATCATCGTGATCCTGAGCGCCCTGTTCCTGGGCACCCTGGCCTGTTTT

TGCGTGTGGCGCAGAAAGCGCAAAGAGAAGCAGAGCGAGACAAGCCCCA

AAGAGTTCCTGACCATCTACGAGGACGTGAAGGACCTGAAAACCCGGCG

GAACCACGAGCAAGAGCAGACCTTTCCTGGCGGCGGAAGCACCATCTAC

AGCATGATCCAGAGCCAGAGCAGCGCCCCTACAAGCCAAGAGCCTGCCT

ACACACTGTACTCCCTGATCCAGCCTAGCAGAAAGAGCGGCAGCCGGAA

GAGAAATCACAGCCCCAGCTTCAACAGCACGATCTACGAAGTGATCGGC

AAGAGCCAGCCAAAGGCTCAGAACCCTGCCAGACTGAGCCGGAAAGAGC

TGGAAAACTTCGACGTGTACTCTGGGGCCGGCAGAGTGAAGTTCAGCAG

ATCAGCCGATGCTCCCGCCTATCAGCAGGGCCAGAACCAGCTGTACAAC

GAGCTGAACCTGGGGAGAAGAGAAGAGTACGACGTGCTGGACAAGCGGA

-continued

GAGGCAGAGATCCTGAGATGGGCGGAAAGCCCCAGCGGAGAAAGAATCC

TCAAGAGGGCCTGTATAATGAGCTGCAGAAAGACAAGATGGCCGAGGCC

TACAGCGAGATCGGAATGAAGGGCGAGCGCAGAAGAGGCAAGGGACACG

ATGGACTGTACCAGGGCCTGAGCACCGCCACCAAGGATACCTATGATGC

CCTGCACATGCAGGCCCTGCCTCCAAGATGA

SEQ ID NO. 9

MDWIWRILFLVGAATGAHSNGAIKVGAWGGNGGSAFDMGPAYRIISVKI

FSGDVVDGVDVTFTYYGKTETRHYGGSGGTPHEIVLQEGEYLVGMAGEV

ANYTGAVVLGKLGFSTNKKAYGPFGNTGGTPFSLPIAAGISGFFGRGGK

FLDAIGVYLEPGGGGSQDCQNAHQEFRFWPFLVIIVILSALFLGTLACF

CVWRRKRKEKQSETSPKEFLTIYEDVKDLKTRRNHEQEQTFPGGGSTIY

SMIQSQSSAPTSQEPAYTLYSLIQPSRKSGSRKRNHSPSFNSTIYEVIG

KSQPKAQNPARLSRKELENFDVYSGAGRVKFSRSADAPAYQQGQNQLYN

ELNLGRREEYDVLDKRRGRDPEMGGKPQRRKNPQEGLYNELQKDKMAEA

YSEIGMKGERRRGKGHDGLYQGLSTATKDTYDALHMQALPPR

Further exemplary nucleic acid sequences and amino acid sequences of the CARs are shown below as SEQ ID NO: 10 and SEQ ID NO: 11 respectively:

41BB.z CAR (SEQ ID NO: 10)

ATGGACTGGATCTGGCGCATCCTGTTTCTTGTGGGAGCCGCGCACAGGCG

CCCATAGCAATGGCGCTATCAAAGTTGGAGCCTGGGGCGGCAATGGCGG

CAGCGCTTTTGATATGGGCCCTGCCTACCGGATCATCAGCGTGAAGATC

TTTAGCGGCGACGTGGTGGATGGCGTGGACGTGACCTTTACCTACTACG

GCAAGACCGAGACACGGCACTATGGCGGAAGCGGAGGAACACCTCACGA

GATCGTTCTGCAAGAGGGCGAGTACCTCGTTGGAATGGCTGGCGAGGTG

GCCAACTATACAGGTGCTGTGGTGCTGGGCAAGCTGGGCTTCAGCACCA

ACAAGAAGGCCTACGGACCCTTCGGCAATACCGGCGGCACACCTTTTAG

CCTGCCTATTGCCGCCGGAATCAGCGGCTTTTTTGGCAGAGGCGGCAAG

TTCCTGGATGCCATCGGAGTGTATCTGGAACCCGGAGGGGGCGGATCCA

CAACAACCCCTGCCCCCAGACCTCCTACCCCAGCCCCTACAATTGCCAG

CCAGCCTCTGAGCCTGAGGCCCGAGGCTTGTAGACCTGCTGCTGGCGGA

GCCGTGCACACCAGAGGACTGGATTTCGCCTGCGACATCTACATCTGGG

CCCCTCTGGCCGGCACATGCGGAGTGCTGCTGCTGAGCCTCGTGATCAC

CCTGTACTGCAAGCGGGGCAGAAAGAAGCTGCTGTACATCTTCAAGCAG

CCCTTCATGCGGCCCGTGCAGACCACACAGGAAGAGGACGGCTGCTCCT

GCCGGTTCCCCGAGGAAGAAGAAGGCGGCTGCGAGCTGAGAGTGAAGTT

CTCTAGAAGCGCCGACGCCCCTGCCTACCAGCAGGGACAGAACCAGCTG

TACAACGAGCTGAACCTGGGCAGACGGGAAGAGTACGACGTGCTGGACA

AGCGGAGAGGCCGGGACCCTGAGATGGGAGGCAAGAGAAAGAACCCCCA

GGAAGGCCTGTATAACGAACTGCAGAAAGACAAGATGGCCGAGGCCTAC

AGCGAGATCGGAATGAAGGGCGAGCGGAGAAGAGGCAAGGGCCACGATG

-continued

```
GACTGTATCAGGGCCTGAGCACCGCCACCAAGGACACCTATGACGCCCT

GCACATGCAGGCCCTGCCCCCCAGA
```

SEQ ID NO. 11

```
MDWIWRILFLVGAATGAHSNGAIKVGAWGGNGGSAFDMGPAYRIISVKI

FSGDVVDGVDVTFTYYGKTETRHYGGSGGTPHEIVLQEGEYLVGMAGEV

ANYTGAVVLGKLGFSTNKKAYGPFGNTGGTPFSLPIAAGISGFFGRGGK

FLDAIGVYLEPGGGGSTTTPAPRPPTPAPTIASQPLSLRPEACRPAAGG

AVHTRGLDFACDIYIWAPLAGTCGVLLLSLVITLYCKRGRKKLLYIFKQ

PFMRPVQTTQEEDGCSCRFPEEEEGGCELRVKFSRSADAPAYQQGQNQL

YNELNLGRREEYDVLDKRRGRDPEMGGKRKNPQEGLYNELQKDKMAEAY

SEIGMKGERRRGKGHDGLYQGLSTATKDTYDALHMQALPPR
```

CAR-NK Therapy for SARS-CoV-2 Eradication

The novel coronavirus SARS-CoV-2 has created havoc and placed international healthcare systems under unprecedented stress. Lack of prior exposure and a high fatality rate have together resulted in a global pandemic. Currently, there is no treatment proven effective against SARS-CoV-2. Critically ill patients demonstrate immune dysregulation, with both reduced number and function of effector cells. NK cell dysfunction impacts host ability to clear viral infections. Adoptive transfer of healthy donor immune cells can temporarily repopulate host innate immunity. NK cells can be frozen and stored as an "off-the-shelf" product, readily available when needed. However, unmodified NK cells may demonstrate non-specific activation and uncontrolled activity. Engineering NK cells with Chimeric Antigen Receptors (CARs) can direct antiviral activity and provision the cells with boosted killing potential.

CAR functionality and safety is heavily dependent on target selection. The SARS-CoV-2 viral envelope is heavily glycosylated, with expression of glycosites distinct from those detected on healthy human cells. CAR targeting of T cells to membranous high mannose containing glycoproteins was shown. NK cells expressing a CAR comprised of a targeting domain that binds high mannose binds to SARS-CoV-2 envelope proteins. Indeed, the spike(S) protein, critical for viral cell entry via binding of the human ACE2 receptor, displays viral-specific glycosites.

BanLec is a lectin derived from bananas that when modified with a single amino acid point mutation (H84T) specifically binds high mannose, without triggering T cell mitogenicity. The resultant H84T-BanLec can bind glycoproteins incorporated into the envelopes of multiple viruses. H84T-BanLec alone has been shown to reduce viral infectivity and promote survival in animal models of viral infection. However, lectins are subject to chemical and biomolecular degradation, making administration and pharmacologic stability a barrier to human treatment.

H84T-BanLec was engineered as the targeting moiety of a CAR expressed on T cells. Due to rapid cell division and dysregulated post-translational processing, transformed cells can display abnormally glycosylated membrane proteins. Indeed, H84T-BanLec.CAR T cells can promote specific killing of lung cancer cells, without affecting normal lung fibroblasts. Though powerful cytotoxic immune effectors, T cells are not an ideal cell therapy agent to treat SARS-CoV-2 infection.

As provided herein, the safety profile and favorable characteristics of NK cells is shown. Specificity is improved and activation is boosted by expressing H84T-BanLec.CAR on NK cells. H84T-BanLec. CAR NK cell binding and activation by SARS-CoV-2 envelope proteins is shown as a step to further clinical development.

Viral Glycoprotein

A viral envelope is the outermost layer of many types of viruses. It protects the genetic material in their life-cycle when traveling between host cells. Not all viruses have envelopes.

The envelopes are typically derived from portions of the host cell membranes (phospholipids and proteins), but include some viral glycoproteins. They may help viruses avoid the host immune system. Glycoproteins on the surface of the envelope serve to identify and bind to receptor on the host's membrane. The viral envelope then fuses with the host's membrane, allowing the capsid and viral genome to enter and infect the host. All enveloped viruses also have a capsid, another protein layer, between the envelope and the genome.

Spike Proteins

The S protein is a highly glycosylated and large type I transmembrane fusion protein that is made up of 1,160 to 1,400 amino acids, depending upon the type of virus. As compared to the M and E proteins that are primarily involved in virus assembly, the S protein plays a crucial role in binding host cells and initiating infection.

S proteins of coronaviruses can be divided into two important functional subunits, of which include the N-terminal S1 subunit, which forms of the globular head of the S protein, and the C-terminal S2 region that forms the stalk of the protein and is directly embedded into the viral envelope. Upon interaction with a potential host cell, the S1 subunit will recognize and bind to receptors on the host cell, whereas the S2 subunit, which is the most conserved component of the S protein, will be responsible for fusing the envelope of the virus with the host cell membrane.

Coronavirus infect human respiratory epithelial cells through interaction with the human ACE2 (angiotensin-converting enzyme 2) receptor. The spike protein is a large type I transmembrane protein containing two subunits, S1 and S2. S1 mainly contains a receptor binding domain (RBD), which is responsible for recognizing the ACE2 cell surface receptor. S2 contains basic elements needed for the membrane fusion. The S protein plays key parts in the induction of neutralizing-antibody and T-cell responses, as well as protective immunity.

An amino acid sequence of a surface glycoprotein for SARS-CoV-2 (severe acute respiratory syndrome coronavirus 2) is publically available at the NCBI database under accession number: QHD43416.1, incorporated herein by reference (SEQ ID NO: 12).

```
  1  mfvflvllpl vssqcvnltt rtqlppaytn sftrgvyypd kvfrssvlhs tqdlflpffs 61  nvtwfhaihv sgtngtkrfd npvlpfndgv yfasteksni irgwifgttl dsktqslliv 121  nnatnvvikv cefqfondpf lgvyyhknnk swmesefrvy ssannctfey vsqpflmdle 181  gkqgnfknlr efvfknidgy fkiyskhtpi nlvrdlpqgf saleplvdlp iginitrfqt
```

-continued

```
 241  llalhrsylt pgdsssgwta gaaayyvgyl qprtfllkyn engtitdavd caldplsetk 301  ctlksftvek giyqtsnfrv qptesivrfp nitnlcpfge vfnatrfasv yawnrkrisn 361  cvadysvlyn sasfstfkcy gvsptkindl cftnvyadsf virgdevrqi apgqtgkiad 421  ynyklpddft gcviawnsnn ldskvggnyn ylyrlfrksn lkpferdist eiyqagstpc 481  ngvegfncyf plqsygfqpt ngvgyqpyrv vvlsfellha patvcgpkks tnlvknkcvn 541  fnfngltgtg vltesnkkfl pfqqfgrdia dttdavrdpq tleilditpc sfggvsvitp 601  gtntsnqvav lyqdvnctev pvaihadqlt ptwrvystgs nvfqtragcl igaehvnnsy 661  ecdipigagi casyqtqtns prrarsvasq siiaytmslg aensvaysnn siaiptnfti 721  svtteilpvs mtktsvdctm yicgdstecs nlllqygsfc tqlnraltgi aveqdkntqe 781  vfaqvkqiyk tppikdfggf nfsqilpdps kpskrsfied llfnkvtlad agfikqygdc 841  lgdiaardli caqkfngltv lpplltdemi aqytsallag titsgwtfga gaalqipfam 901  qmayrfngig vtqnvlyenq klianqfnsa igkiqdslss tasalgklqd vvnqnaqaln 961  tlvkqlssnf gaissvlndi lsrldkveae vqidrlitgr lqslqtyvtq qliraaeira 1021  sanlaatkms ecvlgqskrv dfcgkgyhlm sfpqsaphgv vflhvtyvpa qeknfttapa 1081  ichdgkahfp regvfvsngt hwfvtqrnfy epqiittdnt fvsgncdvvi givnntvydp 1141  lqpeldsfke eldkyfknht spdvdlgdis ginasvvniq keidrlneva knlneslidl 1201  qelgkyegyi kwpwyiwlgf iagliaivmv timlccmtsc csclkgccsc gscckfdedd 1261  sepvlkgvkl hyt
```

A nucleotide sequence of a surface glycoprotein for SARS-COV2 (severe acute respiratory syndrome coronavirus 2) is publically available at the NCBI database under accession number: MN908947.31, incorporated herein by reference (SEQ ID NO: 13). The start and stop codons are bold and underlined.

```
   1  attaaaggtt tataccttcc caggtaacaa accaaccaac tttcgatctc ttgtagatct 61  gttctctaaa cgaactttaa aatctgtgtg gctgtcactc ggctgcatgc ttagtgcact 121  cacgcagtat aattaataac taattactgt cgttgacagg acacgagtaa ctcgtctatc 181  ttctgcaggc tgcttacggt ttcgtccgtg ttgcagccga tcatcagcac atctaggttt 241  cgtccgggtg tgaccgaaag gtaagatgga gagccttgtc cctggtttca acgagaaaac 301  acacgtccaa ctcagtttgc ctgttttaca ggttcgcgac gtgctcgtac gtggctttgg 361  agactccgtg gaggaggtct tatcagaggc acgtcaacat cttaaagatg cacttgtgg 421  cttagtagaa gttgaaaaag gcgttttgcc tcaacttgaa cagccctatg tgttcatcaa 481  acgttcggat gctcgaactg cacctcatgt tcatgttatg gttgagctgg tagcagaact 541  cgaaggcatt cagtacggtc gtagtggtga cacttggt gtccttgtcc ctcatgtggg 601  cgaaatacca gtggcttacc gcaaggttct tcttcgtaag aacggtaata aaggagctgg 661  tggccatagt tacggcgccg atctaaagtc atttgactta ggcgacgagc ttggcactga 721  tccttatgaa gattttcaag aaaactggaa cactaaacat agcagtggtg ttacccgtga 781  actcatgcgt gagcttaacg gaggggcata cactcgctat gtcgataaca acttctgtgg 841  ccctgatggc tacctcttg agtgcattaa agaccttcta gcacgtgctg gtaaagcttc 901  atgcactttg tccgaacaac tggactttat tgacactaag aggggtgtat actgctgccg 961  tgaacatgag catgaaattg cttggtacac ggaacgttct gaaaagagct atgaattgca 1021  gacaccttt gaaattaaat tggcaaagaa atttgacacc ttcaatgggg aatgtccaaa 1081  ttttgtattt cccttaaatt ccataatcaa gactattcaa ccaaggggttg aaaagaaaaa
```

-continued

```
1141  gcttgatggc tttatgggta gaattcgatc tgtctatcca gttgcgtcac caaatgaatg 1201  caaccaaatg tgcctttcaa ctctcatgaa gtgtgatcat tgtggtgaaa cttcatggca 1261  gacgggcgat tttgttaaag ccacttgcga attttgtggc actgagaatt tgactaaaga 1321  aggtgccact acttgtggtt acttacccca aaatgctgtt gttaaaattt attgtccagc 1381  atgtcacaat tcagaagtag gacctgagca tagtcttgcc gaataccata tgaatctgg 1441  cttgaaaacc attcttcgta agggtggtcg cactattgcc tttggaggct gtgtgttctc 1501  ttatgttggt tgccataaca agtgtgccta ttgggttcca cgtgctagcg ctaacatagg 1561  ttgtaaccat acaggtgttg ttggagaagg ttccgaaggt cttaatgaca accttcttga 1621  aatactccaa aaagagaaag tcaacatcaa tattgttggt gactttaaac ttaatgaaga 1681  gatcgccatt attttggcat ctttttctgc ttccacaagt gcttttgtgg aaactgtgaa 1741  aggtttggat tataaagcat tcaaacaaat tgttgaatcc tgtggtaatt ttaaagttac 1801  aaaaggaaaa gctaaaaaag gtgcctggaa tattggtgaa cagaaatcaa tactgagtcc 1861  tctttatgca tttgcatcag aggctgctcg tgttgtacga tcaattttct cccgcactct 1921  tgaaactgct caaaattctg tgcgtgtttt acagaaggcc gctataacaa tactagatgg 1981  aatttcacag tattcactga gactcattga tgctatgatg ttcacatctg atttggctac 2041  taacaatcta gttgtaatgg cctacattac aggtggtgtt gttcagttga cttcgcagtg 2101  gctaactaac atctttggca ctgtttatga aaaactcaaa cccgtccttg attggcttga 2161  agagaagttt aaggaaggtg tagagtttct tagagacggt tgggaaattg ttaaatttat 2221  ctcaacctgt gcttgtgaaa ttgtcggtgg acaaattgtc acctgtgcaa aggaaattaa 2281  ggagagtgtt cagacattct ttaagcttgt aaataaattt ttggctttgt gtgctgactc 2341  tatcattatt ggtggagcta aacttaaagc cttgaattta ggtgaaacat ttgtcacgca 2401  ctcaaaggga ttgtacagaa agtgtgttaa atccagagaa gaaactggcc tactcatgcc 2461  tctaaaagcc ccaaaagaaa ttatcttctt agagggagaa acacttccca cagaagtgtt 2521  aacagaggaa gttgtcttga aaactggtga tttacaacca ttagaacaac ctactagtga 2581  agctgttgaa gctccattgg ttggtacacc agtttgtatt aacgggctta tgttgctcga 2641  aatcaaagac acagaaaagt actgtgccct tgcacctaat atgatggtaa caaacaatac 2701  cttcacactc aaaggcggtg caccaacaaa ggttactttt ggtgatgaca ctgtgataga 2761  agtgcaaggt tacaagagtg tgaatatcac ttttgaactt gatgaaagga ttgataaagt 2821  acttaatgag aagtgctctg cctatacagt tgaactcggt acagaagtaa atgagttcgc 2881  ctgtgttgtg gcagatgctg tcataaaaac tttgcaacca gtatctgaat tacttacacc 2941  actgggcatt gatttagatg agtggagtat ggctacatac tacttatttg atgagtctgg 3001  tgagtttaaa ttggcttcac atatgtattg ttctttctac cctccagatg aggatgaaga 3061  agaaggtgat tgtgaagaag aagagtttga gccatcaact caatatgagt atggtactga 3121  agatgattac caaggtaaac ctttggaatt tggtgccact tctgctgctc ttcaacctga 3181  agaagagcaa gaagaagatt ggttagatga tgatagtcaa caaactgttg gtcaacaaga 3241  cggcagtgag gacaatcaga caactactat tcaaacaatt gttgaggttc aacctcaatt 3301  agagatggaa cttacaccag ttgttcagac tattgaagtg aatagtttta gtggttattt 3361  aaaacttact gacaatgtat acattaaaaa tgcagacatt gtggaagaag ctaaaaaggt 3421  aaaaccaaca gtggttgtta atgcagccaa tgtttacctt aaacatggag gaggtgttgc 3481  aggagcctta aataaggcta ctaacaatgc catgcaagtt gaatctgatg attacatagc
```

-continued

```
3541  tactaatgga ccacttaaag tgggtggtag ttgtgtttta agcggacaca atcttgctaa 3601  acactgtctt catgttgtcg gcccaaatgt taacaaaggt gaagacattc aacttcttaa 3661  gagtgcttat gaaaatttta atcagcacga agttctactt gcaccattat tatcagctgg 3721  tattttttggt gctgacccta tacattcttt aagagtttgt gtagatactg ttcgcacaaa 3781  tgtctactta gctgtctttg ataaaaatct ctatgacaaa cttgtttcaa gcttttttgga 3841  aatgaagagt gaaaagcaag ttgaacaaaa gatcgctgag attcctaaag aggaagttaa 3901  gccatttata actgaaagta aaccttcagt tgaacagaga aaacaagatg ataagaaaat 3961  caaagcttgt gttgaagaag ttacaacaac tctggaagaa actaagttcc tcacagaaaa 4021  cttgttactt tatattgaca ttaatggcaa tcttcatcca gattctgcca ctcttgttag 4081  tgacattgac atcactttct taaagaaaga tgctccatat atagtgggtg atgttgttca 4141  agagggtgtt ttaactgctg tggttatacc tactaaaaag gctggtggca ctactgaaat 4201  gctagcgaaa gctttgagaa aagtgccaac agacaattat ataaccactt acccgggtca 4261  gggtttaaat ggttacactg tagaggaggc aaagacagtg cttaaaaagt gtaaaagtgc 4321  cttttacatt ctaccatcta ttatctctaa tgagaagcaa gaaattcttg gaactgtttc 4381  ttggaatttg cgagaaatgc ttgcacatgc agaagaaaca cgcaaattaa tgcctgtctg 4441  tgtggaaact aaagccatag tttcaactat acagcgtaaa tataagggta ttaaaataca 4501  agagggtgtg gttgattatg gtgctagatt ttacttttac accagtaaaa caactgtagc 4561  gtcacttatc aacacactta acgatctaaa tgaaactctt gttacaatgc cacttggcta 4621  tgtaacacat ggcttaaatt tggaagaagc tgctcggtat atgagatctc tcaaagtgcc 4681  agctacagtt tctgtttctt cacctgatgc tgttacagcg tataatggtt atcttacttc 4741  ttcttctaaa acacctgaag aacattttat tgaaaccatc tcacttgctg gttcctataa 4801  agattggtcc tattctggac aatctacaca actaggtata gaatttctta agagaggtga 4861  taaaagtgta tattacacta gtaatcctac cacattccac ctagatggtg aagttatcac 4921  ctttgacaat cttaagacac ttctttctttt gagagaagtg aggactatta ggtgtttac 4981  aacagtagac aacattaacc tccacacgca agttgtggac atgtcaatga catatggaca 5041  acagtttggt ccaacttatt tggatggagc tgatgttact aaaataaaac ctcataattc 5101  acatgaaggt aaaacatttt atgtttttacc taatgatgac actctacgtg ttgaggcttt 5161  tgagtactac cacacaactg atcctagttt tctgggtagg tacatgtcag cattaaatca 5221  cactaaaaag tggaaatacc cacaagttaa tggtttaact tctattaaat gggcagataa 5281  caactgttat cttgccactg cattgttaac actccaacaa atagagttga agtttaatcc 5341  acctgctcta caagatgctt attacagagc aagggctggt gaagctgcta cttttgtgc 5401  acttatctta gcctactgta ataagacagt aggtgagtta ggtgatgtta gagaaacaat 5461  gagttacttg tttcaacatg ccaatttaga ttcttgcaaa agagtcttga acgtggtgtg 5521  taaaacttgt ggacaacagc agacaacccct taagggtgta gaagctgtta tgtacatggg 5581  cacactttct tatgaacaat ttaagaaagg tgttcagata ccttgtacgt gtggtaaaca 5641  agctacaaaa tatctagtac aacaggagtc accttttgtt atgatgtcag caccacctgc 5701  tcagtatgaa cttaagcatg gtacatttac ttgtgctagt gagtacactg gtaattacca 5761  gtgtggtcac tataaacata taacttctaa agaaactttg tattgcatag acggtgcttt 5821  acttacaaag tcctcagaat acaaaggtcc tattacggat gttttctaca agaaaacag 5881  ttacacaaca accataaaac cagttactta taaattggat ggtgttgttt gtacagaaat 5941  tgaccctaag ttggacaatt attataagaa agacaattct tatttcacag agcaaccaat
```

-continued

```
6001  tgatcttgta ccaaaccaac catatccaaa cgcaagcttc gataatttta agtttgtatg 6061  tgataatatc aaatttgctg atgatttaaa ccagttaact ggttataaga aacctgcttc 6121  aagagagctt aaagttacat ttttccctga cttaaatggt gatgtggtgg ctattgatta 6181  taaacactac acaccctctt ttaagaaagg agctaaattg ttacataaac ctattgtttg 6241  gcatgttaac aatgcaacta taaagccac gtataaacca aatacctggt gtatacgttg 6301  tctttggagc acaaaaccag ttgaaacatc aaattcgttt gatgtactga agtcagagga 6361  cgcgcaggga atggataatc ttgcctgcga agatctaaaa ccagtctctg aagaagtagt 6421  ggaaaatcct accatacaga aagacgttct tgagtgtaat gtgaaaacta ccgaagttgt 6481  aggagacatt atacttaaac cagcaaataa tagtttaaaa attacagaag aggttggcca 6541  cacagatcta atggctgctt atgtagacaa ttctagtctt actattaaga aacctaatga 6601  attatctaga gtattaggtt tgaaaaccct tgctactcat ggtttagctg ctgttaatag 6661  tgtcccttgg gatactatag ctaattatgc taagcctttt cttaacaaag ttgttagtac 6721  aactactaac atagttacac ggtgtttaaa ccgtgtttgt actaattata tgccttattt 6781  ctttactttta ttgctacaat gtgtgacttt tactagaagt acaaattcta gaattaaagc 6841  atctatgccg actactatag caaagaatac tgttaagagt gtcggtaaat tttgtctaga 6901  ggcttcattt aattatttga agtcacctaa tttttctaaa ctgataaata ttataatttg 6961  gtttttacta ttaagtgttt gcctaggttc tttaatctac tcaaccgctg ctttaggtgt 7021  tttaatgtct aatttaggca tgccttctta ctgtactggt tacagagaag gctatttgaa 7081  ctctactaat gtcactattg caacctactg tactggttct ataccttgta gtgtttgtct 7141  tagtggttta gattctttag acacctatcc ttctttagaa actatacaaa ttaccatttc 7201  atctttttaaa tgggatttaa ctgcttttgg cttagttgca gagtggtttt tggcatatat 7261  tctttttcact aggttttttct atgtacttgg attggctgca atcatgcaat tgtttttcag 7321  ctattttgca gtacatttta ttagtaattc ttggcttatg tggttaataa ttaatcttgt 7381  acaaatggcc ccgatttcag ctatggttag aatgtacatc ttctttgcat cattttatta 7441  tgtatggaaa agttatgtgc atgttgtaga cggttgtaat tcatcaactt gtatgatgtg 7501  ttacaaacgt aatagagcaa caagagtcga atgtacaact attgttaatg gtgttagaag 7561  gtcctttttat gtctatgcta atggaggtaa aggcttttgc aaactacaca attggaattg 7621  tgttaattgt gatacattct gtgctggtag tacatttatt agtgatgaag ttgcgagaga 7681  cttgtcacta cagtttaaaa gaccaataaa tcctactgac cagtcttctt acatcgttga 7741  tagtgttaca gtgaagaatg gttccatcca tctttacttt gataaagctg gtcaaaagac 7801  ttatgaaaga cattctctct ctcattttgt taacttagac aacctgagag ctaataacac 7861  taaaggttca ttgcctatta atgttatagt ttttgatggt aaatcaaaat gtgaagaatc 7921  atctgcaaaa tcagcgtctg tttactacag tcagcttatg tgtcaaccta tactgttact 7981  agatcaggca ttagtgtctg atgttggtga tagtgcggaa gttgcagtta aaatgtttga 8041  tgcttacgtt aatacgtttt catcaacttt taacgtacca atggaaaaac tcaaaacact 8101  agttgcaact gcagaagctg aacttgcaaa gaatgtgtcc ttagacaatg tcttatctac 8161  ttttatttca gcagctcggc aagggtttgt tgattcagat gtagaaacta aagatgttgt 8221  tgaatgtctt aaattgtcac atcaatctga catagaagtt actggcgata gttgtaataa 8281  ctatatgctc acctataaca aagttgaaaa catgacaccc cgtgaccttg gtgcttgtat 8341  tgactgtagt gcgcgtcata ttaatgcgca ggtagcaaaa agtcacaaca ttgctttgat
```

-continued

```
 8401 atggaacgtt aaagatttca tgtcattgtc tgaacaacta cgaaaacaaa tacgtagtgc 8461 tgctaaaaag aataacttac cttttaagtt gacatgtgca actactagac aagttgttaa 8521 tgttgtaaca acaaagatag cacttaaggg tggtaaaatt gttaataatt ggttgaagca 8581 gttaattaaa gttacacttg tgttcctttt tgttgctgct attttctatt taataacacc 8641 tgttcatgtc atgtctaaac atactgactt ttcaagtgaa atcataggat acaaggctat 8701 tgatggtggt gtcactcgtg acatagcatc tacagatact tgtttttgcta acaaacatgc 8761 tgattttgac acatggttta gccagcgtgg tggtagttat actaatgaca aagcttgccc 8821 attgattgct gcagtcataa caagagaagt gggttttgtc gtgcctggtt tgcctggcac 8881 gatattacgc acaactaatg gtgacttttt gcatttctta cctagagttt ttagtgcagt 8941 tggtaacatc tgttacacac catcaaaact tatagagtac actgactttg caacatcagc 9001 ttgtgttttg gctgctgaat gtacaatttt taaagatgct tctggtaagc cagtaccata 9061 ttgttatgat accaatgtac tagaaggttc tgttgcttat gaaagtttac gccctgacac 9121 acgttatgtg ctcatggatg gctctattat tcaatttcct aacacctacc ttgaaggttc 9181 tgttagagtg gtaacaactt ttgattctga gtactgtagg cacggcactt gtgaaagatc 9241 agaagctggt gtttgtgtat ctactagtgg tagatgggta cttaacaatg attattacag 9301 atctttacca ggagttttct gtggtgtaga tgctgtaaat ttacttacta atatgtttac 9361 accactaatt caacctattg gtgctttgga catatcagca tctatagtag ctggtggtat 9421 tgtagctatc gtagtaacat gccttgccta ctattttatg aggtttagaa gagcttttgg 9481 tgaatacagt catgtagttg cctttaatac tttactattc cttatgtcat tcactgtact 9541 ctgtttaaca ccagtttact cattcttacc tggtgtttat tctgttattt acttgtactt 9601 gacattttat cttactaatg atgtttcttt tttagcacat attcagtgga tggttatgtt 9661 cacacctttta gtacctttct ggataacaat tgcttatatc atttgtattt ccacaaagca 9721 tttctattgg ttctttagta attacctaaa gagacgtgta gtctttaatg gtgtttcctt 9781 tagtactttt gaagaagctg cgctgtgcac ctttttgtta aataaagaaa tgtatctaaa 9841 gttgcgtagt gatgtgctat tacctcttac gcaatataat agatacttag ctctttataa 9901 taagtacaag tattttagtg gagcaatgga tacaactagc tacagagaag ctgcttgttg 9961 tcatctcgca aaggctctca atgacttcag taactcaggt tctgatgttc tttaccaacc 10021 accacaaacc tctatcacct cagctgtttt gcagagtggt tttagaaaaa tggcattccc 10081 atctggtaaa gttgaggggt gtatggtaca agtaacttgt ggtacaacta cacttaacgg 10141 tctttggctt gatgacgtag tttactgtcc aagacatgtg atctgcacct ctgaagacat 10201 gcttaaccct aattatgaag atttactcat tcgtaagtct aatcataatt tcttggtaca 10261 ggctggtaat gttcaactca gggttattgg acattctatg caaaattgtg tacttaagct 10321 taaggttgat acagccaatc ctaagacacc taagtataag tttgttcgca ttcaaccagg 10381 acagactttt tcagtgttag cttgttacaa tggttcacca tctggtgttt accaatgtgc 10441 tatgaggccc aatttcacta ttaagggttc attccttaat ggttcatgtg gtagtgttgg 10501 ttttaacata gattatgact gtgtctcttt ttgttacatg caccatatgg aattaccaac 10561 tggagttcat gctggcacag acttagaagg taacttttat ggaccttttg ttgacaggca 10621 aacagcacaa gcagctggta cggcacaac tattacagtt aatgttttag cttggttgta 10681 cgctgctgtt ataaatggag acaggtggtt tctcaatcga tttaccacaa ctcttaatga 10741 ctttaacctt gtggctatga gtacaatta tgaacctcta acacaagacc atgttgacat 10801 actaggacct ctttctgctc aaactggaat tgccgtttta gatatgtgtg cttcattaaa
```

```
10861  agaattactg  caaaatggta  tgaatggacg  taccatattg  ggtagtgctt  tattagaaga 10921  tgaatttaca  ccttttgatg  ttgttagaca  atgctcaggt  gttactttcc  aaagtgcagt 10981  gaaaagaaca  atcaagggta  cacaccactg  gttgttactc  acaattttga  cttcactttt 11041  agttttagtc  cagagtactc  aatggtcttt  gttcttttt  ttgtatgaaa  atgccttttt 11101  accttttgct  atgggtatta  ttgctatgtc  tgcttttgca  atgatgtttg  tcaaacataa 11161  gcatgcattt  ctctgtttgt  ttttgttacc  ttctcttgcc  actgtagctt  attttaatat 11221  ggtctatatg  cctgctagtt  gggtgatgcg  tattatgaca  tggttggata  tggttgatac 11281  tagtttgtct  ggttttaagc  taaaagactg  tgttatgtat  gcatcagctg  tagtgttact 11341  aatccttatg  acagcaagaa  ctgtgtatga  tgatggtgct  aggagagtgt  ggacacttat 11401  gaatgtcttg  acactcgttt  ataaagttta  ttatggtaat  gctttagatc  aagccatttc 11461  catgtgggct  cttataatct  ctgttacttc  taactactca  ggtgtagtta  caactgtcat 11521  gttttttggcc  agaggtattg  tttttatgtg  tgttgagtat  tgccctattt  tcttcataac 11581  tggtaataca  cttcagtgta  taatgctagt  ttattgtttc  ttaggctatt  tttgtacttg 11641  ttactttggc  ctcttttgtt  tactcaaccg  ctactttaga  ctgactcttg  gtgtttatga 11701  ttacttagtt  tctacacagg  agtttagata  tatgaattca  cagggactac  tcccacccaa 11761  gaatagcata  gatgccttca  aactcaacat  taaattgttg  ggtgttggtg  gcaaaccttg 11821  tatcaaagta  gccactgtac  agtctaaaat  gtcagatgta  aagtgcacat  cagtagtctt 11881  actctcagtt  ttgcaacaac  tcagagtaga  atcatcatct  aaattgtggg  ctcaatgtgt 11941  ccagttacac  aatgacattc  tcttagctaa  agatactact  gaagcctttg  aaaaaatggt 12001  ttcactactt  tctgtttttgc  tttccatgca  gggtgctgta  gacataaaca  agctttgtga 12061  agaaatgctg  gacaacaggg  caaccttaca  agctatagcc  tcagagttta  gttcccttcc 12121  atcatatgca  gcttttgcta  ctgctcaaga  agcttatgag  caggctgttg  ctaatggtga 12181  ttctgaagtt  gttcttaaaa  agttgaagaa  gtctttgaat  gtggctaaat  ctgaatttga 12241  ccgtgatgca  gccatgcaac  gtaagttgga  aaagatggct  gatcaagcta  tgacccaaat 12301  gtataaacag  gctagatctg  aggacaagag  ggcaaaagtt  actagtgcta  tgcagacaat 12361  gcttttcact  atgcttagaa  agttggataa  tgatgcactc  aacaacatta  tcaacaatgc 12421  aagagatggt  tgtgttccct  tgaacataat  acctcttaca  acagcagcca  aactaatggt 12481  tgtcatacca  gactataaca  catataaaaa  tacgtgtgat  ggtacaacat  ttacttatgc 12541  atcagcattg  tgggaaatcc  aacaggttgt  agatgcagat  agtaaaattg  ttcaacttag 12601  tgaaattagt  atggacaatt  cacctaattt  agcatggcct  cttattgtaa  cagctttaag 12661  ggccaattct  gctgtcaaat  acagaataa  tgagcttagt  cctgttgcac  tacgacagat 12721  gtcttgtgct  gccggtacta  cacaaactgc  ttgcactgat  gacaatgcgt  tagcttacta 12781  caacacaaca  aagggaggta  ggtttgtact  tgcactgtta  tccgatttac  aggatttgaa 12841  atgggctaga  ttccctaaga  gtgatggaac  tggtactatc  tatacagaac  tggaaccacc 12901  ttgtaggttt  gttacagaca  cacctaaagg  tcctaaagtg  aagtatttat  actttattaa 12961  aggattaaac  aacctaaata  gaggtatggt  acttggtagt  ttagctgcca  cagtacgtct 13021  acaagctggt  aatgcaacag  aagtgcctgc  caattcaact  gtattatctt  tctgtgcttt 13081  tgctgtagat  gctgctaaag  cttacaaaga  ttatctagct  agtgggggac  aaccaatcac 13141  taattgtgtt  aagatgttgt  gtacacacac  tggtactggt  caggcaataa  cagttacacc 13201  ggaagccaat  atggatcaag  aatcctttgg  tggtgcatcg  tgttgtctgt  actgccgttg
```

-continued

```
13261  ccacatagat catccaaatc ctaaaggatt ttgtgactta aaaggtaagt atgtacaaat 13321  acctacaact tgtgctaatg accctgtggg ttttacactt aaaaacacag tctgtaccgt 13381  ctgcggtatg tggaaaggtt atggctgtag ttgtgatcaa ctccgcgaac ccatgcttca 13441  gtcagctgat gcacaatcgt ttttaaacgg gtttgcggtg taagtgcagc ccgtcttaca 13501  ccgtgcggca caggcactag tactgatgtc gtatacaggg cttttgacat ctacaatgat 13561  aaagtagctg gttttgctaa attcctaaaa actaattgtt gtcgcttcca agaaaaggac 13621  gaagatgaca atttaattga ttcttacttt gtagttaaga gacacacttt ctctaactac 13681  caacatgaag aaacaattta taatttactt aaggattgtc cagctgttgc taaacatgac 13741  ttctttaagt ttagaataga cggtgacatg gtaccacata tatcacgtca acgtcttact 13801  aaatacacaa tggcagacct cgtctatgct ttaaggcatt ttgatgaagg taattgtgac 13861  acattaaaag aaatacttgt cacatacaat tgttgtgatg atgattattt caataaaaag 13921  gactggtatg attttgtaga aaacccagat atattacgcg tatacgccaa cttaggtgaa 13981  cgtgtacgcc aagctttgtt aaaaacagta caattctgtg atgccatgcg aaatgctggt 14041  attgttggtg tactgacatt agataatcaa gatctcaatg gtaactggta tgatttcggt 14101  gatttcatac aaaccacgcc aggtagtgga gttcctgttg tagattctta ttattcattg 14161  ttaatgccta tattaacctt gaccagggct ttaactgcag agtcacatgt tgacactgac 14221  ttaacaaagc cttacattaa gtgggatttg ttaaaatatg acttcacgga agagaggtta 14281  aaactctttg accgttattt taaatattgg gatcagacat accacccaaa ttgtgttaac 14341  tgtttggatg acagatgcat tctgcattgt gcaaacttta atgttttatt ctctacagtg 14401  ttcccaccta caagttttgg accactagtg agaaaaatat ttgttgatgg tgttccattt 14461  gtagtttcaa ctggatacca cttcagagag ctaggtgttg tacataatca ggatgtaaac 14521  ttacatagct ctagacttag ttttaaggaa ttacttgtgt atgctgctga ccctgctatg 14581  cacgctgctt ctggtaatct attactagat aaacgcacta cgtgcttttc agtagctgca 14641  cttactaaca atgttgcttt tcaaactgtc aaacccggta attttaacaa agacttctat 14701  gactttgctg tgtctaaggg ttttctttaag gaaggaagtt ctgttgaatt aaaaacacttc 14761  ttctttgctc aggatggtaa tgctgctatc agcgattatg actactatcg ttataatcta 14821  ccaacaatgt gtgatatcag acaactacta tttgtagttg aagttgttga taagtacttt 14881  gattgttacg atggtggctg tattaatgct aaccaagtca tcgtcaacaa cctagacaaa 14941  tcagctggtt ttccatttaa taaatggggt aaggctagac tttattatga ttcaatgagt 15001  tatgaggatc aagatgcact tttcgcatat acaaaacgta atgtcatccc tactataact 15061  caaatgaatc ttaagtatgc cattagtgca aagaatagag ctcgcaccgt agctggtgtc 15121  tctatctgta gtactatgac caatagacag tttcatcaaa aattattgaa atcaatagcc 15181  gccactagag gagctactgt agtaattgga acaagcaaat ctatgtggtgg ttggcacaac 15241  atgttaaaaa ctgttttatag tgatgtagaa aaccctcacc ttatgggttg ggattatcct 15301  aaatgtgata gagccatgcc taacatgctt agaattatgg cctcacttgt tcttgctcgc 15361  aaacatacaa cgtgttgtag cttgtcacac cgtttctata gattagctaa tgagtgtgct 15421  caagtattga gtgaaatggt catgtgtggc ggttcactat atgttaaacc aggtggaacc 15481  tcatcaggag atgccacaac tgcttatgct aatagtgttt ttaacatttg tcaagctgtc 15541  acggccaatg ttaatgcact tttatctact gatggtaaca aaattgccga taagtatgtc 15601  cgcaatttac aacacagact ttatgagtgt ctctatagaa atagagatgt tgacacagac 15661  tttgtgaatg agttttacgc atatttgcgt aaacatttct caatgatgat actctctgac
```

```
15721  gatgctgttg tgtgtttcaa tagcacttat gcatctcaag gtctagtggc tagcataaag 15781  aactttaagt cagttcttta ttatcaaaac aatgttttta tgtctgaagc aaaatgttgg 15841  actgagactg accttactaa aggacctcat gaattttgct ctcaacatac aatgctagtt 15901  aaacagggtg atgattatgt gtaccttcct tacccagatc catcaagaat cctaggggcc 15961  ggctgttttg tagatgatat cgtaaaaaca gatggtacac ttatgattga acggttcgtg 16021  tctttagcta tagatgctta cccacttact aaacatccta atcaggagta tgctgatgtc 16081  tttcatttgt acttacaata cataagaaag ctacatgatg agttaacagg acacatgtta 16141  gacatgtatt ctgttatgct tactaatgat aacacttcaa ggtattggga acctgagttt 16201  tatgaggcta tgtacacacc gcatacagtc ttacaggctg ttggggcttg tgttctttgc 16261  aattcacaga cttcattaag atgtggtgct tgcatacgta gaccattctt atgttgtaaa 16321  tgctgttacg accatgtcat atcaacatca cataaattag tcttgtctgt taatccgtat 16381  gtttgcaatg ctccaggttg tgatgtcaca gatgtgactc aactttactt aggaggtatg 16441  agctattatt gtaaatcaca taaaccaccc attagttttc cattgtgtgc taatggacaa 16501  gttttttggtt tatataaaaa tacatgtgtt ggtagcgata atgttactga ctttaatgca 16561  attgcaacat gtgactggac aaatgctggt gattacattt tagctaacac ctgtactgaa 16621  agactcaagc tttttgcagc agaaacgctc aaagctactg aggagacatt taaactgtct 16681  tatggtattg ctactgtacg tgaagtgctg tctgacagag aattacatct ttcatgggaa 16741  gttggtaaac ctagaccacc acttaaccga aattatgtct ttactggtta tcgtgtaact 16801  aaaaacagta agtacaaat aggagagtac acctttgaaa aaggtgacta tggtgatgct 16861  gttgtttacc gaggtacaac aacttacaaa ttaaatgttg gtgattattt tgtgctgaca 16921  tcacatacag taatgccatt aagtgcacct acactagtgc cacaagagca ctatgttaga 16981  attactggct tatacccaac actcaatatc tcagatgagt tttctagcaa tgttgcaaat 17041  tatcaaaagg ttggtatgca aaagtattct acactccagg gaccacctgg tactggtaag 17101  agtcattttg ctattggcct agctctctac taccccttctg ctcgcatagt gtatacagct 17161  tgctctcatg ccgctgttga tgcactatgt gagaaggcat taaaatattt gcctatagat 17221  aaatgtagta gaattatacc tgcacgtgct cgtgtagagt gttttgataa attcaaagtg 17281  aattcaacat tagaacagta tgtcttttgt actgtaaatg cattgcctga cgacagca 17341  gatatagttg tctttgatga aatttcaatg gccacaaatt atgatttgag tgttgtcaat 17401  gccagattac gtgctaagca ctatgtgtac attggcgacc ctgctcaatt acctgcacca 17461  cgcacattgc taactaaggg cacactagaa ccagaatatt tcaattcagt gtgtagactt 17521  atgaaaacta taggtccaga catgttcctc ggaacttgtc ggcgttgtcc tgctgaaatt 17581  gttgacactg tgagtgcttt ggtttatgat aataagctta aagcacataa agacaaatca 17641  gctcaatgct ttaaaatgtt ttataagggt gttatcacgc atgatgtttc atctgcaatt 17701  aacaggccac aaataggcgt ggtaagagaa ttccttacac gtaaccctgc ttggagaaaa 17761  gctgtcttta tttcacctta taattcacag aatgctgtag cctcaaagat tttgggacta 17821  ccaactcaaa ctgttgattc atcacagggc tcagaatatg actatgtcat attcactcaa 17881  accactgaaa cagctcactc ttgtaatgta aacagattta atgttgctat taccagagca 17941  aaagtaggca cactttgcat aatgtctgat agagaccttt atgacaagtt gcaatttaca 18001  agtcttgaaa ttccacgtag gaatgtggca actttacaag ctgaaaatgt aacaggactc 18061  tttaaagatt gtagtaaggt aatcactggg ttacatccta cacaggcacc tacacacctc
```

-continued

```
18121  agtgttgaca ctaaattcaa aactgaaggt ttatgtgttg acatacctgg catacctaag 18181  gacatgacct atagaagact catctctatg atgggtttta aaatgaatta tcaagttaat 18241  ggttaccota acatgtttat cacccgcgaa gaagctataa gacatgtacg tgcatggatt 18301  ggcttcgatg tcgagggggtg tcatgctact agagaagctg ttggtaccaa tttacctta 18361  cagctaggtt tttctacagg tgttaaccta gttgctgtac ctacaggtta tgttgataca 18421  cctaataata cagattttt cagagttagt gctaaaccac cgcctggaga tcaatttaaa 18481  cacctcatac cacttatgta caaaggactt ccttggaatg tagtgcgtat aaagattgta 18541  caaatgttaa gtgacacact taaaaatctc tctgacagag tcgtatttgt cttatgggca 18601  catggctttg agttgacatc tatgaagtat tttgtgaaaa taggacctga gcgcacctgt 18661  tgtctatgtg atagacgtgc cacatgcttt tccactgctt cagacactta tgcctgttgg 18721  catcattcta ttggatttga ttacgtctat aatccgttta tgattgatgt tcaacaatgg 18781  ggttttacag gtaacctaca aagcaaccat gatctgtatt gtcaagtcca tggtaatgca 18841  catgtagcta gttgtgatgc aatcatgact aggtgtctag ctgtccacga gtgctttgtt 18901  aagcgtgttg actggactat tgaatatcct ataattggtg atgaactgaa gattaatgcg 18961  gcttgtagaa aggttcaaca catggttgtt aaagctgcat tattagcaga caaattccca 19021  gttcttcacg acattggtaa ccctaaagct attaagtgtg tacctcaagc tgatgtagaa 19081  tggaagttct atgatgcaca gccttgtagt gacaaagctt ataaaataga agaattattc 19141  tattcttatg ccacacattc tgacaaattc acagatggtg tatgcctatt ttggaattgc 19201  aatgtcgata gatatcctgc taattccatt gtttgtagat ttgacactag agtgctatct 19261  aaccttaact tgcctggttg tgatggtggc agtttgtatg taaataaaca tgcattccac 19321  acaccagctt ttgataaaag tgcttttgtt aatttaaaac aattaccatt tttctattac 19381  tctgacagtc catgtgagtc tcatggaaaa caagtagtgt cagatataga ttatgtacca 19441  ctaaagtctg ctacgtgtat aacacgttgc aatttaggtg gtgctgtctg tagacatcat 19501  gctaatgagt acagattgta tctcgatgct tataacatga tgatctcagc tggctttagc 19561  ttgtgggttt acaaacaatt tgatacttat aacctctgga cactttttac aagacttcag 19621  agtttagaaa atgtggcttt taatgttgta aataagggac actttgatgg acaacagggt 19681  gaagtaccag tttctatcat taataacact gtttacacaa aagttgatgg tgttgatgta 19741  gaattgtttg aaaataaaac aacattacct gttaatgtag catttgagct ttgggctaag 19801  cgcaacatta aaccagtacc agaggtgaaa atactcaata atttgggtgt ggacattgct 19861  gctaatactg tgatctggga ctacaaaaga gatgctccag cacatatatc tactattggt 19921  gtttgttcta tgactgacat agccaagaaa ccaactgaaa cgatttgtgc accactcact 19981  gtcttttttg atggtagagt tgatggtcaa gtagacttat ttagaaatgc ccgtaatggt 20041  gttcttatta cagaaggtag tgttaaaggt ttacaaccat ctgtaggtcc caaacaagct 20101  agtcttaatg gagtcacatt aattggagaa gccgtaaaaa cacagttcaa ttattataag 20161  aaagttgatg gtgttgtcca acaattacct gaaacttact ttactcagag tagaaattta 20221  caagaattta aacccaggag tcaaatggaa attgatttct tagaattagc tatggatgaa 20281  ttcattgaac ggtataaatt agaaggctat gccttcgaac atatcgttta tggagatttt 20341  agtcatagtc agttaggtgg tttacatcta ctgattggac tagctaaacg ttttaaggaa 20401  tcacctttg aattagaaga tttttattcct atggacagta cagttaaaaa ctatttcata 20461  acagatgcgc aaacaggttc atctaagtgt gtgtgttctg ttattgattt attacttgat 20521  gattttgttg aaataataaa atcccaagat ttatctgtag tttctaaggt tgtcaaagtg
```

-continued

```
20581  actattgact atacagaaat ttcatttatg ctttggtgta aagatggcca tgtagaaaca 20641  ttttacccaa aattacaatc tagtcaagcg tggcaaccgg gtgttgctat gcctaatctt 20701  tacaaatgc aaagaatgct attagaaaag tgtgaccttc aaaattatgg tgatagtgca 20761  acattaccta aaggcataat gatgaatgtc gcaaaatata ctcaactgtg tcaatattta 20821  aacacattaa cattagctgt accctataat atgagagtta tacattttgg tgctggttct 20881  gataaaggag ttgcaccagg tacagctgtt ttaagacagt ggttgcctac gggtacgctg 20941  cttgtcgatt cagatcttaa tgactttgtc tctgatgcag attcaacttt gattggtgat 21001  tgtgcaactg tacatacagc taataaatgg gatctcatta ttagtgatat gtacgaccct 21061  aagactaaaa atgttacaaa agaaaatgac tctaaagagg gttttttcac ttacatttgt 21121  gggtttatac aacaaaagct agctcttgga ggttccgtgg ctataaagat aacagaacat 21181  tcttggaatg ctgatcttta taagctcatg ggacacttcg catggtggac agcctttgtt 21241  actaatgtga atgcgtcatc atctgaagca ttttttaattg gatgtaatta tcttggcaaa 21301  ccacgcgaac aaatagatgg ttatgtcat catgcaaatt acatattttg gaggaataca 21361  aatccaattc agttgtcttc ctattcttta tttgacatga gtaaatttcc ccttaaatta 21421  aggggtactg ctgttatgtc tttaaaagaa ggtcaaatca atgatatgat tttatctctt 21481  cttagtaaag gtagacttat aattagagaa aacaacagag ttgttatttc tagtgatgtt 21541  cttgttaaca actaaacgaa caatgtttgt ttttcttgtt ttattgccac tagtctctag 21601  tcagtgtgtt aatcttacaa ccagaactca attaccccct gcatacacta attctttcac 21661  acgtggtgtt tattaccctg acaaagtttt cagatcctca gttttacatt caactcagga 21721  cttgttctta cctttctttt ccaatgttac ttggttccat gctatacatg tctctgggac 21781  caatggtact aagaggtttg ataaccctgt cctaccattt aatgatggtg tttattttgc 21841  ttccactgag aagtctaaca taataagagg ctggattttt ggtactactt tagattcgaa 21901  gacccagtcc ctacttattg ttaataacgc tactaatgtt gttattaaag tctgtgaatt 21961  tcaattttgt aatgatccat ttttgggtgt ttattaccac aaaaacaaca aaagttggat 22021  ggaaagtgag ttcagagttt attctagtgc gaataattgc acttttgaat atgtctctca 22081  gccttttctt atggaccttg aaggaaaaca gggtaatttc aaaaatctta gggaatttgt 22141  gtttaagaat attgatggtt attttaaaat atattctaag cacacgccta ttaatttagt 22201  gcgtgatctc cctcagggtt tttcggcttt agaaccattg gtagatttgc aataggtat 22261  taacatcact aggtttcaaa ctttacttgc tttacataga agttatttga ctcctggtga 22321  ttcttcttca ggttggacag ctggtgctgc agcttattat gtgggttatc ttcaacctag 22381  gacttttcta ttaaaatata tgaaaatgg aaccattaca gatgctgtag actgtgcact 22441  tgaccctctc tcagaaacaa agtgtacgtt gaaatccttc actgtagaaa aaggaatcta 22501  tcaaacttct aactttagag tccaaccaac agaatctatt gttagatttc ctaatattac 22561  aaacttgtgc ccttttggtg aagtttttaa cgccaccaga tttgcatctg tttatgcttg 22621  gaacaggaag agaatcagca actgtgttgc tgattattct gtcctatata attccgcatc 22681  attttccact tttaagtgtt atggagtgtc tcctactaaa ttaaatgatc tctgctttac 22741  taatgtctat gcagattcat ttgtaattag aggtgatgaa gtcagacaaa tcgctccagg 22801  gcaaactgga aagattgctg attataatta taaattacca gatgatttta caggctgcgt 22861  tatagcttgg aattctaaca atcttgattc taaggttggt ggtaattata attacctgta 22921  tagattgttt aggaagtcta atctcaaacc ttttgagaga gatatttcaa ctgaaatcta
```

-continued

```
22981 tcaggccggt agcacacctt gtaatggtgt tgaaggtttt aattgttact ttcctttaca 23041 atcatatggt ttccaaccca ctaatggtgt tggttaccaa ccatacagag tagtagtact 23101 ttcttttgaa cttctacatg caccagcaac tgtttgtgga cctaaaaagt ctactaattt 23161 ggttaaaaac aaatgtgtca atttcaactt caatggttta acaggcacag gtgttcttac 23221 tgagtctaac aaaaagtttc tgcctttcca acaatttggc agagacattg ctgacactac 23281 tgatgctgtc cgtgatccac agacacttga gattcttgac attacaccat gttcttttgg 23341 tggtgtcagt gttataacac caggaacaaa tacttctaac caggttgctg ttctttatca 23401 ggatgttaac tgcacagaag tccctgttgc tattcatgca gatcaactta ctcctacttg 23461 gcgtgtttat tctacaggtt ctaatgtttt tcaaacacgt gcaggctgtt taataggggc 23521 tgaacatgtc aacaactcat atgagtgtga catacccatt ggtgcaggta tatgcgctag 23581 ttatcagact cagactaatt ctcctcggcg ggcacgtagt gtagctagtc aatccatcat 23641 tgcctacact atgtcacttg gtgcagaaaa ttcagttgct tactctaata actctattgc 23701 catacccaca aattttacta ttagtgttac cacagaaatt ctaccagtgt ctatgaccaa 23761 gacatcagta gattgtacaa tgtacatttg tggtgattca actgaatgca gcaatctttt 23821 gttgcaatat ggcagttttt gtacacaatt aaaccgtgct ttaactggaa tagctgttga 23881 acaagacaaa aacacccaag aagtttttgc acaagtcaaa caaatttaca aaacaccacc 23941 aattaaagat tttggtggtt ttaatttttc acaaatatta ccagatccat caaaaccaag 24001 caagaggtca tttattgaag atctactttt caacaaagtg acacttgcag atgctggctt 24061 catcaaacaa tatggtgatt gccttggtga tattgctgct agagacctca tttgtgcaca 24121 aaagtttaac ggccttactg ttttgccacc tttgctcaca gatgaaatga ttgctcaata 24181 cacttctgca ctgttagcgg gtacaatcac ttctggttgg acctttggtc aggtgctgc 24241 attacaaata ccatttgcta tgcaaatggc ttataggttt aatggtattg gagttacaca 24301 gaatgttctc tatgagaacc aaaaattgat tgccaaccaa tttaatagtg ctattggcaa 24361 aattcaagac tcactttctt ccacagcaag tgcacttgga aaacttcaag atgtggtcaa 24421 ccaaaatgca caagctttaa acacgcttgt taaacaactt agctccaatt ttggtgcaat 24481 ttcaagtgtt ttaaatgata tcctttcacg tcttgacaaa gttgaggctg aagtgcaaat 24541 tgataggttg atcacaggca gacttcaaag tttgcagaca tatgtgactc aacaattaat 24601 tagagctgca gaaatcagag cttctgctaa tcttgctgct actaaaatgt cagagtgtgt 24661 acttggacaa tcaaaaagag ttgattttg tggaaagggc tatcatctta tgtccttccc 24721 tcagtcagca cctcatggtg tagtcttctt gcatgtgact tatgtccctg cacaagaaaa 24781 gaacttcaca actgctcctg ccatttgtca tgatggaaaa gcacactttc ctcgtgaagg 24841 tgtctttgtt tcaaatggca cacactggtt tgtaacacaa aggaattttt atgaaccaca 24901 aatcattact acagacaaca catttgtgtc tggtaactgt gatgttgtaa taggaattgt 24961 caacaacaca gtttatgatc ctttgcaacc tgaattagac tcattcaagg aggagttaga 25021 taaatatttt aagaatcata tcaccagga tgttgattta ggtgacatct ctggcattaa 25081 tgcttcagtt gtaaacattc aaaaagaaat tgaccgcctc aatgaggttg ccaagaattt 25141 aaatgaatct ctcatcgatc tccaagaact tggaaagtat gagcagtata taaaatggcc 25201 atggtacatt tggctaggtt ttatagctgg cttgattgcc atagtaatgg tgacaattat 25261 gctttgctgt atgaccagtt gctgtagttg tctcaagggc tgttgttctt gtggatcctg 25321 ctgcaaattt gatgaagacg actctgagcc agtgctcaaa ggagtcaaat tacattacac 25381 ataaacgaac ttatggattt gtttatgaga atcttcacaa ttggaactgt aactttgaag
```

-continued

```
25441  caaggtgaaa tcaaggatgc tactccttca gattttgttc gcgctactgc aacgataccg 25501  atacaagcct cactcccttt cggatggctt attgttggcg ttgcacttct tgctgttttt 25561  cagagcgctt ccaaaatcat aaccctcaaa aagagatggc aactagcact ctccaagggt 25621  gttcactttg tttgcaactt gctgttgttg tttgtaacag tttactcaca ccttttgctc 25681  gttgctgctg gccttgaagc ccctttttctc tatctttatg ctttagtcta cttcttgcag 25741  agtataaact ttgtaagaat aataatgagg ctttggcttt gctggaaatg ccgttccaaa 25801  aacccattac tttatgatgc caactatttt cttttgctggc atactaattg ttacgactat 25861  tgtatacctt acaatagtgt aacttcttca attgtcatta cttcaggtga tggcacaaca 25921  agtcctattt ctgaacatga ctaccagatt ggtggttata ctgaaaaatg ggaatctgga 25981  gtaaaagact gtgttgtatt acacagttac ttcacttcag actattacca gctgtactca 26041  actcaattga gtacagacac tggtgttgaa catgttacct tcttcatcta caataaaatt 26101  gttgatgagc ctgaagaaca tgtccaaatt cacacaatcg acggttcatc cggagttgtt 26161  aatccagtaa tggaaccaat ttatgatgaa ccgacgacga ctactagcgt gcctttgtaa 26221  gcacaagctg atgagtacga acttatgtac tcattcgttt cggaagagac aggtacgtta 26281  atagttaata gcgtacttct ttttcttgct ttcgtggtat tcttgctagt tacactagcc 26341  atccttactg cgcttcgatt gtgtgcgtac tgctgcaata ttgttaacgt gagtcttgta 26401  aaaccttctt tttacgttta ctctcgtgtt aaaaatctga attcttctag agttcctgat 26461  cttctggtct aaacgaacta aatattatat tagttttttct gtttggaact ttaattttag 26521  ccatggcaga ttccaacggt actattaccg ttgaagagct aaaaaagctc cttgaacaat 26581  ggaacctagt aataggtttc ctattcctta catggatttg tcttctacaa tttgcctatg 26641  ccaacaggaa taggtttttg tatataatta agttaatttt cctctggctg ttatggccag 26701  taactttagc ttgtttttgtg cttgctgctg tttacagaat aaattggatc accggtggaa 26761  ttgctatcgc aatggcttgt cttgtaggct tgatgtggct cagctacttc attgcttctt 26821  tcagactgtt tgcgcgtacg cgttccatgt ggtcattcaa tccagaaact aacattcttc 26881  tcaacgtgcc actccatggc actattctga ccagaccgct tctagaaagt gaactcgtaa 26941  tcggagctgt gatccttcgt ggacatcttc gtattgctgg acaccatcta ggacgctgtg 27001  acatcaagga cctgcctaaa gaaatcactg ttgctacatc acgaacgctt tcttattaca 27061  aattgggagc ttcgcagcgt gtagcaggtg actcaggttt tgctgcatac agtcgctaca 27121  ggattggcaa ctataaatta aacacagacc attccagtag cagtgacaat attgctttgc 27181  ttgtacagta agtgacaaca gatgtttcat ctcgttgact ttcaggttac tatagcagag 27241  atattactaa ttattatgag gactttttaaa gttccatttt ggaatcttga ttacatcata 27301  aacctcataa ttaaaaattt atctaagtca ctaactgaga ataaatattc tcaattagat 27361  gaagagcaac caatggagat tgattaaacg aacatgaaaa ttattctttt cttggcactg 27421  ataacactcg ctacttgtga gctttatcac taccaagagt gtgttagagg tacaacagta 27481  ctttttaaaag aaccttgctc ttctggaaca tacgagggca attcaccatt tcatcctcta 27541  gctgataaca aatttgcact gacttgcttt agcactcaat ttgcttttgc ttgtcctgac 27601  ggcgtaaaac acgtctatca gttacgtgcc agatcagttt cacctaaact gttcatcaga 27661  caagaggaag ttcaagaact ttactctcca attttttctta ttgttgcggc aatagtgttt 27721  ataacacttt gcttcacact caaaagaaag acagaatgat tgaactttca ttaattgact 27781  tctatttgtg cttttttagcc tttctgctat tccttgtttt aattatgctt attatctttt
```

```
27841 ggttctcact tgaactgcaa gatcataatg aaacttgtca cgcctaaacg aacatgaaat 27901 ttcttgtttt cttaggaatc atcacaactg tagctgcatt tcaccaagaa tgtagtttac 27961 agtcatgtac tcaacatcaa ccatatgtag ttgatgaccc gtgtcctatt cacttctatt 28021 ctaaatggta tattagagta ggagctagaa aatcagcacc tttaattgaa ttgtgcgtgg 28081 atgaggctgg ttctaaatca cccattcagt acatcgatat cggtaattat acagtttcct 28141 gtttaccttt tacaattaat tgccaggaac ctaaattggg tagtcttgta gtgcgttgtt 28201 cgttctatga agacttttta gagtatcatg acgttcgtgt tgttttagat ttcatctaaa 28261 cgaacaaact aaaatgtctg ataatggacc ccaaaatcag cgaaatgcac cccgcattac 28321 gtttggtgga ccctcagatt caactggcag taaccagaat ggagaacgca gtggggcgcg 28381 atcaaaacaa cgtcggcccc aaggtttacc caataatact gcgtcttggt tcaccgctct 28441 cactcaacat ggcaaggaag accttaaatt ccctcgagga caaggcgttc aattaacac 28501 caatagcagt ccagatgacc aaattggcta ctaccgaaga gctaccagac gaattcgtgg 28561 tggtgacggt aaaatgaaag atctcagtcc aagatggtat ttctactacc taggaactgg 28621 gccagaagct ggacttccct atggtgctaa caaagacggc atcatatggg ttgcaactga 28681 gggagccttg aatacaccaa aagatcacat tggcacccgc aatcctgcta caaatgctgc 28741 aatcgtgcta caacttcctc aaggaacaac attgccaaaa ggcttctacg cagaagggag 28801 cagaggcggc agtcaagcct cttctcgttc ctcatcacgt agtcgcaaca gttcaagaaa 28861 ttcaactcca ggcagcagta ggggaacttc tcctgctaga atggctggca atggcggtga 28921 tgctgctctt gctttgctgc tgcttgacag attgaaccag cttgagagca aaatgtctgg 28981 taaaggccaa caacaacaag gccaaactgt cactaagaaa tctgctgctg aggcttctaa 29041 gaagcctcgg caaaaacgta ctgccactaa agcatacaat gtaacacaag ctttcggcag 29101 acgtggtcca gaacaaaccc aaggaaattt tggggaccag gaactaatca gacaaggaac 29161 tgattacaaa cattggccgc aaattgcaca atttgccccc agcgcttcag cgttcttcgg 29221 aatgtcgcgc attggcatgg aagtcacacc ttcgggaacg tggttgacct acacaggtgc 29281 catcaaattg gatgacaaag atccaaattt caaagatcaa gtcattttgc tgaataagca 29341 tattgacgca tacaaaacat tcccaccaac agagcctaaa aaggacaaaa agaagaaggc 29401 tgatgaaact caagccttac cgcagagaca gaagaaacag caaactgtga ctcttcttcc 29461 tgctgcagat ttggatgatt tctccaaaca attgcaacaa tccatgagca gtgctgactc 29521 aactcaggcc taaactcatg cagaccacac aaggcagatg ggctatataa acgttttcgc 29581 ttttccgttt acgatatata gtctactctt gtgcagaatg aattctcgta actacatagc 29641 acaagtagat gtagttaact ttaatctcac atagcaatct ttaatcagtg tgtaacatta 29701 gggaggactt gaaagagcca ccacattttc accgaggcca cgcggagtac gatcgagtgt 29761 acagtgaaca atgctaggga gagctgccta tatggaagag ccctaatgtg taaaattaat 29821 tttagtagtg ctatccccat gtgattttaa tagcttctta ggagaatgac aaaaaaaaaa 29881 aaaaaaaaaa aaaaaaaaaa aaa
```

General Definitions

The following definitions are included for the purpose of understanding the present subject matter and for constructing the appended patent claims. The abbreviations used herein have their conventional meanings within the chemical and biological arts.

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, NY 1994): Sambrook et al., MOLECULAR CLONING, A LABORATORY MANUAL, Cold Springs Harbor Press (Cold Springs Harbor, NY 1989). Any methods, devices and materials similar or equivalent to those described herein can be used in the practice of this invention. The following definitions are provided to facilitate understanding of certain terms used frequently herein and are not meant to limit the scope of the present disclosure.

The term "disease" refers to any deviation from the normal health of a mammal and includes a state when disease symptoms are present, as well as conditions in which a deviation (e.g., SARS-COV2) has occurred, but symptoms are not yet manifested.

A viral infection, as used herein, may refer to a coronavirus (for example, SARS-COV2), hepatitis virus infection, an influenza virus infection, a herpes simplex virus infection, an enterovirus infection, a rotavirus infection, a dengue virus infection, a poxvirus infection, a human immunodeficiency virus infection, an adenovirus infection, a coronavirus infection, an arenavirus infection, a measles virus infection, a retrovirus infection or a Norovirus infection.

As used herein, the term "engineered immune cell" refers to an immune cell (e.g., T cell, NK cell, NKT cell, B cell, dendritic cell, myeloid cell, etc.) that is genetically modified. The term "chimeric antigen receptor" ("CAR") refers to a recombinant polypeptide construct comprising at least an extracellular antigen binding domain and a transmembrane domain. Upon binding to their target (e.g., virus-infected cells), CARs typically modify the immune response of the immune cells on which they are displayed.

As used herein, an "immune response" refers to the action of a cell of the immune system (e.g., T lymphocytes, B lymphocytes, natural killer (NK) cells, macrophages, cosinophils, mast cells, dendritic cells, neutrophils, etc.) and soluble macromolecules produced by any of these cells or the liver (e.g., antibodies, cytokines, and complement) that results in selective targeting, binding to, damage to, destruction of, and/or elimination from a subject of invading pathogens (e.g., viruses), cells or tissues infected with pathogens, or cancerous cells or other abnormal/diseased-associated cells.

A "lectin" is a carbohydrate-binding protein which is widely found in nature, particularly plants. Lectins are highly specific for sugar moieties of other molecules and mediate attachment and binding of bacteria and viruses to target molecules in cells. Lectins have been used in many aspects of glycobiology (Andre' et al., Molecules, 20:1788-1823 (2015): Gabius et al., Trends Biochem. Sci., 36 (6): 298-313 (2011), and Gabius et al., Trends Biochem. Sci., 40:360-376 (2015)), including as potential antiviral agents.

"Patient" or "subject in need thereof" refers to a living member of the animal kingdom suffering from or who may suffer from the indicated disorder. In embodiments, the subject is a member of a species comprising individuals who may naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human.

As used herein, the engineered immune cell is a natural killer (NK) cell. NK cells are a type of cytotoxic lymphocyte that plays a role in the innate immune system. NK cells are defined as large granular lymphocytes and constitute the third kind of cells differentiated from the common lymphoid progenitor which also gives rise to B and T lymphocytes (see, e.g., Immunobiology, 5th ed., Janeway et al., eds., Garland Publishing, New York, N.Y. (2001)). NK cells differentiate and mature in the bone marrow, lymph node, spleen, tonsils, and thymus. Following maturation, NK cells enter into the circulation as large lymphocytes with distinctive cytotoxic granules. NK cells are able to recognize and kill some abnormal cells, such as, for example, some tumor cells and virus-infected cells, and are thought to be important in the innate immune defense against intracellular pathogens. With respect to T cells, the NK cell can be a cultured NK cell or an NK cell obtained directly from a mammal. If obtained from a mammal, the NK cell can be obtained from numerous sources, including but not limited to blood, bone marrow, lymph node, the thymus, or other tissues or fluids. NK cells can also be enriched for or purified. The NK cell desirably is a human NK cell. NK cell lines are available from, e.g., the American Type Culture Collection (ATCC, Manassas, Va.) and include, for example, NK-92 cells (ATCC CRL-2407), NK92MI cells (ATCC CRL-2408), and derivatives thereof.

When T cells or NK cells are administered to a mammal, the cells can be allogeneic or autologous to the mammal. In "autologous" administration methods, cells (e.g., immune cells (lymphocytes))) are removed from a mammal, stored, engineered or modified (as described herein) and returned back to the same mammal. In "allogeneic" administration methods, a mammal receives cells (e.g., blood-forming stem cells or lymphocytes) from a genetically similar, but not identical, donor.

The terms "subject," "patient," "individual," etc. are not intended to be limiting and can be generally interchanged. That is, an individual described as a "patient" does not necessarily have a given disease but may be merely seeking medical advice.

The transitional term "comprising." which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

In the descriptions herein and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B:"

"one or more of A and B:" and "A and/or B" are each intended to mean "A alone, B alone, or A and B together." A similar interpretation is also intended for lists including three or more items. For example, the phrases "at least one of A, B, and C:" "one or more of A, B, and C:" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

It is understood that where a parameter range is provided, all integers within that range, and tenths thereof, are also provided by the invention. For example, "0.2-5 mg" is a disclosure of 0.2 mg, 0.3 mg, 0.4 mg. 0.5 mg. 0.6 mg etc. up to and including 5.0 mg.

As used in the description herein and throughout the claims that follow, the meaning of "a." "an," and "the" includes plural reference unless the context clearly dictates otherwise.

As used herein, "treating" or "treatment" of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean inhibiting the progression of the condition, disorder or disease, slowing the progression of the condition, disorder or disease temporarily, although in some instances, it involves halting the progression of the condition, disorder or disease permanently.

As used herein, the terms "treat" and "prevent" are not intended to be absolute terms. In various embodiments, treatment can refer to a 10%, 20%, 30%, 40%, 50%, 60%, 70%, 80%, 90%, or 100% reduction in the severity of an established disease, condition, or symptom of the disease or condition. In embodiments, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. In embodiments, references to decreasing, reducing, or inhibiting include a change of 10%, 20%, 30%, 40%, 50%, 60%, 70%, 80%, 90% or greater as compared to a control level and such terms can include but do not necessarily include complete elimination. In embodiments, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques.

The terms "effective amount," "effective dose," etc. refer to the amount of an agent that is sufficient to achieve a desired effect, as described herein. In embodiments, the term "effective" when referring to an amount of cells or a therapeutic compound may refer to a quantity of the cells or the compound that is sufficient to yield an improvement or a desired therapeutic response without undue adverse side effects (such as toxicity, irritation, or allergic response) commensurate with a reasonable benefit/risk ratio when used in the manner of this disclosure. In embodiments, the term "effective" when referring to the generation of a desired cell population may refer to an amount of one or more compounds that is sufficient to result in or promote the production of members of the desired cell population, especially compared to culture conditions that lack the one or more compounds.

As used herein, an "isolated" or "purified" nucleic acid molecule, polynucleotide, polypeptide, or protein, is substantially free of other cellular material, or culture medium when produced by recombinant techniques, or chemical precursors or other chemicals when chemically synthesized. Purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis. A purified or isolated polynucleotide (RNA or DNA) is free of the genes or sequences that flank it in its naturally-occurring state. Purified also defines a degree of sterility that is safe for administration to a human subject, e.g., lacking infectious or toxic agents.

Similarly, by "substantially pure" is meant a nucleotide or polypeptide that has been separated from the components that naturally accompany it. Typically, the nucleotides and polypeptides are substantially pure when they are at least 60%, 70%, 80%, 90%, 95%, or even 99%, by weight, free from the proteins and naturally-occurring organic molecules with they are naturally associated. A purified or isolated polynucleotide (ribonucleic acid (RNA) or deoxyribonucleic acid (DNA)) is free of the genes or sequences that flank it in its natural-occurring state. A purified or isolated polypeptide is free of the amino acids or sequences that flank it in its naturally-occurring state. Purified also defines a degree of sterility that is safe for administration to a human subject, e.g., lacking infectious or toxic agents. In the case of tumor antigens, the antigen may be purified or a processed preparation such as a tumor cell lysate.

A "control" sample or value refers to a sample that serves as a reference, usually a known reference, for comparison to a test sample. For example, a test sample can be taken from a test subject, e.g., a subject with a coronavirus (e.g., SARS-COV2), and compared to samples from known conditions, e.g., a subject (or subjects) that does not have a coronavirus (e.g., SARS-COV2) (a negative or normal control), or a subject (or subjects) who does have a coronavirus (e.g., SARS-COV2) (positive control). A control can also represent an average value gathered from a number of tests or results. One of skill in the art will recognize that controls can be designed for assessment of any number of parameters. One of skill in the art will understand which controls are valuable in a given situation and be able to analyze data based on comparisons to control values. Controls are also valuable for determining the significance of data. For example, if values for a given parameter are variable in controls, variation in test samples will not be considered as significant.

The term, "normal amount" with respect to a compound (e.g., a protein or mRNA) refers to a normal amount of the compound in an individual who does not have a coronavirus (e.g., SARS-COV2) in a healthy or general population. The amount of a compound can be measured in a test sample and compared to the "normal control" level, utilizing techniques such as reference limits, discrimination limits, or risk defining thresholds to define cutoff points and abnormal values (e.g., for a coronavirus (e.g., SARS-COV2) or a symptom thereof). The normal control level means the level of one or more compounds or combined compounds typically found in a subject known not suffering from a coronavirus (e.g., SARS-COV2). Such normal control levels and cutoff points may vary based on whether a compound is used alone or in a formula combining with other compounds into an index. Alternatively, the normal control level can be a database of compounds patterns from previously tested subjects who did not develop a coronavirus (e.g., SARS-COV2) or a particular symptom thereof (e.g., in the event the coronavirus (e.g., SARS-COV2) develops or a subject already having a coronavirus (e.g., SARS-COV2) is tested) over a clinically relevant time horizon.

The level that is determined may be the same as a control level or a cut off level or a threshold level or may be increased or decreased relative to a control level or a cut off level or a threshold level. In some aspects, the control subject is a matched control of the same species, gender, ethnicity, age group, smoking status, body mass index (BMI), current therapeutic regimen status, medical history, or a combination thereof, but differs from the subject being diagnosed in that the control does not suffer from the disease (or a symptom thereof) in question or is not at risk for the disease.

Relative to a control level, the level that is determined may an increased level. As used herein, the term "increased" with respect to level (e.g., protein or mRNA level) refers to any % increase above a control level. In various embodiments, the increased level may be at least or about a 5% increase, at least or about a 10% increase, at least or about a 15% increase, at least or about a 20% increase, at least or about a 25% increase, at least or about a 30% increase, at least or about a 35% increase, at least or about a 40% increase, at least or about a 45% increase, at least or about a 50% increase, at least or about a 55% increase, at least or about a 60% increase, at least or about a 65% increase, at least or about a 70% increase, at least or about a 75% increase, at least or about a 80% increase, at least or about a 85% increase, at least or about a 90% increase, at least or about a 95% increase, relative to a control level.

Relative to a control level, the level that is determined may a decreased level. As used herein, the term "decreased" with respect to level (e.g., protein or mRNA level) refers to any % decrease below a control level. In various embodiments, the decreased level may be at least or about a 5% decrease, at least or about a 10% decrease, at least or about a 15% decrease, at least or about a 20% decrease, at least or about a 25% decrease, at least or about a 30% decrease, at least or about a 35% decrease, at least or about a 40% decrease, at least or about a 45% decrease, at least or about a 50% decrease, at least or about a 55% decrease, at least or about a 60% decrease, at least or about a 65% decrease, at least or about a 70% decrease, at least or about a 75% decrease, at least or about a 80% decrease, at least or about a 85% decrease, at least or about a 90% decrease, at least or about a 95% decrease, relative to a control level.

The terms "polypeptide," "peptide" and "protein" are used interchangeably herein to refer to a polymer of amino acid residues, wherein the polymer may in embodiments be conjugated to a moiety that does not consist of amino acids. The terms also apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed or chemically synthesized as a single moiety.

"Polypeptide fragment" refers to a polypeptide that has an amino-terminal and/or carboxy-terminal deletion, in which the remaining amino acid sequence is usually identical to the corresponding positions in the naturally-occurring sequence. Fragments typically are at least 5, 6, 8 or 10 amino acids long, at least 14 amino acids long, at least 20 amino acids long, at least 50 amino acids long, or at least 70 amino acids long.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. In embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "identical" or percent "identity," in the context of two or more nucleic acids or polypeptide sequences, refer to two or more sequences or subsequences that are the same or have a specified percentage of amino acid residues or nucleotides that are the same (e.g., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire polypeptide sequence or an individual domain thereof), when compared and aligned for maximum correspondence over a comparison window, or designated region as measured using a sequence comparison algorithm or by manual alignment and visual inspection. In embodiments, two sequences are 100% identical. In embodiments, two sequences are 100% identical over the entire length of one of the sequences (e.g., the shorter of the two sequences where the sequences have different lengths). In embodiments, identity may refer to the complement of a test sequence. In embodiments, the identity exists over a region that is at least about 10 to about 100, about 20 to about 75, about 30 to about 50 amino acids or nucleotides in length. In embodiments, the identity exists over a region that is at least about 50 amino acids or nucleotides in length, or more preferably over a region that is 100 to 500, 100 to 200, 150 to 200, 175 to 200, 175 to 225, 175 to 250, 200 to 225, 200 to 250 or more amino acids or nucleotides in length.

For sequence comparison, typically one sequence acts as a reference sequence, to which test sequences are compared. In embodiments, when using a sequence comparison algorithm, test and reference sequences are entered into a computer, subsequence coordinates are designated, if necessary, and sequence algorithm program parameters are designated.

Preferably, default program parameters can be used, or alternative parameters can be designated. The sequence comparison algorithm then calculates the percent sequence identities for the test sequences relative to the reference sequence, based on the program parameters.

A "comparison window" refers to a segment of any one of the number of contiguous positions (e.g., least about 10 to about 100, about 20 to about 75, about 30 to about 50, 100 to 500, 100 to 200, 150 to 200, 175 to 200, 175 to 225, 175 to 250, 200 to 225, 200 to 250) in which a sequence may be compared to a reference sequence of the same number of contiguous positions after the two sequences are optimally aligned. In embodiments, a comparison window is the entire length of one or both of two aligned sequences. In embodiments, two sequences being compared comprise different lengths, and the comparison window is the entire length of the longer or the shorter of the two sequences. In embodiments relating to two sequences of different lengths, the comparison window includes the entire length of the shorter of the two sequences. In embodiments relating to two sequences of different lengths, the comparison window includes the entire length of the longer of the two sequences.

Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see. e.g., Current Protocols in Molecular Biology (Ausubel et al., eds. 1995 supplement)).

Non-limiting examples of algorithms that are suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 may be used, with the parameters described herein, to determine percent sequence identity for nucleic acids and proteins. Software for performing BLAST analyses is publicly available through the National Center for Biotechnology Information (NCBI), as is known in the art. An exemplary BLAST algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues: always >0) and N (penalty score for mismatching residues: always <0)). For amino acid sequences, a scoring matrix is used to calculate the cumulative score. Extension of the word hits in each direction are halted when: the cumulative alignment score falls off by the quantity X from its maximum achieved value: the cumulative score goes to zero or below; due to the accumulation of one or more negative-scoring residue alignments; or the end of either sequence is reached. The BLAST algorithm parameters W. T, and X determine the sensitivity and speed of the alignment. In embodiments, the NCBI BLASTN or BLASTP program is used to align sequences. In embodiments, the BLASTN or BLASTP program uses the defaults used by the NCBI. In embodiments, the BLASTN program (for nucleotide sequences) uses as defaults: a word size (W) of 28: an expectation threshold (E) of 10; max matches in a query range set to 0; match/mismatch scores of 1, −2: linear gap costs; the filter for low complexity regions used; and mask for lookup table only used. In embodiments, the BLASTP program (for amino acid sequences) uses as defaults: a word size (W) of 3: an expectation threshold (E) of 10: max matches in a query range set to 0); the BLOSUM62 matrix (see Henikoff & Henikoff, Proc. Natl. Acad. Sci. USA 89:10915 (1992)): gap costs of existence: 11 and extension: 1; and conditional compositional score matrix adjustment.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

"Nucleic acid" refers to nucleotides (e.g., deoxyribonucleotides, ribonucleotides, and 2'-modified nucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g. polynucleotides contemplated herein include any types of RNA, e.g. mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amio acid on a protein or polypeptide through a covalent, non-covalent, or other interaction.

The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones: non-ionic backbones, modified sugars, and non-ribose backbones (e.g. phosphorodiamidate morpholino oligos or locked nucleic acids (LNA) as known in the art), including those described in U.S. Pat. Nos. 5,235, 033 and 5,034,506, and Chapters 6 and 7, ASC Symposium Series 580, CARBOHYDRATE MODIFICATIONS IN ANTISENSERE-SEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences As may be used herein, the terms "nucleic acid," "nucleic acid molecule." "nucleic acid oligomer," "oligonucleotide," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides and/or ribonucleotides, and/or analogs, derivatives or modifications thereof. Different polynucleotides may have different three-dimensional structures, and may perform various functions, known or unknown. Non-limiting examples of polynucleotides include genomic DNA, a genome, mitochondrial DNA, a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences.

The term "amino acid residue," as used herein, encompasses both naturally-occurring amino acids and non-naturally-occurring amino acids. Examples of non-naturally occurring amino acids include, but are not limited to, D-amino acids (i.e. an amino acid of an opposite chirality to the naturally-occurring form), N-$\alpha$-methyl amino acids, C-$\alpha$-methyl amino acids, $\beta$-methyl amino acids and D- or L-$\beta$-amino acids. Other non-naturally occurring amino acids include, for example, $\beta$-alanine ($\beta$-Ala), norleucine (Nle), norvaline (Nva), homoarginine (Har), 4-aminobutyric acid ($\gamma$-Abu), 2-aminoisobutyric acid (Aib), 6-aminohexanoic acid (8-Ahx), ornithine (orn), sarcosine, $\alpha$-amino isobutyric acid, 3-aminopropionic acid, 2,3-diaminopropionic acid (2,3-diaP), D- or L-phenylglycine, D-(trifluoromethyl)-phenylalanine, and D-p-fluorophenylalanine.

As used herein, "peptide bond" can be a naturally-occurring peptide bond or a non-naturally occurring (i.e. modified) peptide bond. Examples of suitable modified peptide bonds are well known in the art and include, but are not limited to, $-CH_2NH-$, $-CH_2S-$, $-CH_2CH_2-$, $-CH=CH-$ (cis or trans), $-COCH_2-$, $-CH(OH)$ $CH_2-$, $-CH_2SO-$, $-CS-NH-$ and $-NH-CO-$ (i.e. a reversed peptide bond) (see, for example, Spatola, Vega Data Vol. 1, Issue 3, (1983): Spatola, in *Chemistry and Biochemistry of Amino Acids Peptides and Proteins*, Weinstein, ed., Marcel Dekker, New York, p. 267 (1983); Morley, J. S., *Trends Pharm. Sci*. pp. 463-468 (1980); Hudson et al., *Int. J. Pept. Prot. Res.* 14:177-185 (1979); Spatola et al., *Life Sci.* 38:1243-1249 (1986): Hann, *J. Chem. Soc. Perkin Trans.* 1 307-314 (1982); Almquist et al., *J. Med. Chem.* 23:1392-1398 (1980): Jennings-White et al., *Tetrahedron Lett.* 23:2533 (1982); Szelke et al., EP 45665 (1982); Holladay et al., *Tetrahedron Lett.* 24:4401-4404 (1983); and Hruby, *Life Sci.* 31:189-199 (1982)).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule: alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

Methods for Treating a Coronavirus, e.g., SARS-CoV-2 and Other Viral Infections

Included herein is a method of preventing or treating a coronavirus, e.g., SARS-CoV-2 in a subject in need thereof. In further embodiments, the method comprises administering to the subject an effective amount of the composition comprising engineered NK cells expressing a CAR comprising an extracellular banana lectin domain, e.g., an H84T-BanLec domain. For example, methods for preventing or treating coronavirus, e.g., SARS-CoV-2, include administering a composition comprising engineered NK cells expressing a CAR comprising an extracellular banana lectin domain, e.g., an H84T-BanLec domain.

In other embodiments, the methods for treating coronavirus, e.g., SARS-CoV-2 comprise administering to a subject a composition comprising engineered NK cells expressing a CAR comprising an extracellular banana lectin domain, e.g., an H84T-BanLec domain produced according to the methods described herein, in combination with methods for controlling the outset of symptoms. In particular, the combination treatment can include administering readily known treatments. Additionally, combination therapy may include antivirals.

The present methods and compositions also may be utilized in the same manner disclosed herein to treat subjects and cells infected with or susceptible to infection with other coronaviruses such as Middle East Respiratory Syndrome coronavirus (MERS-COV) and/or, SARS-coronavirus (SARS-CoV) (severe acute respiratory syndrome). Thus for example, methods are provided for treating a infection of Middle East Respiratory Syndrome coronavirus (MERS-COV) and/or SARS-coronavirus (SARS-CoV) that comprise administering to a subject or cells in need thereof (e.g. a subject or cells infected with Middle East Respiratory Syndrome coronavirus (MERS-COV) and/or SARS-coronavirus (SARS-CoV)) a composition comprising engineered NK cells expressing a CAR comprising an extracellular banana lectin domain, e.g., an H84T-BanLec domain produced according to the methods described herein, in combination with methods for controlling the outset of symptoms. In particular, the combination treatment can include administering readily known treatments. Additionally, combination therapy may include antivirals.

The present methods and compositions also may be utilized in the same manner disclosed herein to treat subjects and cells infected with or susceptible to infection with retroviruses including HIV, SIV. SHIV and/or HTLV and/or lentiviruses. Thus for example, methods are provided for treating a retrovirus infection such as HIV, SIV, SHIV and/or HTLV and/or a lentivirus that comprise administering to a subject or cells in need thereof (e.g. a subject or cells infected with a retrovirus such as HIV, SIV, SHIV and/or HTLV and/or a lentivirus) a composition comprising engineered NK cells expressing a CAR comprising an extracellular banana lectin domain, e.g., an H84T-BanLec domain produced according to the methods described herein, in combination with methods for controlling the outset of symptoms. In particular, the combination treatment can include administering readily known treatments. Additionally, combination therapy may include antivirals.

The described composition can be administered as a pharmaceutically or physiologically acceptable preparation or composition containing a physiologically acceptable carrier, excipient, or diluent, and administered to the tissues of the recipient organism of interest, including humans and non-human animals.

The composition comprising engineered NK cells expressing a CAR comprising an extracellular banana lectin domain, e.g., an H84T-BanLec domain can be prepared by re-suspending in a suitable liquid or solution such as sterile physiological saline or other physiologically acceptable injectable aqueous liquids. The amounts of the components to be used in such compositions can be routinely determined by those having skill in the art.

In examples, for injectable administration, the composition (e.g., a composition comprising engineered NK cells expressing a CAR comprising an extracellular banana lectin domain, e.g., an H84T-BanLec domain) is in sterile solution or suspension or can be resuspended in pharmaceutically- and physiologically-acceptable aqueous or oleaginous vehicles, which may contain preservatives, stabilizers, and material for rendering the solution or suspension isotonic with body fluids (i.e. blood) of the recipient. Non-limiting examples of excipients suitable for use include water, phosphate buffered saline, pH 7.4, 0.15 M aqueous sodium chloride solution, dextrose, glycerol, dilute ethanol, and the like, and mixtures thereof. Illustrative stabilizers are polyethylene glycol, proteins, saccharides, amino acids, inorganic acids, and organic acids, which may be used either on their own or as admixtures. The amounts or quantities, as well as the routes of administration used, are determined on an individual basis, and correspond to the amounts used in similar types of applications or indications known to those of skill in the art.

In embodiments, a therapeutically effective amount of the composition (e.g., a composition comprising engineered NK cells expressing a CAR comprising an extracellular banana lectin domain, e.g., an H84T-BanLec domain) in humans can be any therapeutically effective amount. In one embodiment, the composition (e.g., a composition comprising engineered NK cells expressing a CAR comprising an extracellular banana lectin domain, e.g., an H84T-BanLec domain) is administered thrice daily, twice daily, once daily, fourteen days on (four times daily, thrice daily or twice daily, or once daily) and 7 days off in a 3-week cycle, up to five or seven days on (four times daily, thrice daily or twice daily, or once daily) and 14-16 days off in 3 week cycle, or once every two days, or once a week, or once every 2 weeks, or once every 3 weeks.

In an embodiment, the composition (e.g., a composition comprising engineered NK cells expressing a CAR comprising an extracellular banana lectin domain, e.g., an H84T-BanLec domain) is administered once a week, or once every two weeks, or once every 3 weeks or once every 4 weeks for at least 1 week, in some embodiments for 1 to 4 weeks, from 2 to 6 weeks, from 2 to 8 weeks, from 2 to 10 weeks, or from 2 to 12 weeks, 2 to 16 weeks, or longer (e.g., 1, 2, 3, 4, 5, 6, 7, 8, 9, 10, 11, 12, 36, 48, or more weeks).

Additional advantages of the methods described herein include that the composition comprising the engineered NK cells expressing a CAR comprising an extracellular banana lectin domain, e.g., an H84T-BanLec domain can be injected systemically, as opposed to local delivery. Additional advantages include that patients requiring treatment typically require at least 1 local injections, and the injections are about 7 days apart. The compositions and methods described herein provide that patients require about 1 injection(s), systemically. In some examples, the injections can be every week.

Pharmaceutical Compositions and Formulations

The present invention provides pharmaceutical compositions comprising an effective amount of a composition (e.g., a composition comprising engineered NK cells expressing a chimeric antigen receptor (CAR) which comprises an extracellular banana lectin domain, e.g., an H84T-BanLec domain) and at least one pharmaceutically acceptable excipient or carrier, wherein the effective amount is as described above in connection with the methods of the invention.

In one embodiment, the composition (e.g., a composition comprising engineered NK cells expressing a CAR comprising an extracellular banana lectin domain, e.g., an H84T-BanLec domain) is further combined with at least one additional therapeutic agent in a single dosage form. In one embodiment, the at least one additional therapeutic agent comprises an antiviral agent.

Non-limiting examples of anti-viral agents that may be used in combination as described herein include Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Kethoxal; Lamivudine; Lobucavir; Memotine Hydrochloride; Methisazone; Nevirapine; Penciclovir; Pirodavir; Ribavirin; Rimantadine Hydrochloride; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; and Zinviroxime.

Additional examples of one or more therapeutic agents that may be used in combination as described herein include include r one or more of hyperimmune globulins, remdesivir, oseltamivir. Galidesivir (BCX4430. Immucillin-A). 3-Deazaneplanocin A (DZNep, C-c3 Ado). Favipiravir (T-705. Avigan), lopinavir: ritonavir, lopinavir/ritonavir (e.g. KALETRA), ribavirin, lopinavir/ritonavir/ribavirin, Recombinant human interferon $\alpha1\beta$, Huaier (including Huaier Granule), Eculizumab (Soliris), Recombinant human angiotensin-converting enzyme 2 (rhACE2), Carrimycin, Umifenivir (Arbidol), chloroquine phosphate, T89 (Dantonic), Fingolimod (including Fingolimod 0.5 mg), N-acetylcysteine, N-acetylcysteine+Fuzheng Huayu Tablet, YinHu QingWen Decoction, LV-SMENP-DC vaccine and/or antigen-specific CTLs.

The term "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. Examples of pharmaceutically acceptable excipients include, without limitation, sterile liquids, water, buffered saline, ethanol, polyol (for example, glycerol, propylene glycol, liquid polyethylene glycol and the like), oils, detergents, suspending agents, carbohydrates (e.g., glucose, lactose, sucrose or dextran), antioxidants (e.g., ascorbic acid or glutathione), chelating agents, low molecular weight proteins, or suitable mixtures thereof.

A pharmaceutical composition can be provided in bulk or in dosage unit form. It is especially advantageous to formulate pharmaceutical compositions in dosage unit form for ease of administration and uniformity of dosage. The term "dosage unit form" as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved. A dosage unit form can be an ampoule, a vial, a suppository, a dragee, a tablet, a capsule, an IV bag, or a single pump on an aerosol inhaler.

In therapeutic applications, the dosages vary depending on the agent, the age, weight, and clinical condition of the recipient patient, and the experience and judgment of the clinician or practitioner administering the therapy, among other factors affecting the selected dosage. Generally, the dose should be a therapeutically effective amount. Dosages can be provided in mg/kg/day units of measurement (which dose may be adjusted for the patient's weight in kg, body surface area in $m^2$, and age in years). Exemplary doses and dosages regimens for the compositions in methods of treating muscle diseases or disorders are described herein.

The pharmaceutical compositions can take any suitable form (e.g. liquids, aerosols, solutions, inhalants, mists, sprays; or solids, powders, ointments, pastes, creams, lotions, gels, patches and the like) for administration by any desired route (e.g. pulmonary, inhalation, intranasal, oral, buccal, sublingual, parenteral, subcutaneous, intravenous, intramuscular, intraperitoneal, intrapleural, intrathecal, transdermal, transmucosal, rectal, and the like). For example, a pharmaceutical composition of the invention may be in the form of an aqueous solution or powder for aerosol administration by inhalation or insufflation (either through the mouth or the nose), in the form of a tablet or capsule for oral administration; in the form of a sterile aqueous solution or dispersion suitable for administration by either direct injection or by addition to sterile infusion fluids for intravenous infusion; or in the form of a lotion, cream, foam, patch, suspension, solution, or suppository for transdermal or transmucosal administration.

In embodiments, the pharmaceutical composition comprises an injectable form.

A pharmaceutical composition can be in the form of an orally acceptable dosage form including, but not limited to, capsules, tablets, buccal forms, troches, lozenges, and oral liquids in the form of emulsions, aqueous suspensions, dispersions or solutions. Capsules may contain mixtures of a compound of the present invention with inert fillers and/or diluents such as the pharmaceutically acceptable starches (e.g., corn, potato or tapioca starch), sugars, artificial sweetening agents, powdered celluloses, such as crystalline and microcrystalline celluloses, flours, gelatins, gums, etc.

A pharmaceutical composition can be in the form of a sterile aqueous solution or dispersion suitable for parenteral administration. The term parenteral as used herein includes subcutaneous, intracutaneous, intravenous, intramuscular, intra-articular, intraarterial, intrasynovial, intrasternal, intrathecal, intralesional and intracranial injection or infusion techniques.

A pharmaceutical composition can be in the form of a sterile aqueous solution or dispersion suitable for administration by either direct injection or by addition to sterile infusion fluids for intravenous infusion, and comprises a solvent or dispersion medium containing, water, ethanol, a polyol (e.g., glycerol, propylene glycol and liquid polyethylene glycol), suitable mixtures thereof, or one or more vegetable oils. Solutions or suspensions of the compound of the present invention as a free base or pharmacologically acceptable salt can be prepared in water suitably mixed with a surfactant. Examples of suitable surfactants are given below. Dispersions can also be prepared, for example, in glycerol, liquid polyethylene glycols and mixtures of the same in oils.

The pharmaceutical compositions for use in the methods of the present invention can further comprise one or more additives in addition to any carrier or diluent (such as lactose or mannitol) that is present in the formulation. The one or more additives can comprise or consist of one or more surfactants. Surfactants typically have one or more long aliphatic chains such as fatty acids which enables them to insert directly into the lipid structures of cells to enhance drug penetration and absorption. An empirical parameter commonly used to characterize the relative hydrophilicity and hydrophobicity of surfactants is the hydrophilic-lipophilic balance ("HLB" value). Surfactants with lower HLB values are more hydrophobic, and have greater solubility in oils, while surfactants with higher HLB values are more hydrophilic, and have greater solubility in aqueous solutions. Thus, hydrophilic surfactants are generally considered to be those compounds having an HLB value greater than about 10, and hydrophobic surfactants are generally those having an HLB value less than about 10. However, these HLB values are merely a guide since for many surfactants, the HLB values can differ by as much as about 8 HLB units, depending upon the empirical method chosen to determine the HLB value. All percentages and ratios used herein, unless otherwise indicated, are by weight.

A typical amount of cells (e.g., engineered immune cells) administered to a mammal (e.g., a human) can be, for example, in the range of one million to 100 billion cells; however, amounts below or above this exemplary range are within the scope of the disclosure. For example, the daily dose of cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), preferably about 10 million to about 100 billion cells (e.g., about 20 million cells, about 30 million cells, about 40 million cells, about 60) million cells, about 70 million cells, about 80 million cells, about 90 million cells, about 10 billion cells, about 25 billion cells, about 50 billion cells, about 75 billion cells, about 90) billion cells, or a range defined by any two of the foregoing values), more preferably about 100 million cells to about 50 billion cells (e.g., about 120 million cells, about 250 million cells, about 350) million cells, about 450 million cells, about 650 million cells, about 800 million cells, about 900 million cells, about 3 billion cells, about 30 billion cells, about 45 billion cells, or a range defined by any two of the foregoing values).

Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

Kits Comprising the Composition Comprising Engineered NK Cells Expressing a CAR Comprising an Extracellular Banana Lectin Domain, e.g., an H84T-BanLec Domain In aspects, a kit for producing an engineered NK cell expressing a CAR comprising an extracellular banana lectin domain (e.g., an H84T-BanLec domain) is provided. In embodiments, the kit comprises the engineered NK cell and reagents.

In embodiments, the composition in the kit is suitable for delivery (e.g., local injection) to a subject.

The present invention also provides packaging and kits comprising pharmaceutical compositions for use in the methods of the present invention. The kit can comprise one or more containers selected from the group consisting of a bottle, a vial, an ampoule, a blister pack, and a syringe. The kit can further include one or more of instructions for use in treating and/or preventing a disease, condition or disorder of the present invention (e.g., a coronavirus, e.g., SARS-COV2), one or more syringes, one or more applicators, or a sterile solution suitable for reconstituting a pharmaceutical composition of the present invention.

EXAMPLES

The following examples illustrate certain specific embodiments of the invention and are not meant to limit the scope of the invention. Embodiments herein are further illustrated by the following examples and detailed protocols. However, the examples are merely intended to illustrate embodiments and are not to be construed to limit the scope herein. The contents of all references and published patents and patent applications cited throughout this application are hereby incorporated by reference.

Example 1: H84T BanLec CAR-T Cells

Figure 3B:
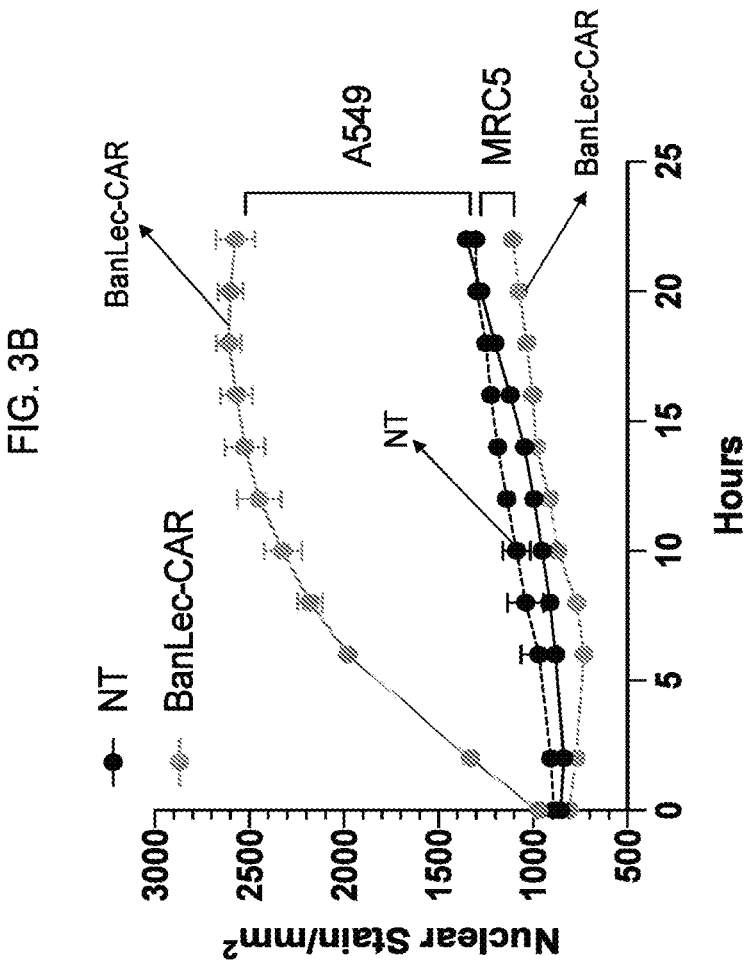
FIGS. 3A and 3B are data showing that the H84T-BanLec CAR can be engineered for T cell surface expression and that H84-BanLec CAR T cells are specific for lung cancer.
Figure 3A:
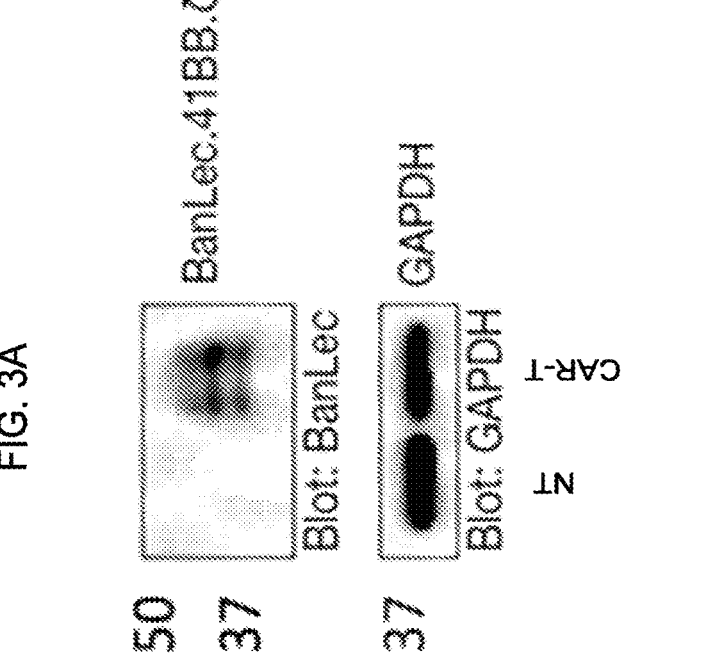
Figure 4:
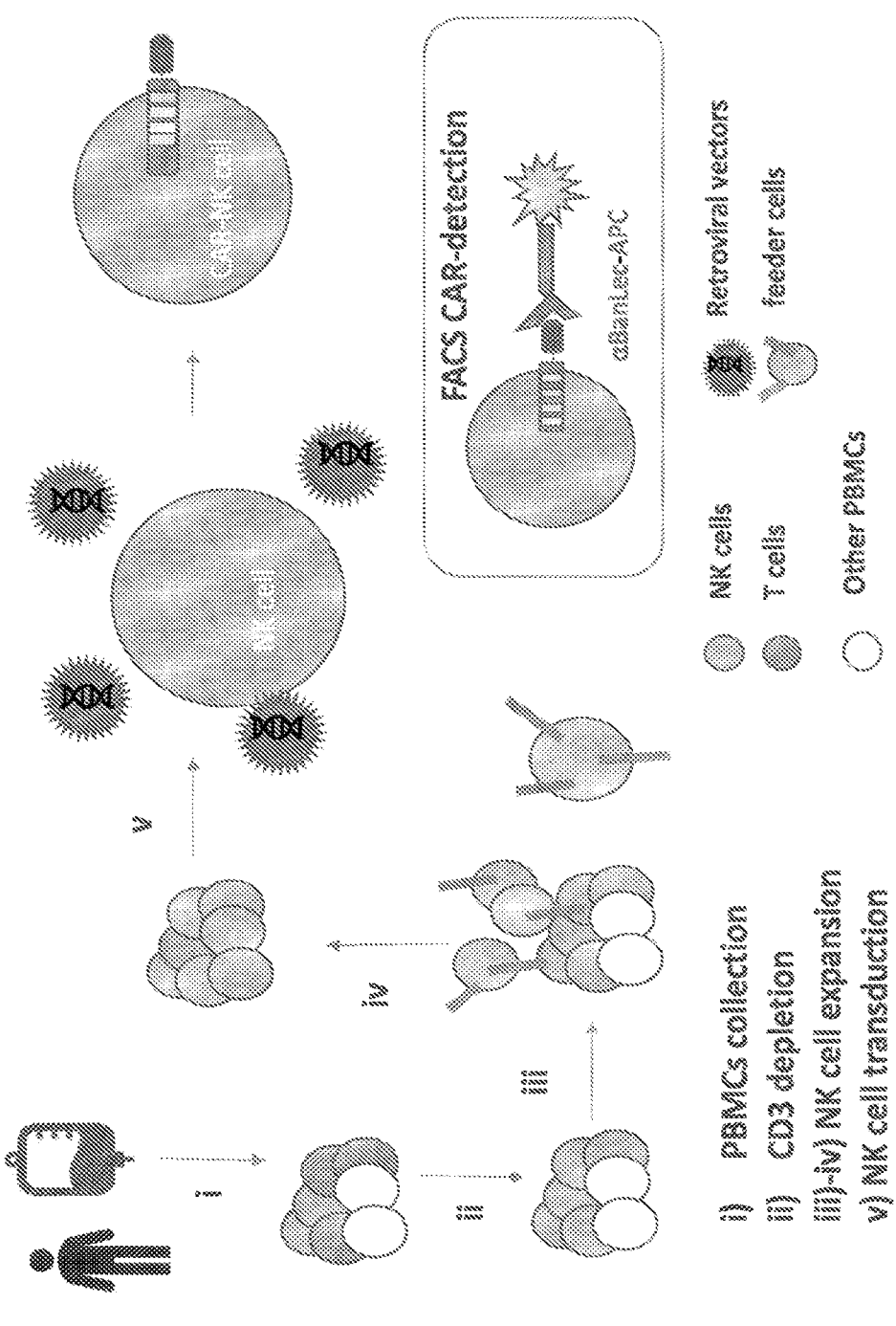
FIG. 4 is a schematic of CAR-NK cell production. i.) Peripheral Blood Mononuclear Cells (PBMCs) isolated from donor peripheral blood. ii.) T cells depleted iii.) NK cells stimulated with lethally irradiated feeder cells iv.) NK cells maintained and expanded in recombinant IL-2 (interleukin 2), v.) NK cells transduced with replication incompetent retroviral vector carrying CAR coding sequences.
Figure 5:
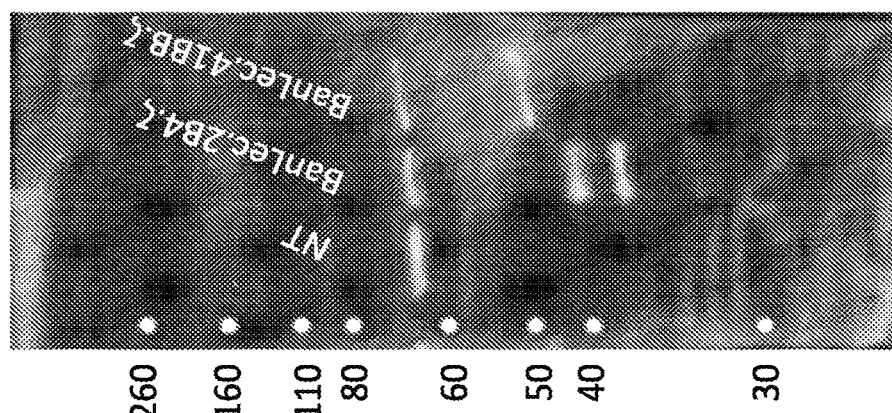
FIG. 5 is an image of a blot showing H84T Ban-Lec CAR expression in human NK cells, detected via Western blot against the TCRζ chain (C-terminal component of CAR), NT: non-transduced NK cells included as negative control. 2B4 and 41BB refer to intracellular signaling components encoded by unique H84T BanLec CAR constructs.
Figures 6A, 6B:
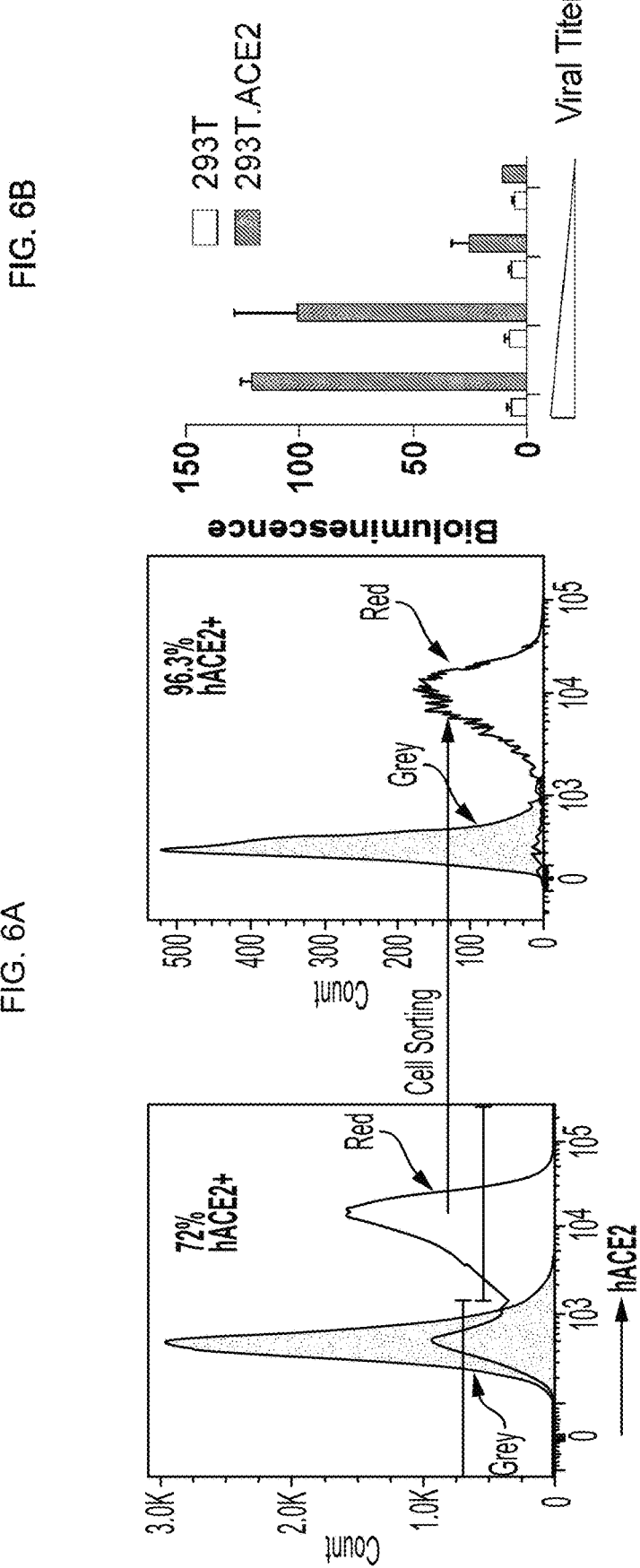
FIGS. 6A and 6B are images showing infectivity of S-protein pseudotyped lentivirus to cells expressing the human ACE2 receptor.

H84T-BanLec CAR was engineered into T cells, exploiting the lectin as an alternate to a conventional single chain variable fragment (scFv) for antigen binding (FIG. 3A). Targeting of glycans is not subject to the antigenic down-modulation seen in clinical trials of targeted cell therapies. The H84T BanLec serves as the extracellular domain of the receptor.

Cancer-specific T cell activation and killing was performed, given the altered glycobiology of transformed cells. Indeed, the H84T-BanLec CAR T cells were functional, with specific T cell activation and anti-cancer killing (FIG. 3B). H84T-BanLec CAR T cells were not toxic to the MRC5 normal lung fibroblast cell line (FIG. 3B). These are a promising therapeutic under development, with patent pending for design and use (see U.S. patent application Ser. No. 16/782,417 which is published as US2020/0247868), incorporated herein by reference in its entirety).

The novel binding mechanism is a first-in-class immunotherapy as prior targeting of glycans has been tested using only antibody-based binding moieties. Glycosite binding via H84T-BanLec as a mechanism of engineered effector cell targeting can be extended to direct cytotoxicity against invasive pathogens decorated with oligomannose-containing glycoproteins. SARS-CoV-2 is one such pathogen.

Oligomannose containing glycan shields surround the SARS-CoV-2 ACE2 receptor binding domain (RBD), which are hypothesized to protect binding topology and are therefore unlikely to be altered by mutagenesis that would otherwise lead to evasion of epitope targeting.

Example 2: Evaluation of Binding and Antigen Specific Activation of H84T-BanLec CAR NK Cells by SARS-CoV-2 Envelope Proteins NK cells are engineered with H84T-BanLec.CARs. Recombinant SARS-CoV-2 envelope proteins (S-trimer, M, E) are used to evaluate specific binding and CAR-NK cell activation.

To confirm that the H84T-BanLec binds SARS-CoV-2, commercially sourced recombinant spike envelope proteins, for example, available from Acrobiosystems, Newark, DE (Catalog No: S1N-C5256-100 ug, "SARS-CoV-2 (COVID-19) S1 protein (D614G), His Tag"), are used. These proteins (for example from Acrobiosystems) produces the recombinant proteins in human HEK293T cells to preserve human host derived glycosylation patterns. H84T-BanLec CAR was expressed with 4-1BB and TCRζ signaling domains in T cells FIG. 3A. A CAR with 2B4.ζ intracellular domains can be optimal for NK cell activation.

The existing 2B4.ζ CAR is modified to include the H84T-BanLec extracellular domain (e.g., for targeting viruses). H84T-BanLec CAR NK cells re-generated from healthy donor peripheral blood. Peripheral blood mononuclear cells (PBMCs) are isolated with a density gradient and depleted of CD3 (+) T cells. CD3 (−) PBMCs are stimulated with lethally irradiated K562.41BBL.IL15 feeder cells and maintained in IL-2 (interleukin 2). Moreover, the CARs described herein are NK cells (not T cells), which was confirmed by immunophenotyping.

On day 4 of activation, cells are transduced with replication incompetent retroviruses carrying the coding sequences of the CARs. CAR expression is verified using a monoclonal antibody to H84T-BanLec. Once CAR expression is demonstrated, it will be determined whether H84T-BanLec CAR NK cells bind glycosites present in the of SARS-CoV-2 envelope. His-tagged recombinant envelope proteins (trimeric S—, M-, E-proteins) are used in FACS-based binding assays. Cells are coated with different concentrations of His-envelope proteins and binding is analyzed by flow cytometry. Density of binding will be quantified with Bangs beads (Bangs Laboratories, Inc, Fishers, IN). Glycoprotein-Specific Activation of the H84T-BanLec.CAR NK Cells is Evaluated.

Recombinant SARS-CoV-2 envelope proteins are immobilized on tissue culture plates.

H84T-BanLec.CAR NK are added to the plates and sampled at 4, 24, and 48 hrs after activation. NK cells are evaluated by measuring:

Cytokine production (for example, IFNγ (interferon gamma), GM-CSF (Granulocyte-macrophage colony-stimulating factor), TNFα (tumor necrosis factor alpha)), Expression/upregulation of activating receptors, for example, CD16 (cluster of differentiation 16), NKG2D, CD161 (cluster of differentiation 161), NKp46, or NKp30

Expression/upregulation of activation markers, for example, CD69 (cluster of differentiation 69), or CD94/NKG2C, Expression/upregulation of inhibitory receptors, for example CD94/NKG2A, Expression/upregulation of T-cell exhaustion markers such as programmed death ligand 1 (PD-1), and/or Degranulation of perforin and granzyme.

Additionally, target-specific proliferation of H84T-BanLec.CAR-NK cells is measured. Unmodified NK cells and empty wells are used as controls. Experiments are repeated with at least three independent PBMC donors.

Example 3: H84T-BanLec. CAR NK Cell Mediated Prevention of SARS-CoV-2 Infection of Human Epithelial Cells Target cells are engineered to express the ACE2 receptor protein. Engineered cells are coated with SARS-CoV-2 viral glycoproteins and co-cultured with our H84T-BanLec.CAR NK cells. CAR-NKs are evaluated for i.) target-specific proliferation, ii.) cytokine secretion, iii.) immunophenotype, and iv.) target cytotoxicity. Replication incompetent retrovirus pseudotyped with the SARS-COV2 spike protein transduced 293T.hACE2 cell line.

H84T-BanLec.CAR NK cells are a promising therapeutic, capable of clearing circulating virus as well as infected cells.

Translation of the H84T-BanLec.CAR NK cells from benchtop to clinic may provide a valuable therapeutic candidate to treat SARS-CoV-2 infection.

Respiratory epithelial cells infected with SARS-CoV-2 retain expression of viral envelope glycoproteins on the epithelial cell membrane. The binding receptor for SARS-CoV-2 is the ACE2 transmembrane protein. HEK293T cells can be engineered to express ACE2 and bind coronaviruses. Cellular models resembling SARS-CoV2 infection are created using recombinant envelope proteins, S-protein pseudotyped lentivirus, and ACE2 engineered HEK293T.

A plasmid encoding myc-tagged human ACE2 cDNA is available from the Addgene plasmid biobank (Addgene, Watertown, MA) and is used for subcloning into a lentiviral expression plasmid. HEK293T cells are transduced with ACE2 containing lentiviral vectors to establish ACE2 surface expression.

Stable introduction of firefly Luciferase (fflLuc) expression using replication incompetent retrovirus sourced from a producer cell line can be used. The fflLuc vector additionally carries GFP. In this way, ACE2.293T.fflLuc.GFP can be generated.

Expression is verified with FACS using hACE2 antibodies. Cells are sorted to purify lines with low, medium, and high ACE2 expression. Once these are purified, hACE2.HEK293T cells are coated with the recombinant trimeric S-protein. S-protein binding to ACE2 on the cell surface is analyzed with FACs to determine the optimal S-protein concentration for receptor saturation.

S-protein coated hACE2.cells are co-cultured with BanLec-CAR NK cells at 10:1, 2:1, 1:2, and 1:10 effector:target cell ratios. NK synapse formation, activation, proliferation, and cytotoxicity is evaluated. NK cell immunophenotype after stimulation is evaluated to determine expression of exhaustion-associated surface markers. Uncoated 293T cell lines and unmodified NK cells are used as controls. All experiments are conducted using at least three independent healthy donor PBMC sources.

Trimeric S-protein binds the ACE2 receptor. H84T-BanLec.CAR NK cells bind S-protein cultured epithelial cells with resultant activation and cytotoxicity. If synapse formation and target killing does not occur, the use of live virus will be done in the assays. Additionally, viral clearance may be tested and H84T-BanLec.CAR NK impact on SARS-CoV2 infectivity.
Statistical Analysis.

All binding, signaling, activation, and cytotoxicity studies are performed at least in biological triplicate. CAR-NK cells are generated and tested from at least three independent NK cell donors to validate reproducibility. Statistical comparisons between two groups are performed by one-way analysis of variance (ANOVA) with Tukey post-tests. Two-way ANOVA corrected for comparison using the method of Sidek are used for comparison of 3 or more groups. Calculated differences of p<0.05 are considered statistically significant.

REFERENCES

1. Koshte, V. L., et al., *Isolation and characterization of BanLec-I, a mannoside-binding lectin from Musa paradisiac (banana)*. Biochem J, 1990. 272 (3): p. 721-6.
2. Hopper, J. T. S., et al., *The Tetrameric Plant Lectin BanLec Neutralizes HIV through Bidentate Binding to Specific Viral Glycans*. Structure, 2017. 25 (5): p. 773-782 e5.

3. Li, W., et al., *Angiotensin-converting enzyme 2 is a functional receptor for the SARS coronavirus*. Nature, 2003. 426 (6965): p. 450-4.

4. Wrapp, D., et al., *Cryo-EM structure of the 2019-nCOV spike in the prefusion conformation*. Science, 2020. 367 (6483): p. 1260-1263.

5. Watanabe, Y., et al., *Site-specific analysis of the SARS-CoV-2 glycan shield*. BioRxiv, 2020.

6. Zhang, Y., et al., *Site-specific N-glycosylation Characterization of Recombinant SARS-CoV-2 Spike Proteins using High-Resolution Mass Spectrometry*. bioRxiv, 2020.

7. Shajahan, A., et al., *Deducing the N-and O-glycosylation profile of the spike protein of novel coronavirus SARS-CoV-2*. bioRxiv, 2020.

8. Coves-Datson, E. M., et al., *A molecularly engineered antiviral banana lectin inhibits fusion and is efficacious against influenza virus infection in vivo*. Proc Natl Acad Sci USA, 2020. 117 (4): p. 2122-2132.

9. Swanson, M. D., et al., *A lectin isolated from bananas is a potent inhibitor of HIV replication*. J Biol Chem, 2010. 285 (12): p. 8646-55.

10. Mitchell, C. A., K. Ramessar, and B. R. O'Keefe, *Antiviral lectins: Selective inhibitors of viral entry*. Antiviral Res, 2017. 142: p. 37-54.

11. Swanson, M. D., et al., *Engineering a therapeutic lectin by uncoupling mitogenicity from antiviral activity*. Cell, 2015. 163 (3): p. 746-58.

12. Imai, C., S. Iwamoto, and D. Campana, *Genetic modification of primary natural killer cells overcomes inhibitory signals and induces specific killing of leukemic cells*. Blood, 2005. 106 (1): p. 376-83.

13. Liu, E., et al., *Use of CAR-Transduced Natural Killer Cells in CD19-Positive Lymphoid Tumors*. N Engl J Med, 2020. 382 (6): p. 545-553.

14. Bonifant, C. L., et al., *Toxicity and management in CAR T-cell therapy*. Mol Ther Oncolytics, 2016. 3: p. 16011.

15. Bonifant, C. L., et al., *CD123-Engager T Cells as a Novel Immunotherapeutic for Acute Myeloid Leukemia*. Mol Ther, 2016. 24 (9): p. 1615-26.

16. Krawczyk, E., et al., *T-cell Activity against AML Improved by Dual-Targeted T Cells Stimulated through T-cell and IL7 Receptors*. Cancer Immunol Res, 2019. 7 (4): p. 683-692.

17. Zolov, S. N., S. P. Rietberg, and C. L. Bonifant, *Programmed cell death protein 1 activation preferentially inhibits CD28.CAR-T cells*. Cytotherapy, 2018. 20 (10): p. 1259-1266.

18. Giamarellos-Bourboulis, E. J., et al., *Complex Immune Dysregulation in COVID-19 Patients with Severe Respiratory Failure*. Cell Host Microbe, 2020.

19. Wang, F., et al., *Characteristics of peripheral lymphocyte subset alteration in COVID-19 pneumonia*. J Infect Dis, 2020.

20. Qin, C., et al., *Dysregulation of immune response in patients with COVID-19 in Wuhan. China*. Clin Infect Dis, 2020.

21. Siegler, E. L., et al., *Off-the-Shelf CAR-NK Cells for Cancer Immunotherapy*. Cell Stem Cell, 2018. 23 (2): p. 160-161.

22. Steentoft, C., et al., *Glycan-directed CAR-T cells*. Glycobiology, 2018. 28 (9): p. 656-669.

23. Procko, E., *The sequence of human ACE2 is suboptimal for binding the S spike protein of SARS coronavirus 2*. bioRxiv, 2020.

24. Fujisaki, H., et al., *Expansion of highly cytotoxic human natural killer cells for cancer cell therapy*. Cancer Res, 2009. 69 (9): p. 4010-7.

25. Bonifant, C. L. and S. K. Tasian, *The future of cellular immunotherapy for childhood leukemia*. Curr Opin Pediatr, 2020. 32 (1): p. 13-25.

Example 4

Materials and Methods

Cell Lines

HEK293T cells were purchased from the American Type Culture Collection (ATCC, Manassas, VA) and grown in Dulbecco's Modified Eagle Medium (DMEM; ThermoFisher Scientific Waltham, MA), supplemented with 10% Fetal Bovine Serum (FBS; HyClone, Logan, UT). High-expressing human ACE2 (hACE2) 293T cells were created by first subcloning hACE2 (pCEP4-myc-ACE21 was a gift from Erik Procko: Addgene plasmid #141185; http://n2t.net/addgene: 141185; RRID: Addgene_141185, Addgene, Watertown, MA) into a pCDH lentiviral backbone (System Biosciences, Palo Alto, CA). Vesicular stomatitis virus G glycoprotein (VSV-G) Pseudotyped HIV-derived lentiviral particles were then produced using the pPACKHI HIV Lentivector Packaging Kit (System Biosciences, Palo Alto, CA) according to the manufacturer's instructions and used for 293T.hACE2 cell generation. Cells with high ACE2 expression, as validated with flow cytometry, were then isolated via fluorescence-activated cell sorting (FACS). hACE2.293T cells used for cytotoxicity analysis were additionally modified with retroviral vectors to express an enhanced green fluorescent protein (GFP) firefly luciferase fusion gene (GFP.ffLuc).[53] GFP-positive cells were sorted and maintained in the appropriate complete growth medium. GFP expression was confirmed through flow cytometric analysis and luciferase expression was confirmed using D-luciferin and quantification of bioluminescence. All cells were maintained in a humidified atmosphere containing 5% $CO_2$ at 37° C.

Chimeric Antigen Receptor (CAR) Synthesis

The sequence of H84T-BanLec[32] was synthesized (GeneArt, ThermoFisher Scientific) and subcloned into a pSFG[54] retroviral vector backbone linked to the intracellular domains of 4-1BB (CD137) and TCRζ[36] More specifically, the lectin is linked to a CD8α hinge and transmembrane domain, CD137 intracellular domain, and the intracellular domain of TCRζ (H84T-BanLec.4-1BB.ζ). Transgenic sequence fidelity was validated by Sanger sequencing (Johns Hopkins Genetic Resources Core Facility).

Generation of CAR-NK Cells

Peripheral blood mononuclear cells were isolated from healthy donor leukopaks (Anne Arundel Medical Blood Donor Center, Annapolis, MD). T cells were then depleted with CD3-microbeads (Militenyi Biotec, Cologne, Germany). CD3+ cell depletion was verified with flow cytometry using Phycoerythrin (PE)-conjugated anti CD3 (clone: HIT3a, BD Biosciences, Franklin Lakes, NJ) and Brilliant Violet (BV) 421-conjugated anti-CD56 (clone: HCD56, BioLegend, San Diego, CA) antibodies. CD3-depleted peripheral blood mononuclear cells were stimulated on day 0 with lethally irradiated K562 feeder cells expressing membrane bound IL15 and 4-1BB ligand[45] at a 1:1 ratio. Cells were maintained in SGCM media (CellGenix, Freiburg, Germany) with 10% FBS and 2 mMol glutaMAX (ThermoFisher) supplemented with recombinant human interleukin (IL)-2 (200 IU/mL, preclinical biorepository, National Cancer Institute). NK cell transduction was performed on day 4 of the culture using transiently produced replication incompetent RD114-pseudotyped retroviral particles immobilized on RetroNectin (Clontech Laborotories, Palo Alto, CA).

Determination of Vector Copy Number (VCN)

Primer/probe-FAM was designed to the MMLV-derived psi present in pSFG[54] and purchased from ThermoFisher Scientific. RNAseP primer/probe-VIC/TAMRA mix (Applied Biosystems #4403326) was used as comparison. Genomic DNA was isolated from CAR-NK cells and 25 ng used for amplification with TaqMan Universal PCR Mastermix (ThermoFisher) and the above primer/probe mixes on a C1000 Touch Thermal Cycler (Bio-Rad, Hercules, CA). The following amplification conditions were used: 50° C. for 2 minutes, 95° C. for 10 minutes, 40 cycles of 95° C. for 15 seconds, 60° C. for 1 minute. No-template, unmodified NK cells and a condition containing only plasmid were used as controls. Vector copy number calculation was performed using the $2^{-\Delta Ct}$ method. 55

SARS-CoV-2 Spike Pseudotyped Viral Assays

SARS-CoV-2 S-protein pseudotyped replication incompetent lentiviral particles were produced by first transfecting 293T with GeneJuice transfection reagent (MilliporeSigma) and SARS-Related Coronavirus 2, Wuhan-Hu-1 Spike-Pseudotyped Lentiviral Kit (The following reagent was obtained through BEI Resources, NIAID, NIH: SARS-Related Coronavirus 2, Wuhan-Hu-1 Spike-Pseudotyped Lentiviral Kit, NR-52948: individual plasmids+0.56 at indicated ratios (Supplemental Table 1); BEI Resources Repository, Manassas, VA). S-protein pseudotyped viral supernatant was collected 48 h after transfection. $1.25\times10^4$ hACE2.293T cells were plated on day-1 in black 96-well microplates (Corning, Corning, NY). Parental 293T cells served as a control for nonspecific cell transduction. On Day 0, S-pseudoviral titrations (1:1, 1:5, 1:25, 1:125) were added and the plate was centrifuged at 800 g for 30' at 32° C. Cells were then incubated at 37° C. in 5% $CO_2$. At 48 h post-transduction, the viral-containing supernatant was aspirated and 150 ug/ml D-Luciferin containing fresh media added. BLI was measured and reactive light units (RLU) determined after subtraction of virus-only background. For co-culture assays containing NK cells and pseudovirus transduced target cells, pseudoviral particles were titrated first on hACE2.293T cells and added to achieve 100-200 maximum RLU. NK cells were added to the hACE2.293T and pseudovirus immediately after centrifugation. Decreased infectivity was calculated as 100*(baseline BLI–co-culture BLI)/(baseline BLI–background). Baseline BLI was measured from wells containing only hACE2.293T and pseudovirus. The assay was performed in experimental triplicate per donor.

Flow Cytometry

ACE2 expression on 293T cells was validated with flow cytometric analysis, utilizing staining with Alexa Fluor 647 conjugated anti-ACE2 Ab (Clone #535919; R&D Systems, Minneapolis, MT). CAR expression on the surface of transduced NK cells was evaluated 4 and 14 days post-transduction using primary staining with H84T. BanLec Ab 33 and secondary staining with AlexaFluor647-anti-rabbit F (ab) 2 (Jackson ImmunoResearch, West Grove, PA). All samples were acquired on FACSCelesta Cell Analyzer (BD) and analyzed with FlowJo software (v10.6.1). Cell sorting was performed on FACSMelody (BD).

Binding of Spike Protein to 293T.ACE2

Histidine (His)-tagged recombinant S-proteins: trimera (SPN—C52H9) and D614G trimera (SPN—C52H3) were purchased from ACROBiosystems (Newark, DE). A His-tagged receptor binding domain (RBD) was purchased from R&D Systems (10-500-CV-100, Minneapolis, MN). 293T, hACE2.293T, NK cells, and H84T-BanLec CAR-NK cells were coated with 50 ng of recombinant protein, then stained first with His antibody (R&D Systems), followed by PE-anti-mouse F (ab) 2 (R&D Systems) and analyzed using flow cytometry.

Western Blot

NK cells were lysed in RIPA lysis buffer with protease (complete) and phosphatase (PhosSTOP) inhibitor cocktails (Sigma-Aldrich, St. Louis, MO) on ice. Protein quantification was performed using Pierce BCA protein assay kit (cat #23228 and #23224, ThermoFisher) and iMark plate reader (Bio-Rad). Electrophoresis was conducted using Novex WedgeWell 10% Bis-Tris Mini Gels (Thermo Fisher) and protein transferred to polyvinylidene difluoride (PVDF) membrane. Western blot analysis was performed with the following antibodies: mouse anti-human CD247 (clone 1D4; BD Biosciences), mouse anti-human phosphory lated CD247 (pY142, clone K25-407.69; BD Biosciences), and rabbit anti-human H84T. BanLec Ab.[33] Membranes were stripped with Restore Western Blot Stripping Buffer (ThermoFisher) and used again for analysis with polyclonal rabbit anti-human glyceraldehyde 3-phosphate dehydrogenase (GAPDH) (Novus Biologicals, Littleton, CO).

Cytokine Secretion

NK cells were cultured with SARS-CoV-2-pseudovirus transduced hACE2.293T at a 1:1 ratio. Following 48 h of culture, supernatant was harvested and analyzed for interferon (IFN)γ or tumor necrosis factor (TNF)α using enzyme-linked immunosorbent assay (ELISA) kits (Quantikine; R&D Systems) according to the manufacturer's instruction. Conditions without pseudoviral particles were included as controls.

Cytotoxicity Assay

NK cells were co-cultured for 48 h with hACE2.293T.ffLuc at the indicated effector:target (E/T) ratios. D-luciferin was added to plate and BLI measured per well. Mean percentage of specific lysis of triplicate samples was calculated as 100*(spontaneous death–experimental death)/(spontaneous death–background). Spontaneous death was measured with control wells containing only target cells.

Statistical Analysis

All analyses were performed using GraphPad Prism Software (v9). For comparisons of 2 groups, unpaired t tests with Welch correction were used.

The following Table 1 lists all the plasmids of SARS-Related Coronavirus 2, Wuhan-Hu-1 Spike-Pseudotyped Lentiviral Kit that were used for generation of S-protein pseudotyped lentiviral particles. Plasmid name, type, inserted gene and catalog numbers as well as the microgram ratio used for transfection are listed.

TABLE 1

Plasmids in SARS-Related Coronavirus 2, Wuhan-Hu-1 Spike-Pseudotyped Lentiviral Kit

| Plasmid Name | Plasmid Type | Insert | BEI Resources Catalog Number | Microgram-ratio* |
|---|---|---|---|---|
| pHDM.CMV.Spike | Viral Entry Protein | Spike (S) glycoprotein | NR-52514 | 1.7 |
| pHAGE.CMV.ffLuc.IRES.ZSG | Lentiviral Backbone | Firefly Luciferase; ZsGreen | NR-52516 | 5 |
| pHDM.HIV gag-pol | Helper Plasmid | Gag; pol | NR-52517 | 1.1 |
| pHDM.HIV HIV tat1b | Helper Plasmid | Tat1b | NR-52518 | 1.1 |
| pRC.CMV.HIV rev1b | Helper Plasmid | Rev1b | NR-52519 | 1.1 |

*The ratio of micrograms of each plasmid used during transfection of 293T cells

Results

H84T-BanLec.4-1BB.ζ CAR is Stably Expressed in Human NK Cells

Figures 7A, 7B, 7C, 7D, 7E:
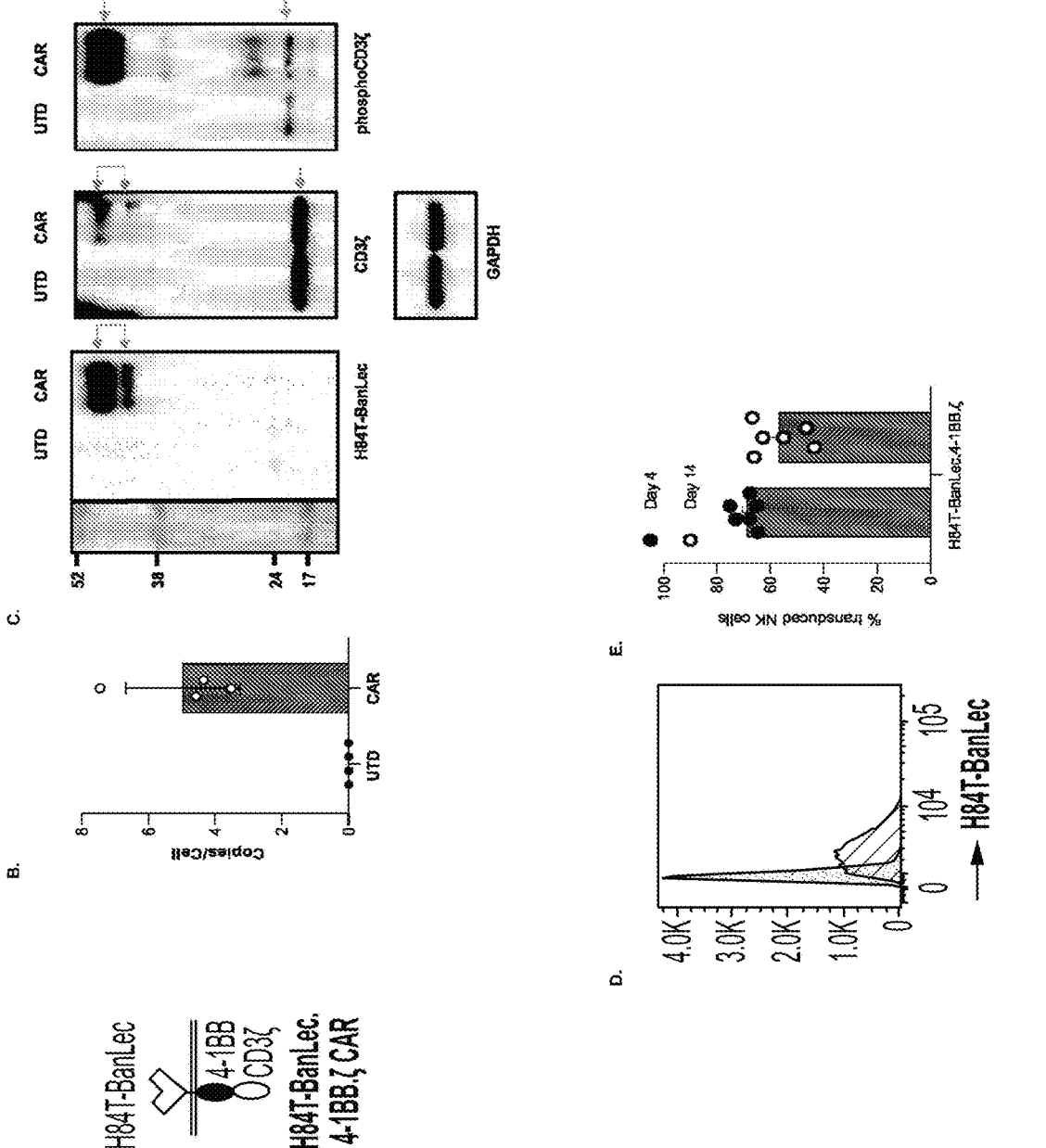
FIG. 7A. Schema defining CAR components.
FIG. 7B. Quantification of retroviral vector copy number (VCN) in transduced NK cells (CAR). Untransduced/unmodified (UTD) NK cells served as negative controls. n=4 NK cell donors FIG. 7C. Western blot detection of protein. UTD: untransduced NK cell lysate, CAR: H84T-BanLec CAR-NK cell lysate. Blue arrows: CAR, red arrows: endogenous zeta chain. GAPDH was used as a loading control.
FIG. 7D. Representative histogram showing detection of CAR-expression with flow cytometry. Gray: UTD, Blue: CAR-NK.
FIG. 7E. CAR detection on primary NK cell surface on days 4 and 14 post-transduction. Each dot representative of single transduction. n=6 total replicates from 4 independent NK cell donors.

We synthesized the H84T-banana lectin (H84T-BanLec) 32 sequence and subcloned this in place of the extracellular binding domain of an existing 4-1BB.ζ CAR.[36] Our complete CAR was comprised of H84T-BanLec, CD8a hinge and transmembrane domains, and the intracellular domains of 4-1BB and the CD35 chain (FIG. 7A). We produced replication incompetent retrovirus carrying our CAR sequence and used this to generate H84T-BanLec CAR NK cells. We measured a median of 4.5 integrated CAR copies per cell (range 3.5-7.45, FIG. 7B) and verified expression of CAR protein using Western blot (FIG. 7C). We observed constitutive CD35 phosphorylation of the CAR in our transduced cells, a finding that has previously been associated with CAR tonic signaling (FIG. 7C).37.38 We verified surface expression using flow cytometry and measured stable expression of the H84T-BanLec.4-1BB.ζ CAR on the surface of human NK cells (day 4 post-transduction: median [range], 67.5% CAR-positive [64.7-75%], day 14 post-transduction: 58.9% CAR-positive [43.6-66.7%], FIG. 7D, 7E).

hACE2-Expressing 293T Cells Bind SARS-CoV-2 Envelope Proteins

Figures 8A, 8B, 8C:
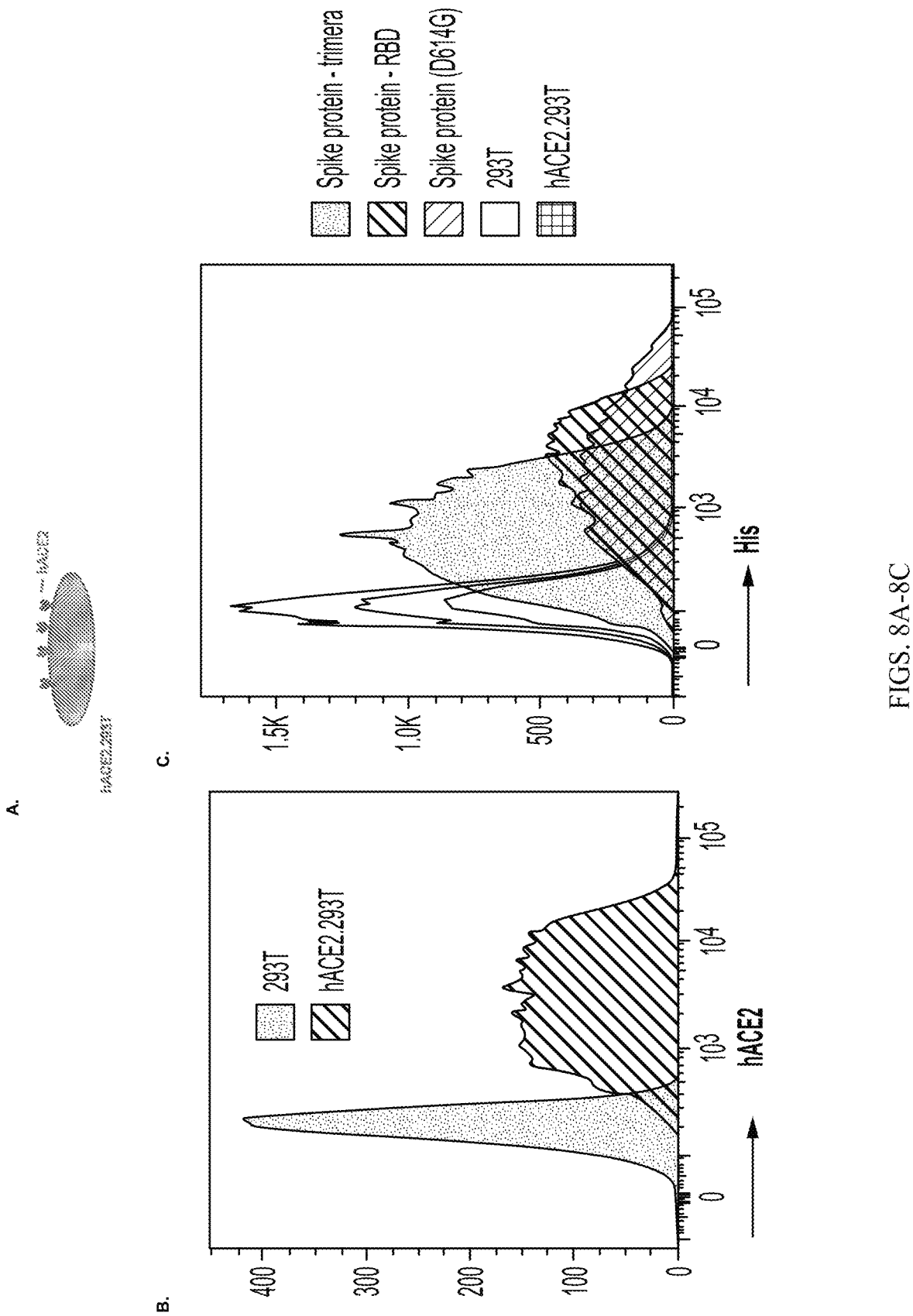
FIG. 8A. Schema of 293T engineered with hACE2.
FIG. 8B. Flow cytometric analysis of 293T expressing hACE2.
FIG. 8C. Detection of recombinant SARS-CoV-2 spike (S)-proteins bound to hACE2-expressing 293T cells. 293T without hACE2 expression used as negative control.

In order to model SARS-CoV-2 infection, we engineered 293T cells to constitutively express the ACE2 transmembrane protein (FIG. 8A, 8B). Human ACE2 is the binding partner for SARS-CoV-2.[24,39] We found that our hACE2.293T cells bound trimeric S-protein, the S-protein Receptor Binding Domain (RBD), and the D614G mutated[21] S-protein (FIG. 8C). Unmodified 293T cells did not bind S-proteins (FIG. 8C).

H84T-BanLec CAR-NK Cells Decrease Infectivity of Pseudoviral Particles

Figures 9A, 9B, 9C, 9D, 9E:
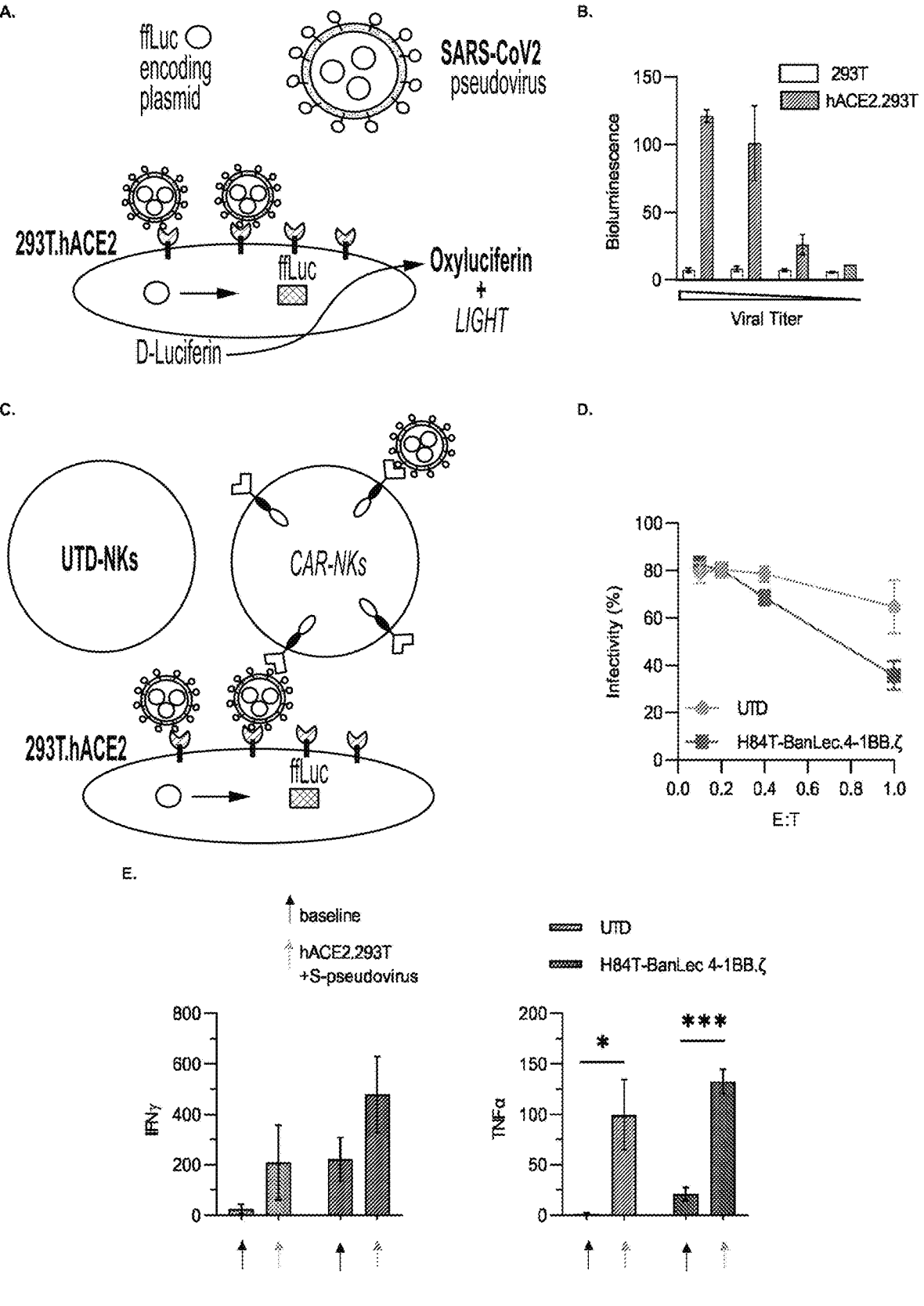
FIG. 9A. Schema of SARS-CoV-2 pseudovirus infection of hACE2.293T. Pseudoviral particles contain plasmids encoding fffLuc. Following viral entry, cells emit bioluminescence (BL) after D-Luciferin metabolism.
FIG. 9B. Measurement of target cell BL emission following transduction with S-protein pseudotyped virus carrying fffLuc reporter gene. Assay performed in triplicate.
FIG. 9C. Schematic representation of the BanLec-CAR NK cells blocking hACE2.293T infection.
FIG. 9D. NK cells plated with target cells (hACE2.293T)
FIG. 9E. Quantification (pg/mL) of IFNγ and TNFα present in culture media of NK cells at baseline and in co-culture with S-pseudotyped virus infected hACE2.293T (black: no target, red: co-culture: n=3 donors: Mean value+/−SEM; baseline vs. co-culture *p<0.05, ***p<0).

We used SARS-CoV-2 envelope pseudotyping of a replication deficient lentiviral vector[40] in order to evaluate whether H84T-BanLec CAR NK cells could reduce SARS-CoV-2 infectivity. We first tested hACE2.293T transduction using S-protein pseudotyped lentiviral particles. The pseudotyped vector carried firefly luciferase (ffLuc, FIG. 9A). Viral entry into cells was verified by quantification of bioluminescence (BL) emission following addition of D-Luciferin to virally transduced cells. Functionality of our assay was confirmed with observed BL emission of transduced hACE2.293T cells at all tested viral titrations. In contrast, 293T without ACE2 expression were not transduced, confirming specificity of viral binding and entry dependent on hACE2 (FIG. 9B).

Figures 10A, 10B, 10C:
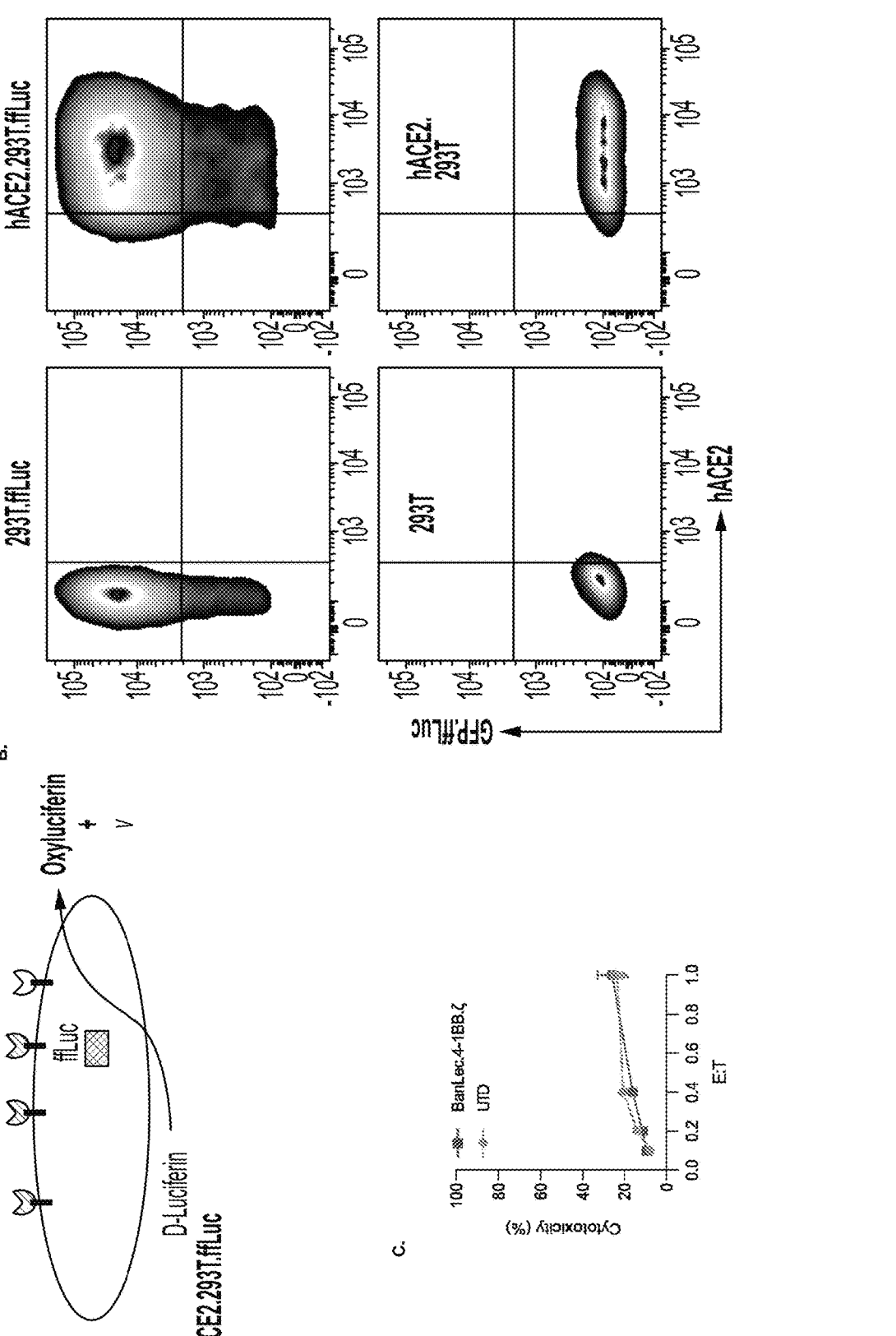
FIG. 10A. Schema of 293T engineered with both hACE2 and firely Luciferase (fffLuc).
FIG. 10B. Representative pseudo-color plots of 293T, hACE2.293T, 293T.fffLuc and hACE2.293T.fffLuc showing fffLuc and hACE2 expression.
FIG. 10C. NK cells were co-cultured at indicated E:T ratios with hACE2.293T.fffLuc.Bioluminescence (BL) measured following addition of D-luciferin and compared to control condition without effector cells as an indicator of target cell death (n=6, 2 separate experiments of 3 independent NK cell donors, each experiment performed in triplicate).

We next investigated whether H84T-BanLec CAR-NK cells could decrease S-protein mediated hACE2.293T transduction. NK cells (CAR-NKs or unmodified) were plated with hACE2.293T and freely circulating pseudoviral particles (FIG. 9C). We observed a reduction in SARS-CoV-2 pseudoviral infectivity of hACE2.293T cells when H84T-BanLec CAR-NK cells were present (FIG. 9D). Viral infectivity was reduced by both unmodified and H84T-CAR NK cells, but was more pronounced when CAR-NK cells were present (mean % pseudovirus infectivity+/−SEM of hACE2.293T in cocultures with unmodified NK vs. H84T-BanLec CAR-NK: 65+/−11% vs 35%+/−6% for 1:1 effector-to-target ratio, p=0.05:78+/−3% vs 68%+/−3% for 1:2.5 effector-to-target ratio, p=0.03; FIG. 9D). NK cells are reactive immune effector cells with cytotoxic potential against allogeneic targets. Therefore, we analyzed the killing capacity of NK cells against hACE2.293T cells to determine whether differences seen in infectivity could be explained by nonspecific target killing. There were no observed differences between CAR- and unmodified NK cell killing of hACE2.293T cells across a range of effector-to-target (E:T) ratios (mean % cytotoxicity+/−SEM of unmodified NK vs. H84T-BanLec CAR-NK: 23.5+/−2.7% vs. 25.9+/−7% in 1:1 E:T ratio, p=0.76:20.6+/−2% vs 16.1%+/−1% in 1:2.5 E:T ratio, p=0.1, see FIG. 10A-C). Moreover, the measured cytotoxicity of NK cells against 293T cells was roughly equivalent to the decrease in infectivity noted with unmodified NK cells, suggesting background cytotoxicity may have contributed to decreased viral entry in the absence of H84T-BanLec viral binding.

H84T-BanLec CAR-NK Cells are Strongly Activated by Virus

We evaluated the activation of NK cells in our pseudovirus assay. Both unmodified and H84T-BanLec CAR-NK cells were stimulated to secrete inflammatory mediators when co-cultured with pseudoviral particles and virally infected cells, including IFNγ (mean pg/ml+/−SEM of NK cells at baseline vs. in coculture with hACE2.293T and S-pseudovirus; unmodified NK: 24+/−11.6 vs. 209.4+/−86.1, p=0.16; CAR-NK: 221.9+/−49.7 vs. 479.2+/−86.7, p=0.07: n=3, FIG. 9E) and TNFα (unmodified NK: 1.2+/−0.6 vs. 99.3+/−20.1, p<0.05; CAR-NK: 20.9+/−3.6 vs. 132.6+/−6.8, p<0.001; n=3, FIG. 3E) CAR-NK cells showed overall higher cytokine secretion both at baseline and with viral stimulation.

Discussion

We have demonstrated successful generation of CAR-NK cells expressing extracellular H84T-BanLec linked to intracellular activation domains. Surface expression of the lectin-containing CAR was associated with tonic phosphorylation of CAR-CD35, validating its molecular functionality. We also engineered 293T cells to express ACE2, the SARS- CoV-2 receptor protein. We employed a model of SARS-CoV-2 infection that used a lentiviral vector pseudotyped with the S-protein. Virus infectivity was inhibited by H84T-BanLec CAR-NK cells. Moreover, our CAR-NK cells increased their secretion of IFNγ and TNFα after encountering virally infected cells. Increased inflammatory cytokine secretion was also observed to a lesser extent in unmodified NK cells, illustrating NK cell innate anti-viral potency.

CAR-T and CAR-NK cells are emerging immunotherapies with great promise. Typically, the expressed synthetic receptors are designed to bind surface protein. However, in our study, we designed a CAR making use of a unique extracellular moiety with binding properties dependent on target glycosylation. Targeting of glycoprotein, and specifically N-glycosylation products, with a CAR is rare. We believe that we describe the first CAR targeting the N-glycans dispersed on SARS-CoV-2 envelope proteins. Furthermore, to our knowledge this is the first lectin-based CAR designed and functionally tested in pre-clinical study. As lectins have evolved over millions of years to be highly potent and selective, the H84T-BanLec CAR represents an entirely new approach in that it targets aberrant glycosylation patterns in viral proteins. This methodology has the potential to be applied against cancer and other target cells as well.

During viral infections NK cells have a central role as first responders.[18] Viral infections can activate NK cells to produce IFNγ, TNFα, and other immunity-enhancing mediators that prime the adaptive immune response. 13.18.41 However, many viruses, including SARS-CoV-2, deploy strategies to evade NK cell surveillance.[42,43] CAR expression on the surface of NK cells can potentiate endogenous and antigen-specific activation and target killing.[44] This boosted function may render CAR-NK cells superior effectors in clearing circulating virus and virally infected cells. Appropriate antigen targeting and a precise combination of intracellular signaling domains are critical to direct CAR-NK cell behavior. We and others[44-47] have found 4-1BB and CD3ζ intracellular domains to be a good combination for NK cell activation. The vast majority of CAR constructs contain an extracellular single chain variable fragment derived from a monoclonal antibody for protein binding.[23] Instead, we used a lectin with specific binding to high mannose, an altered glycosylation pattern common to viral envelopes.[26,27,29,30,48] Our glycoprotein targeting mitigates the potential risk of antigen downregulation, a mechanism commonly employed by cancer cells to evade targeted immunotherapies.[49] CAR binding to envelope glycoproteins has the potential to not only neutralize and eliminate circulating virus, but also to clear infected cells with retained envelope proteins on their surface.

We observed decreased infectivity likely secondary to specific viral clearance by our CAR-NK cells. We also observed stable CAR.ζ phosphorylation and heightened activation of CAR-NK cells when compared to unmodified NK cells. This 4-1BB.ζ induced activation may prevent the dysfunction seen in circulating NK cells of patients with COVID-19.[11.50] similar to 4-1BB.ζ CAR mitigation of T cell exhaustion.[38] Ultimately, investigation of H84T-BanLec CAR-NK cell efficacy against wild-typeSARS-CoV-2 virus and in animal models of SARS-CoV-2 infection is needed.

Acute deterioration with COVID-19 requires emergency treatment options available at the ready. In comparison to T cells, which must be manufactured from autologous cells in order to prevent graft-versus-host disease, NK cells can be infused from allogeneic donors without this risk.[51,52] Aliquots of manufactured CAR-NK cells can be frozen and stored to establish a master cell bank capable of treating patients suffering from COVID-19 and in need of adequate immune function. Indeed, there are open clinical trials investigating the potential role of NK cell (NCT04280224, NCT04365101, NCT04634370, NCT04797975, NCT04900454) and CAR-NK cell (NCT04324996) adoptive transfer as COVID-19 treatments. Our findings support the hypothesis that CAR-NK cells expressing H84T-BanLec can mediate SARS-CoV-2 viral clearance. Taken together with the favorable innate antiviral characteristics and capability for allogeneic infusion of NK cells, H84T-BanLec CAR-NK cells may have promise as an effective cellular therapy against SARS-CoV-2 infection. Translation to the clinic could potentially impact days of hospitalization and survival rates of COVID-19 patients.

References: Example 4

1. Mohamadian, M., Chiti, H., Shoghli, A., Biglari, S., Parsamanesh, N., and Esmaeilzadeh, A. (2021). COVID-19: Virology, biology and novel laboratory diagnosis. J Gene Med 23, e3303. 10.1002/jgm.3303.
2. Baden, L. R., El Sahly, H. M., Essink, B., Kotloff, K., Frey, S., Novak, R., Diemert, D., Spector, S. A., Rouphael, N., Creech, C. B., McGettigan, J., et al. (2021). Efficacy and Safety of the mRNA-1273 SARS-CoV-2 Vaccine. N Engl J Med 384, 403-416. 10.1056/NEJMoa2035389.
3. Polack, F. P., Thomas, S., Kitchin, N., Absalon, J., Gurtman, A., Lockhart, S., Perez, J. L., Perez Marc, G., Moreira, E. D., Zerbini, C., Bailey, R., et al. (2020). Safety and Efficacy of the BNT162b2 mRNA Covid-19 Vaccine. N Engl J Med 383, 2603-2615. 10.1056/NEJMoa2034577.
4. Giamarellos-Bourboulis, E. J., Netea, M. G., Rovina, N., Akinosoglou, K., Antoniadou, A., Antonakos, N., Damoraki, G., Gkavogianni, T., Adami, M. E., Katsaounou, P., Ntaganou, M., et al. (2020). Complex Immune Dysregulation in COVID-19 Patients with Severe Respiratory Failure. Cell Host Microbe. 10.1016/j.chom.2020.04.009.
5. Wang, F., Nie, J., Wang, H., Zhao, Q., Xiong, Y., Deng, L., Song, S., Ma, Z., Mo, P., and Zhang, Y. (2020). Characteristics of peripheral lymphocyte subset alteration in COVID-19 pneumonia. J Infect Dis. 10.1093/infdis/jiaa150.
6. Qin, C., Zhou, L., Hu, Z., Zhang, S., Yang, S., Tao, Y., Xie, C., Ma, K., Shang, K., Wang, W., and Tian, D. S. (2020). Dysregulation of immune response in patients with COVID-19 in Wuhan, China. Clin Infect Dis. 10.1093/cid/ciaa248.
7. Files, J. K., Boppana, S., Perez, M. D., Sarkar, S., Lowman, K. E., Qin, K., Sterrett, S., Carlin, E., Bansal, A., Sabbaj, S., Long, D. M., et al. (2021). Sustained cellular immune dysregulation in individuals recovering from SARS-CoV-2 infection. J Clin Invest 131. 10.1172/JCI140491.
8. Cizmecioglu, A., Akay Cizmecioglu, H., Goktepe, M. H., Emsen, A., Korkmaz, C., Esenkaya Tasbent, F., Colkesen, F., and Artac, H. (2021). Apoptosis-induced T-cell lymphopenia is related to COVID-19 severity. J Med Virol 93, 2867-2874. 10.1002/jmv.26742.
9. Diao, B., Wang, C., Tan, Y., Chen, X., Liu, Y., Ning, L., Chen, L., Li, M., Liu, Y., Wang, G., Yuan, Z., et al. (2020). Reduction and Functional Exhaustion of T Cells in Patients With Coronavirus Disease 2019 (COVID-19). Front Immunol/1, 827. 10.3389/fimmu.2020.00827.

10. Liu, J., Li, S., Liu, J., Liang, B., Wang, X., Wang, H., Li, W., Tong, Q., Yi, J., Zhao, L., Xiong, L., et al. (2020). Longitudinal characteristics of lymphocyte responses and cytokine profiles in the peripheral blood of SARS-CoV-2 infected patients. EBioMedicine 55, 102763. 10.1016/j.ebiom.2020.102763.

11. Wilk, A. J., Rustagi, A., Zhao, N. Q., Roque, J., Martinez-Colon, G. J., McKechnie, J. L., Ivison, G. T., Ranganath, T., Vergara, R., Hollis, T., Simpson, L. J., et al. (2020). A single-cell atlas of the peripheral immune response in patients with severe COVID-19. Nat Med 26, 1070-1076. 10.1038/s41591-020-0944-y.

12. Hammer, Q., Ruckert, T., and Romagnani, C. (2018). Natural killer cell specificity for viral infections. Nat Immunol 19, 800-808. 10.1038/s41590-018-0163-6.

13. Lam, V. C., and Lanier, L. L. (2017). NK cells in host responses to viral infections. Curr Opin Immunol 44, 43-51. 10.1016/j.coi.2016.11.003.

14. Martinet, L., and Smyth, M. J. (2015). Balancing natural killer cell activation through paired receptors. Nat Rev Immunol 15, 243-254. 10.1038/nri3799.

15. Prager, I., and Watzl, C. (2019). Mechanisms of natural killer cell-mediated cellular cytotoxicity. J Leukoc Biol 105, 1319-1329. 10.1002/JLB.MR0718-269R.

16. Koutsakos, M., McWilliam, H. E. G., Aktepe, T. E., Fritzlar, S., Illing, P. T., Mifsud, N. A., Purcell, A. W., Rockman, S., Reading, P. C., Vivian, J. P., Rossjohn, J., et al. (2019). Downregulation of MHC Class I Expression by Influenza A and B Viruses. Front Immunol 10, 1158. 10.3389/fimmu.2019.01158.

17. Lodoen, M. B., and Lanier, L. L. (2005). Viral modulation of NK cell immunity. Nat Rev Microbiol 3, 59-69. 10.1038/nrmicro1066.

18. Brandstadter, J. D., and Yang, Y. (2011). Natural killer cell responses to viral infection. J Innate Immun 3, 274-279. 10.1159/000324176.

19. Ma, M., Badeti, S., Chen, C. H., Pinter, A., Jiang, Q., Shi, L., Zhou, R., Xu, H., Li, Q., Gause, W., and Liu, D. (2021). CAR-NK Cells Effectively Target the D614 and G614 SARS-CoV-2-infected Cells. bioRxiv. 10.1101/2021.01.14.426742.

20. Wei, J., Han, X., Bo, J., and Han, W. (2019). Target selection for CAR-T therapy. J Hematol Oncol 12, 62. 10.1186/s13045-019-0758-x.

21. Li, Q., Wu, J., Nie, J., Zhang, L., Hao, H., Liu, S., Zhao, C., Zhang, Q., Liu, H., Nie, L., Qin, H., et al. (2020). The Impact of Mutations in SARS-CoV-2 Spike on Viral Infectivity and Antigenicity. Cell 182, 1284-1294 e1289. 10.1016/j.cell.2020.07.012.

22. Harvey, W. T., Carabelli, A. M., Jackson, B., Gupta, R. K., Thomson, E. C., Harrison, E. M., Ludden, C., Reeve, R., Rambaut, A., Consortium, C.-G. U., Peacock, S. J., et al. (2021). SARS-CoV-2 variants, spike mutations and immune escape. Nat Rev Microbiol 19, 409-424. 10.1038/s41579-021-00573-0.

23. Guedan, S., Calderon, H., Posey, A. D., Jr., and Maus, M. V. (2019). Engineering and Design of Chimeric Antigen Receptors. Mol Ther Methods Clin Dev 12, 145-156. 10.1016/j.omtm.2018.12.009.

24. Li, W., Moore, M. J., Vasilieva, N., Sui, J., Wong, S. K., Berne, M. A., Somasundaran, M., Sullivan, J. L., Luzuriaga, K., Greenough, T. C., Choe, H., et al. (2003). Angiotensin-converting enzyme 2 is a functional receptor for the SARS coronavirus. Nature 426, 450-454. 10.1038/nature02145.

25. Wrapp, D., Wang, N., Corbett, K. S., Goldsmith, J. A., Hsieh, C. L., Abiona, O., Graham, B. S., and Mclellan, J. S. (2020). Cryo-EM structure of the 2019-nCOV spike in the prefusion conformation. Science 367, 1260-1263. 10.1126/science.abb2507.

26. Watanabe, Y., Allen, J. D., Wrapp, D., Mclellan, J. S., and Crispin, M. (2020). Site-specific analysis of the SARS-CoV-2 glycan shield. BioRxiv.

27. Zhang, Y., Zhao, W., Mao, Y., Wang, S., Zhong, Y., Su, T., Gong, M., Lu, X., Cheng, J., and Yang, H. (2020). Site-specific N-glycosylation Characterization of Recombinant SARS-CoV-2 Spike Proteins using High-Resolution Mass Spectrometry. bioRxiv.

28. Shajahan, A., Supekar, N. T., Gleinich, A. S., and Azadi, P. (2020). Deducing the N- and O-glycosylation profile of the spike protein of novel coronavirus SARS-CoV-2. bioRxiv.

29. Koshte, V. L., van Dijk, W., van der Stelt, M. E., and Aalberse, R. C. (1990). Isolation and characterization of BanLec-I, a mannoside-binding lectin from Musa paradisiac (banana). Biochem J 272, 721-726. 10.1042/bj2720721.

30. Hopper, J. T. S., Ambrose, S., Grant, O. C., Krumm, S. A., Allison, T. M., Degiacomi, M. T., Tully, M. D., Pritchard, L. K., Ozorowski, G., Ward, A. B., Crispin, M., et al. (2017). The Tetrameric Plant Lectin BanLec Neutralizes HIV through Bidentate to Viral Binding Specific Glycans. Structure 25, 773-782 e775. 10.1016/j.str.2017.03.015.

31. Swanson, M. D., Winter, H. C., Goldstein, I. J., and Markovitz, D. M. (2010). A lectin isolated from bananas is a potent inhibitor of HIV replication. J Biol Chem 285, 8646-8655. 10.1074/jbc.M109.034926.

32. Swanson, M. D., Boudreaux, D. M., Salmon, L., Chugh, J., Winter, H. C., Meagher, J. L., Andre, S., Murphy, P. V., Oscarson, S., Roy, R., King, S., et al. (2015). Engineering a therapeutic lectin by uncoupling mitogenicity from antiviral activity. Cell 163, 746-758. 10.1016/j.cell.2015.09.056.

33. Coves-Datson, E. M., King, S. R., Legendre, M., Gupta, A., Chan, S. M., Gitlin, E., Kulkarni, V. V., Pantaleon Garcia, J., Smee, D. F., Lipka, E., Evans, S. E., et al. (2020)). A molecularly engineered antiviral banana lectin inhibits fusion and is efficacious against influenza virus infection in vivo. Proc Natl Acad Sci USA/17, 2122-2132. 10.1073/pnas. 1915152117.

34. Mitchell, C. A., Ramessar, K., and O'Keefe, B. R. (2017). Antiviral lectins: Selective inhibitors of viral entry. Antiviral Res 142, 37-54. 10.1016/j.antiviral.2017.03.007.

35. Barton. C., Kouokam. J. C., Hurst. H., and Palmer. K. E. (2016). Pharmacokinetics of the Antiviral Lectin Griffithsin Administered by Different Routes Indicates Multiple Potential Uses. Viruses 8. 10.3390/v8120331.

36. Zolov. S. N., Rietberg. S. P., and Bonifant. C. L. (2018). Programmed cell death protein 1 activation preferentially inhibits CD28.CAR-T cells. Cytotherapy 20. 1259-1266. 10.1016/j.jcyt.2018.07.005.

37. Eyquem. J., Mansilla-Soto. J., Giavridis. T., van der Stegen, S., Hamieh. M., Cunanan. K. M., Odak. A., Gonen. M., and Sadelain, M. (2017). Targeting a CAR to the TRAC locus with CRISPR/Cas9 enhances tumour rejection. Nature 543. 113-117. 10.1038/nature21405.

38. Long. A. H., Haso. W. M., Shern. J. F., Wanhainen. K. M., Murgai. M., Ingaramo. M., Smith. J. P., Walker. A. J., Kohler. M. E., Venkateshwara. V. R., Kaplan. R. N., et al. (2015). 4-1BB costimulation ameliorates T cell exhaustion induced by tonic signaling of chimeric antigen receptors. Nat Med 21. 581-590. 10.1038/nm.3838.

39. Gheblawi. M., Wang. K., Viveiros. A., Nguyen. Q., Zhong. J. C., Turner, A. J., Raizada. M. K., Grant. M. B., and Oudit. G. Y. (2020)). Angiotensin-Converting Enzyme 2: SARS-CoV-2 Receptor and Regulator of the Renin-Angiotensin System: Celebrating the 20th Anniversary of the Discovery of ACE2. Circ Res 126. 1456-1474. 10.1161/CIRCRESAHA. 120.317015.

40. Crawford. K. H. D., Eguia. R., Dingens. A. S., Loes. A. N., Malone. K. D., Wolf. C. R., Chu. H. Y., Tortorici. M. A., Veesler. D., Murphy. M., Pettie. D., et al. (2020). Protocol and Reagents for Pseudotyping Lentiviral Particles with SARS-CoV-2 Spike Protein for Neutralization Assays. Viruses 12. 10.3390/v12050513.

41. Biron. C. A., Nguyen. K. B., Pien. G. C., Cousens. L. P., and Salazar-Mather. T. P. (1999). Natural killer cells in antiviral defense: function and regulation by innate cytokines. Annu Rev Immunol 17. 189-220. 10.1146/annurev.immunol. 17.1.189.

42. Orange. J. S., Fassett. M. S., Koopman. L. A., Boyson. J. E., and Strominger. J. L. (2002). Viral evasion of natural killer cells. Nat Immunol 3. 1006-1012. 10.1038/ni1102-1006.

43. Taefehshokr. N., Taefehshokr. S., Hemmat. N., and Heit. B. (2020). Covid-19: Perspectives on Innate Immune Evasion. Front Immunol 11. 580641. 10.3389/fimmu.2020.580641.

44. Xu. Y., Liu. Q., Zhong. M., Wang. Z., Chen. Z., Zhang. Y., Xing. H., Tian. Z., Tang. K., Liao. X., Rao. Q., et al. (2019). 2B4 costimulatory domain enhancing cytotoxic ability of anti-CD5 chimeric antigen receptor engineered natural killer cells against T cell malignancies. J Hematol Oncol 12. 49. 10.1186/s13045-019-0732-7.

45. Imai. C., Iwamoto. S., and Campana. D. (2005). Genetic modification of primary natural killer cells overcomes inhibitory signals and induces specific killing of leukemic cells. Blood 106. 376-383. 10.1182/blood-2004-12-4797.

46. Shimasaki. N., Fujisaki. H., Cho. D., Masselli. M., Lockey. T., Eldridge. P., Leung. W., and Campana. D. (2012). A clinically adaptable method to enhance the cytotoxicity of natural killer cells against B-cell malignancies. Cytotherapy 14. 830-840. 10.3109/14653249.2012.671519.

47. Chu, Y., Hochberg, J., Yahr, A., Ayello, J., van de Ven, C., Barth, M., Czuczman, M., and Cairo, M. S. (2015). Targeting CD20+ Aggressive B-cell Non-Hodgkin Lymphoma by Anti-CD20 CAR mRNA-Modified Expanded Natural Killer Cells In Vitro and in NSG Mice. Cancer Immunol Res 3, 333-344. 10.1158/2326-6066.CIR-14-0114.

48. Asif Shajahan, Nitin T. Supekar, Anne S. Gleinich, and Azadi, P. (2020). Deducing the N- and O-glycosylation profile of the spike protein of novel coronavirus SARS-CoV-2.

49. Bonifant, C. L., and Tasian, S. K. (2020). The future of cellular immunotherapy for childhood leukemia. Curr Opin Pediatr 32, 13-25. 10.1097/MOP.0000000000000866.

50. Zheng, M., Gao, Y., Wang, G., Song, G., Liu, S., Sun, D., Xu, Y., and Tian, Z. (2020). Functional exhaustion of antiviral lymphocytes in COVID-19 patients. Cell Mol Immunol 17, 533-535. 10.1038/s41423-020-0402-2.

51. Liu, E., Marin, D., Banerjee, P., Macapinlac, H. A., Thompson, P., Basar, R., Nassif Kerbauy, L., Overman, B., Thall, P., Kaplan, M., Nandivada, V., et al. (2020). Use of CAR-Transduced Natural Killer Cells in CD19-Positive Lymphoid Tumors. N Engl J Med 382, 545-553. 10.1056/NEJMoa1910607.

52. Ciurea, S. O., Schafer, J. R., Bassett, R., Denman, C. J., Cao, K., Willis, D., Rondon, G., Chen, J., Soebbing, D., Kaur, I., Gulbis, A., et al. (2017). Phase 1 clinical trial using mbIL21 ex vivo-expanded donor-derived NK cells after haploidentical transplantation. Blood 130, 1857-1868. 10.1182/blood-2017-05-785659.

53. Vera, J., Savoldo, B., Vigouroux, S., Biagi, E., Pule, M., Rossig, C., Wu, J., Heslop, H. E., Rooney, C. M., Brenner, M. K., and Dotti, G. (2006). T lymphocytes redirected against the kappa light chain of human immunoglobulin efficiently kill mature B lymphocyte-derived malignant cells. Blood 108, 3890-3897. 10.1182/blood-2006-04-017061.

54. Bueler, H., and Mulligan, R. C. (1996). Induction of antigen-specific tumor immunity by genetic and cellular vaccines against MAGE: enhanced tumor protection by coexpression of granulocyte-macrophage colony-stimulating factor and B7-1. Mol Med 2. 545-555.

55. Kunz. A., Gern, U., Schmitt, A., Neuber, B., Wang. L., Huckelhoven-Krauss, A., Michels, B., Hofmann, S., Muller-Tidow, C., Dreger, P., Schmitt, M., et al. (2020). Optimized Assessment of qPCR-Based Vector Copy Numbers as a Safety Parameter for GMP-Grade CAR T Cells and Monitoring of Frequency in Patients. Mol Ther Methods Clin Dev 17, 448-454. 10.1016/j.omtm.2020.02.003.

56. Murphy, G. J., Mostoslavsky, G., Kotton, D. N., and Mulligan, R. C. (2006). Exogenous control of mammalian gene expression via modulation of translational termination. Nat Med 12, 1093-1099. 10.1038/nm1376.

Abbreviations

ACE2, angiotensin-converting enzyme 2
BanLec, Banana Lectin
BL, bioluminescence
CAR, chimeric antigen receptor
CAR-NK, chimeric antigen receptor natural killer
COVID-19, coronavirus disease 2019
E:T, effector-to-target
ffLuc, firefly luciferase
H84T-BanLec, H84T banana lectin
His, histidine
NK, natural killer
RLU, reactive light units
RBD, receptor binding domain
S-protein, spike protein
SARS-CoV-2, severe acute respiratory syndrome coronavirus 2
UTD, untransduced/unmodified
VCN, vector copy number

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All references, e.g., U.S. patents, U.S. patent application publications, PCT patent applications designating the U.S., published foreign patents and patent applications cited herein are incorporated herein by reference in their entireties. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

While this invention has been particularly shown and described with references to preferred embodiments thereof, it will be understood by those skilled in the art that various changes in form and details may be made therein without departing from the scope of the invention encompassed by the appended claims.

What is claimed is:

1. An engineered immune cell expressing a chimeric antigen receptor (CAR) polypeptide comprising an extracellular banana lectin (BanLec) domain, wherein the CAR polypeptide comprises an amino acid sequence having at least 70, 75, 80, 85, 90, 91, 92, 93, 94, 95, 96, 97, 98, 99 or 100% identity with an amino acid sequence of SEQ ID NO: 6, SEQ ID NO: 7, SEQ ID NO:9, or SEQ ID NO:11.

2. The engineered immune cell of claim 1, wherein the CAR polypeptide comprises an amino acid sequence having 95, 96, 97, 98, 99 or 100% identity with an amino acid sequence of SEQ ID NO: 6, SEQ ID NO:7, SEQ ID NO:9, orcv SEQ ID NO:11.

3. The engineered immune cell of claim 1, wherein the CAR polypeptide comprises an amino acid sequence having 99 or 100% identity with the amino acid sequence of SEQ ID NO:6, SEQ ID NO:7, SEQ ID NO:9, or SEQ ID NO:11.

4. A method of preventing or treating a viral infection, the method comprising: administering to a subject suffering from or susceptible to a viral infection an effective amount of immune cells of claim 1.

5. The method of claim 4, wherein the viral infection comprises a coronavirus infection.

6. The method of claim 4, wherein the viral infection comprises severe acute respiratory syndrome coronavirus 2 (SARS-COV-2).

7. The method of claim 4, wherein the viral infection comprises a retrovirus infection.

8. The method of claim 4, further comprising administering an additional, distinct antiviral agent to the subject.

9. The method of claim 4, wherein the mammal is a human.

10. The method of claim 4, wherein the cells are administered as a pharmaceutical composition comprising a pharmaceutically acceptable carrier.

11. A method of preventing or treating a viral infection, the method comprising: providing a composition comprising a population of engineered immune cells of claim 1, administering the composition to the subject, and thereby preventing or treating the viral infection.

12. A kit comprising a population of engineered immune cells of claim 1.

13. A method of preventing or treating cells that have been infected by a virus, the method comprising: administering to virally infected cells an effective amount of immune cells of any one of claim 1.

14. A method of treating cells that have been infected by a virus, the method comprising: providing a composition comprising a population of engineered immune cells of claim 1, administering the composition to virally infected cells, and thereby preventing or treating the viral infection in the cells.

15. An engineered immune cell expressing a chimeric antigen receptor (CAR) polypeptide comprising an extracellular banana lectin (BanLec) domain, wherein the CAR polypeptide is encoded by a sequence having at least 70, 75, 80, 85, 90, 91, 92, 93, 94, 95, 96, 97, 98, 99 or 100% identity with SEQ ID NO: 8 or SEQ ID NO: 10.

16. The engineered immune cell of claim 15, wherein the CAR polypeptide is encoded by a sequence having 95, 96, 97, 98, 99 or 100% identity with SEQ ID NO: 8 or SEQ ID NO:10.

17. The engineered immune cell of claim 15, wherein the CAR polypeptide is encoded by a sequence having 99 or 100% identity with SEQ ID NO:8 or SEQ ID NO:10.

* * * * *

SEQUENCE LISTING

<160> NUMBER OF SEQ ID NOS: 13

<210> SEQ ID NO 1
<211> LENGTH: 141
<212> TYPE: PRT
<213> ORGANISM: Musa acuminata

<400> SEQUENCE: 1

```
Met Asn Gly Ala Ile Lys Val Gly Ala Trp Gly Gly Asn Gly Gly Ser
1               5                   10                  15

Ala Phe Asp Met Gly Pro Ala Tyr Arg Ile Ile Ser Val Lys Ile Phe
            20                  25                  30

Ser Gly Asp Val Val Asp Gly Val Asp Val Thr Phe Thr Tyr Tyr Gly
        35                  40                  45

Lys Thr Glu Thr Arg His Tyr Gly Gly Ser Gly Gly Thr Pro His Glu
    50                  55                  60

Ile Val Leu Gln Glu Gly Glu Tyr Leu Val Gly Met Ala Gly Glu Val
65                  70                  75                  80

Ala Asn Tyr His Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
            100                 105                 110

Ser Leu Pro Ile Ala Ala Gly Lys Ile Ser Gly Phe Phe Gly Arg Gly
        115                 120                 125

Gly Lys Phe Leu Asp Ala Ile Gly Val Tyr Leu Glu Pro
    130                 135                 140
```

<210> SEQ ID NO 2
<211> LENGTH: 575
<212> TYPE: DNA
<213> ORGANISM: Musa acuminata

<400> SEQUENCE: 2

```
atgaacggag cgatcaaggt gggagcatgg ggagggaacg gagggtcggc cttcgacatg       60
ggacctgctt atcgtatcat cagcgtcaag attttttccg gagacgtggt cgacgccgtg      120
gacgtcacct tcacctacta cgggaagacg gagacccgac acttcggtgg cagcggtggt      180
actccccacg aggtttgcat cactaccaat ctcaaagctc atagctgact gcagattaat      240
ggcttctact tggatgcaga ttgttctgca ggagggcgaa tatctggtgg gaatgaaggg      300
agaatttggt aactaccatg gagtggtggt ggtggggaag cttggcttca gcaccaacaa      360
gaaatcctac ggacctttcg gcaacacggg agggactccc ttctcccttc ctatagcagc      420
aggcaagatc tctggcttct tcggccgtgg cggcgatttt attgacgcca ttgggggtcta      480 cttggagcca taattggcca ctgcagtaaa tcacaagagt tgctatgtgc tacttggagt      540
gatgagatga agaatgtctg caataaatgg atcgg                                 575
```

<210> SEQ ID NO 3
<211> LENGTH: 141
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 3

Met Asn Gly Ala Ile Lys Val Gly Ala Trp Gly Gly Asn Gly Gly Ser
1               5                   10                  15

Ala Phe Asp Met Gly Pro Ala Tyr Arg Ile Ile Ser Val Lys Ile Phe
                20                  25                  30

Ser Gly Asp Val Val Asp Gly Val Asp Val Thr Phe Thr Tyr Tyr Gly
            35                  40                  45

Lys Thr Glu Thr Arg His Tyr Gly Gly Ser Gly Gly Thr Pro His Glu
        50                  55                  60

Ile Val Leu Gln Glu Gly Glu Tyr Leu Val Gly Met Ala Gly Glu Val
65                  70                  75                  80

Ala Asn Tyr Thr Gly Ala Val Val Leu Gly Lys Leu Gly Phe Ser Thr
                85                  90                  95

Asn Lys Lys Ala Tyr Gly Pro Phe Gly Asn Thr Gly Gly Thr Pro Phe
                100                 105                 110

Ser Leu Pro Ile Ala Ala Gly Lys Ile Ser Gly Phe Phe Gly Arg Gly
            115                 120                 125

Gly Lys Phe Leu Asp Ala Ile Gly Val Tyr Leu Glu Pro
        130                 135                 140

<210> SEQ ID NO 4
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
aatggcgcta tcaaagttgg agcctggggc ggcaatggcg gcagcgcttt tgatatgggc      60
cctgcctacc ggatcatcag cgtgaagatc tttagcggcg acgtggtgga tggcgtggac     120
gtgaccttta cctactacgg caagaccgag acacggcact atggcggaag cggaggaaca     180
cctcacgaga tcgttctgca agagggcgag tacctcgttg gaatggctgg cgaggtggcc     240
aactatacag gtgctgtggt gctgggcaag ctgggcttca gcaccaacaa gaaggcctac     300
ggacccttcg gcaataccgg cggcacacct tttagcctgc ctattgccgc cggaatcagc     360
ggcttttttg gcagaggcgg caagttcctg gatgccatcg gagtgtatct ggaaccc       417

<210> SEQ ID NO 5
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asn Gly Ala Ile Lys Val Gly Ala Trp Gly Gly Asn Gly Gly Ser Ala
1               5                   10                  15

Phe Asp Met Gly Pro Ala Tyr Arg Ile Ile Ser Val Lys Ile Phe Ser
                20                  25                  30

Gly Asp Val Val Asp Gly Val Asp Val Thr Phe Thr Tyr Tyr Gly Lys
            35                  40                  45

Thr Glu Thr Arg His Tyr Gly Gly Ser Gly Gly Thr Pro His Glu Ile
```

-continued

```
          50                   55                   60
Val Leu Gln Glu Gly Glu Tyr Leu Val Gly Met Ala Gly Glu Val Ala
65                   70                   75                   80

Asn Tyr Thr Gly Ala Val Val Leu Gly Lys Leu Gly Phe Ser Thr Asn
                85                   90                   95

Lys Lys Ala Tyr Gly Pro Phe Gly Asn Thr Gly Gly Thr Pro Phe Ser
                100                  105                  110

Leu Pro Ile Ala Ala Gly Ile Ser Gly Phe Phe Gly Arg Gly Gly Lys
        115                  120                  125

Phe Leu Asp Ala Ile Gly Val Tyr Leu Glu Pro
        130                  135
```

<210> SEQ ID NO 6
<211> LENGTH: 383
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Met Asp Trp Ile Trp Arg Ile Leu Phe Leu Val Gly Ala Ala Thr Gly
1               5                   10                  15

Ala His Ser Asn Gly Ala Ile Lys Val Gly Ala Trp Gly Gly Asn Gly
                20                  25                  30

Gly Ser Ala Phe Asp Met Gly Pro Ala Tyr Arg Ile Ile Ser Val Lys
            35                  40                  45

Ile Phe Ser Gly Asp Val Val Asp Gly Val Asp Val Thr Phe Thr Tyr
    50                  55                  60

Tyr Gly Lys Thr Glu Thr Arg His Tyr Gly Gly Ser Gly Gly Thr Pro
65                  70                  75                  80

His Glu Ile Val Leu Gln Glu Gly Glu Tyr Leu Val Gly Met Ala Gly
                85                  90                  95

Glu Val Ala Asn Tyr Thr Gly Ala Val Val Leu Gly Lys Leu Gly Phe
            100                 105                 110

Ser Thr Asn Lys Lys Ala Tyr Gly Pro Phe Gly Asn Thr Gly Gly Thr
        115                 120                 125

Pro Phe Ser Leu Pro Ile Ala Ala Gly Ile Ser Gly Phe Phe Gly Arg
        130                 135                 140

Gly Gly Lys Phe Leu Asp Ala Ile Gly Val Tyr Leu Glu Pro Gly Gly
145                 150                 155                 160

Gly Gly Ser Thr Thr Thr Pro Ala Pro Arg Pro Pro Thr Pro Ala Pro
                165                 170                 175

Thr Ile Ala Ser Gln Pro Leu Ser Leu Arg Pro Glu Ala Cys Arg Pro
            180                 185                 190

Ala Ala Gly Gly Ala Val His Thr Arg Gly Leu Asp Phe Ala Cys Asp
            195                 200                 205

Ile Tyr Ile Trp Ala Pro Ala Gly Thr Cys Gly Val Leu Leu Leu Ser
    210                 215                 220

Leu Val Ile Thr Leu Tyr Cys Lys Arg Gly Arg Lys Lys Leu Leu Tyr
225                 230                 235                 240

Ile Phe Lys Gln Pro Phe Met Arg Pro Val Gln Thr Thr Gln Glu Glu
                245                 250                 255

Asp Gly Cys Ser Cys Arg Phe Pro Glu Glu Glu Glu Gly Gly Cys Glu
            260                 265                 270
```

-continued

```
Leu Arg Val Lys Phe Ser Arg Ser Ala Asp Ala Pro Ala Tyr Gln Gln
        275             280             285

Gly Gln Asn Gln Leu Tyr Asn Glu Leu Asn Leu Gly Arg Arg Glu Glu
        290             295             300

Tyr Asp Val Leu Asp Lys Arg Arg Gly Arg Asp Pro Glu Met Gly Gly
305             310             315             320

Lys Arg Lys Asn Pro Gln Glu Gly Leu Tyr Asn Glu Leu Gln Lys Asp
                325             330             335

Lys Met Ala Glu Ala Tyr Ser Glu Ile Gly Met Lys Gly Glu Arg Arg
            340             345             350

Arg Gly Lys Gly His Asp Gly Leu Tyr Gln Gly Leu Ser Thr Ala Thr
        355             360             365

Lys Asp Thr Tyr Asp Ala Leu His Met Gln Ala Leu Pro Pro Arg
        370             375             380

<210> SEQ ID NO 7
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Trp Ile Trp Arg Ile Leu Phe Leu Val Gly Ala Ala Thr Gly
1               5               10              15

Ala His Ser Asn Gly Ala Ile Lys Val Gly Ala Trp Gly Gly Asn Gly
            20              25              30

Gly Ser Ala Phe Asp Met Gly Pro Ala Tyr Arg Ile Ile Ser Val Lys
        35              40              45

Ile Phe Ser Gly Asp Val Val Asp Gly Val Asp Val Thr Phe Thr Tyr
    50              55              60

Tyr Gly Lys Thr Glu Thr Arg His Tyr Gly Gly Ser Gly Gly Thr Pro
65              70              75              80

His Glu Ile Val Leu Gln Glu Gly Glu Tyr Leu Val Gly Met Ala Gly
                85              90              95

Glu Val Ala Asn Tyr Thr Gly Ala Val Val Leu Gly Lys Leu Gly Phe
            100             105             110

Ser Thr Asn Lys Lys Ala Tyr Gly Pro Phe Gly Asn Thr Gly Gly Thr
        115             120             125

Pro Phe Ser Leu Pro Ile Ala Ala Gly Ile Ser Gly Phe Phe Gly Arg
    130             135             140

Gly Gly Lys Phe Leu Asp Ala Ile Gly Val Tyr Leu Glu Pro Gly Gly
145             150             155             160

Gly Gly Ser Gln Asp Cys Gln Asn Ala His Gln Glu Phe Arg Phe Trp
                165             170             175

Pro Phe Leu Val Ile Ile Val Ile Leu Ser Ala Leu Phe Leu Gly Thr
            180             185             190

Leu Ala Cys Phe Cys Val Trp Arg Arg Lys Arg Lys Glu Lys Gln Ser
        195             200             205

Glu Thr Ser Pro Lys Glu Phe Leu Thr Ile Tyr Glu Asp Val Lys Asp
        210             215             220

Leu Lys Thr Arg Arg Asn His Glu Gln Glu Gln Thr Phe Pro Gly Gly
225             230             235             240

Gly Ser Thr Ile Tyr Ser Met Ile Gln Ser Gln Ser Ser Ala Pro Thr
                245             250             255
```

-continued

```
Ser Gln Glu Pro Ala Tyr Thr Leu Tyr Ser Leu Ile Gln Pro Ser Arg
            260                 265                 270

Lys Ser Gly Ser Arg Lys Arg Asn His Ser Pro Ser Phe Asn Ser Thr
            275                 280                 285

Ile Tyr Glu Val Ile Gly Lys Ser Gln Pro Lys Ala Gln Asn Pro Ala
            290                 295                 300

Arg Leu Ser Arg Lys Glu Leu Glu Asn Phe Asp Val Tyr Ser Gly Ala
305                 310                 315                 320

Gly Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
            355                 360                 365

Lys Pro Gln Arg Arg Lys Asn Pro Gln Glu Gly Leu Tyr Asn Glu Leu
            370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
            420                 425                 430

Pro Arg
```

```
<210> SEQ ID NO 8
<211> LENGTH: 1305
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggactgga tctggcgcat cctgtttctt gtgggagccg ccacaggcgc ccatagcaat      60
ggcgctatca aagttggagc ctggggcggc aatggcggca gcgcttttga tatgggccct     120
gcctaccgga tcatcagcgt gaagatcttt agcggcgacg tggtggatgg cgtggacgtg     180
acctttacct actacggcaa gaccgagaca cggcactatg cggaagcgg aggaacacct     240 cacgagatcg ttctgcaaga gggcgagtac ctcgttggaa tggctggcga ggtggccaac     300
tatacaggtg ctgtggtgct gggcaagctg ggcttcagca ccaacaagaa ggcctacgga     360
cccttcggca ataccggcgg cacacctttt agcctgccta ttgccgccgg aatcagcggc     420 tttttttggca gaggcggcaa gttcctggat gccatcggag tgtatctgga acccggaggg     480
ggcggatccc aggattgcca gaatgcccac aagagttcc ggttctggcc cttcctggtc     540
atcatcgtga tcctgagcgc cctgttcctg ggcaccctgg cctgtttttg cgtgtggcgc     600
agaaagcgca agagaagca gagcgagaca agccccaaag agttcctgac catctacgag     660
gacgtgaagg acctgaaaac ccggcggaac cacgagcaag agcagacctt tcctggcggc     720
ggaagcacca tctacagcat gatccagagc cagagcagcg ccctacaag ccaagagcct     780 gcctacacac tgtactccct gatccagcct agcagaaaga gcggcagccg gaagagaaat     840
cacagcccca gcttcaacag cacgatctac gaagtgatcg gcaagagcca gccaaaggct     900
cagaaccctg ccagactgag ccggaaagag ctggaaaact cgacgtgta ctctggggcc     960
```

-continued

```
ggcagagtga agttcagcag atcagccgat gctcccgcct atcagcaggg ccagaaccag   1020
ctgtacaacg agctgaacct ggggagaaga gaagagtacg acgtgctgga caagcggaga   1080
ggcagagatc ctgagatggg cggaaagccc cagcggagaa agaatcctca agagggcctg   1140
tataatgagc tgcagaaaga caagatggcc gaggcctaca gcgagatcgg aatgaagggc   1200
gagcgcagaa gaggcaaggg acacgatgga ctgtaccagg gcctgagcac cgccaccaag   1260 gataccctatg atgccctgca catgcaggcc ctgcctccaa gatga                  1305
```

<210> SEQ ID NO 9
<211> LENGTH: 434
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Asp Trp Ile Trp Arg Ile Leu Phe Leu Val Gly Ala Ala Thr Gly
1               5                   10                  15

Ala His Ser Asn Gly Ala Ile Lys Val Gly Ala Trp Gly Gly Asn Gly
                20                  25                  30

Gly Ser Ala Phe Asp Met Gly Pro Ala Tyr Arg Ile Ile Ser Val Lys
            35                  40                  45

Ile Phe Ser Gly Asp Val Val Asp Gly Val Asp Val Thr Phe Thr Tyr
        50                  55                  60

Tyr Gly Lys Thr Glu Thr Arg His Tyr Gly Gly Ser Gly Gly Thr Pro
65                  70                  75                  80

His Glu Ile Val Leu Gln Glu Gly Glu Tyr Leu Val Gly Met Ala Gly
                85                  90                  95

Glu Val Ala Asn Tyr Thr Gly Ala Val Val Leu Gly Lys Leu Gly Phe
                100                 105                 110

Ser Thr Asn Lys Lys Ala Tyr Gly Pro Phe Gly Asn Thr Gly Gly Thr
            115                 120                 125

Pro Phe Ser Leu Pro Ile Ala Ala Gly Ile Ser Gly Phe Phe Gly Arg
        130                 135                 140

Gly Gly Lys Phe Leu Asp Ala Ile Gly Val Tyr Leu Glu Pro Gly Gly
145                 150                 155                 160

Gly Gly Ser Gln Asp Cys Gln Asn Ala His Gln Glu Phe Arg Phe Trp
                165                 170                 175

Pro Phe Leu Val Ile Ile Val Ile Leu Ser Ala Leu Phe Leu Gly Thr
                180                 185                 190

Leu Ala Cys Phe Cys Val Trp Arg Arg Lys Arg Lys Glu Lys Gln Ser
            195                 200                 205

Glu Thr Ser Pro Lys Glu Phe Leu Thr Ile Tyr Glu Asp Val Lys Asp
            210                 215                 220

Leu Lys Thr Arg Arg Asn His Glu Gln Glu Gln Thr Phe Pro Gly Gly
225                 230                 235                 240

Gly Ser Thr Ile Tyr Ser Met Ile Gln Ser Gln Ser Ser Ala Pro Thr
                245                 250                 255

Ser Gln Glu Pro Ala Tyr Thr Leu Tyr Ser Leu Ile Gln Pro Ser Arg
            260                 265                 270

Lys Ser Gly Ser Arg Lys Arg Asn His Ser Pro Ser Phe Asn Ser Thr
            275                 280                 285

Ile Tyr Glu Val Ile Gly Lys Ser Gln Pro Lys Ala Gln Asn Pro Ala
        290                 295                 300
```

```
Arg Leu Ser Arg Lys Glu Leu Glu Asn Phe Asp Val Tyr Ser Gly Ala
305                 310                 315                 320

Gly Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
                340                 345                 350

Tyr Asp Val Leu Asp Lys Arg Arg Gly Arg Asp Pro Glu Met Gly Gly
        355                 360                 365

Lys Pro Gln Arg Arg Lys Asn Pro Gln Glu Gly Leu Tyr Asn Glu Leu
    370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
                420                 425                 430

Pro Arg
```

```
<210> SEQ ID NO 10
<211> LENGTH: 1152
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atggactgga tctggcgcat cctgtttctt gtgggagccg ccacaggcgc ccatagcaat      60
ggcgctatca aagttggagc ctggggcggc aatggcggca cgcttttga tatgggccct     120 gcctaccgga tcatcagcgt gaagatcttt agcggcgacg tggtggatgg cgtggacgtg     180
acctttacct actacggcaa gaccgagaca cggcactatg cggaagcgg aggaacacct     240 cacgagatcg ttctgcaaga gggcgagtac ctcgttggaa tggctggcga ggtggccaac     300
tatacaggtg ctgtggtgct gggcaagctg ggcttcagca ccaacaagaa ggcctacgga     360
cccttcggca ataccggcgg cacacctttt agcctgccta ttgccgccgg aatcagcggc     420 tttttttggca gaggcggcaa gttcctggat gccatcggag tgtatctgga acccggaggg     480
ggcggatcca caacaacccc tgcccccaga cctcctaccc cagcccctac aattgccagc     540
cagcctctga gcctgaggcc cgaggcttgt agacctgctg ctggcggagc cgtgcacacc     600
agaggactgg atttcgcctg cgacatctac atctgggccc ctctggccgg cacatgcgga     660
gtgctgctgc tgagcctcgt gatcaccctg tactgcaagc ggggcagaaa gaagctgctg     720
tacatcttca gcagcccctt catgcggccc gtgcagacca cacaggaaga ggacggctgc     780
tcctgccggt ccccgagga agaagaaggc ggctgcgagc tgagagtgaa gttctctaga     840
agcgccgacg cccctgccta ccagcaggga cagaaccagc tgtacaacga gctgaacctg     900
ggcagacggg aagagtacga cgtgctggac aagcggagag ccgggacccc tgagatggga     960
ggcaagagaa agaaccccca ggaaggcctg tataacgaac tgcagaaaga caagatggcc    1020
gaggcctaca gcgagatcgg aatgaagggc gagcggagaa gaggcaaggg ccacgatgga    1080
ctgtatcagg gcctgagcac cgccaccaag gacacctatg acgccctgca catgcaggcc    1140
ctgcccccca ga                                                        1152
```

-continued

```
<210> SEQ ID NO 11
<211> LENGTH: 384
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Asp Trp Ile Trp Arg Ile Leu Phe Leu Val Gly Ala Ala Thr Gly
1               5                   10                  15

Ala His Ser Asn Gly Ala Ile Lys Val Gly Ala Trp Gly Gly Asn Gly
                20                  25                  30

Gly Ser Ala Phe Asp Met Gly Pro Ala Tyr Arg Ile Ile Ser Val Lys
            35                  40                  45

Ile Phe Ser Gly Asp Val Val Asp Gly Val Asp Val Thr Phe Thr Tyr
        50                  55                  60

Tyr Gly Lys Thr Glu Thr Arg His Tyr Gly Gly Ser Gly Gly Thr Pro
65                  70                  75                  80

His Glu Ile Val Leu Gln Glu Gly Glu Tyr Leu Val Gly Met Ala Gly
                85                  90                  95

Glu Val Ala Asn Tyr Thr Gly Ala Val Val Leu Gly Lys Leu Gly Phe
                100                 105                 110

Ser Thr Asn Lys Lys Ala Tyr Gly Pro Phe Gly Asn Thr Gly Gly Thr
                115                 120                 125

Pro Phe Ser Leu Pro Ile Ala Ala Gly Ile Ser Gly Phe Phe Gly Arg
        130                 135                 140

Gly Gly Lys Phe Leu Asp Ala Ile Gly Val Tyr Leu Glu Pro Gly Gly
145                 150                 155                 160

Gly Gly Ser Thr Thr Thr Pro Ala Pro Arg Pro Pro Thr Pro Ala Pro
                165                 170                 175

Thr Ile Ala Ser Gln Pro Leu Ser Leu Arg Pro Glu Ala Cys Arg Pro
                180                 185                 190

Ala Ala Gly Gly Ala Val His Thr Arg Gly Leu Asp Phe Ala Cys Asp
                195                 200                 205

Ile Tyr Ile Trp Ala Pro Leu Ala Gly Thr Cys Gly Val Leu Leu Leu
        210                 215                 220

Ser Leu Val Ile Thr Leu Tyr Cys Lys Arg Gly Arg Lys Lys Leu Leu
225                 230                 235                 240

Tyr Ile Phe Lys Gln Pro Phe Met Arg Pro Val Gln Thr Thr Gln Glu
                245                 250                 255

Glu Asp Gly Cys Ser Cys Arg Phe Pro Glu Glu Glu Glu Gly Gly Cys
                260                 265                 270

Glu Leu Arg Val Lys Phe Ser Arg Ser Ala Asp Ala Pro Ala Tyr Gln
                275                 280                 285

Gln Gly Gln Asn Gln Leu Tyr Asn Glu Leu Asn Leu Gly Arg Arg Glu
        290                 295                 300

Glu Tyr Asp Val Leu Asp Lys Arg Arg Gly Arg Asp Pro Glu Met Gly
305                 310                 315                 320

Gly Lys Arg Lys Asn Pro Gln Glu Gly Leu Tyr Asn Glu Leu Gln Lys
                325                 330                 335

Asp Lys Met Ala Glu Ala Tyr Ser Glu Ile Gly Met Lys Gly Glu Arg
                340                 345                 350

Arg Arg Gly Lys Gly His Asp Gly Leu Tyr Gln Gly Leu Ser Thr Ala
        355                 360                 365
```

-continued

```
Thr Lys Asp Thr Tyr Asp Ala Leu His Met Gln Ala Leu Pro Pro Arg
    370             375             380

<210> SEQ ID NO 12
<211> LENGTH: 1273
<212> TYPE: PRT
<213> ORGANISM: Severe acute respiratory syndrome coronavirus 2

<400> SEQUENCE: 12

Met Phe Val Phe Leu Val Leu Leu Pro Leu Val Ser Ser Gln Cys Val
1               5               10              15

Asn Leu Thr Thr Arg Thr Gln Leu Pro Pro Ala Tyr Thr Asn Ser Phe
            20              25              30

Thr Arg Gly Val Tyr Tyr Pro Asp Lys Val Phe Arg Ser Ser Val Leu
        35              40              45

His Ser Thr Gln Asp Leu Phe Leu Pro Phe Phe Ser Asn Val Thr Trp
    50              55              60

Phe His Ala Ile His Val Ser Gly Thr Asn Gly Thr Lys Arg Phe Asp
65              70              75              80

Asn Pro Val Leu Pro Phe Asn Asp Gly Val Tyr Phe Ala Ser Thr Glu
                85              90              95

Lys Ser Asn Ile Ile Arg Gly Trp Ile Phe Gly Thr Thr Leu Asp Ser
            100             105             110

Lys Thr Gln Ser Leu Leu Ile Val Asn Asn Ala Thr Asn Val Val Ile
            115             120             125

Lys Val Cys Glu Phe Gln Phe Cys Asn Asp Pro Phe Leu Gly Val Tyr
        130             135             140

Tyr His Lys Asn Asn Lys Ser Trp Met Glu Ser Glu Phe Arg Val Tyr
145             150             155             160

Ser Ser Ala Asn Asn Cys Thr Phe Glu Tyr Val Ser Gln Pro Phe Leu
            165             170             175

Met Asp Leu Glu Gly Lys Gln Gly Asn Phe Lys Asn Leu Arg Glu Phe
            180             185             190

Val Phe Lys Asn Ile Asp Gly Tyr Phe Lys Ile Tyr Ser Lys His Thr
            195             200             205

Pro Ile Asn Leu Val Arg Asp Leu Pro Gln Gly Phe Ser Ala Leu Glu
    210             215             220

Pro Leu Val Asp Leu Pro Ile Gly Ile Asn Ile Thr Arg Phe Gln Thr
225             230             235             240

Leu Leu Ala Leu His Arg Ser Tyr Leu Thr Pro Gly Asp Ser Ser Ser
            245             250             255

Gly Trp Thr Ala Gly Ala Ala Ala Tyr Tyr Val Gly Tyr Leu Gln Pro
            260             265             270

Arg Thr Phe Leu Leu Lys Tyr Asn Glu Asn Gly Thr Ile Thr Asp Ala
        275             280             285

Val Asp Cys Ala Leu Asp Pro Leu Ser Glu Thr Lys Cys Thr Leu Lys
    290             295             300

Ser Phe Thr Val Glu Lys Gly Ile Tyr Gln Thr Ser Asn Phe Arg Val
305             310             315             320

Gln Pro Thr Glu Ser Ile Val Arg Phe Pro Asn Ile Thr Asn Leu Cys
            325             330             335

Pro Phe Gly Glu Val Phe Asn Ala Thr Arg Phe Ala Ser Val Tyr Ala
            340             345             350

Trp Asn Arg Lys Arg Ile Ser Asn Cys Val Ala Asp Tyr Ser Val Leu
            355             360             365
```

-continued

```
Tyr Asn Ser Ala Ser Phe Ser Thr Phe Lys Cys Tyr Gly Val Ser Pro
    370             375             380

Thr Lys Leu Asn Asp Leu Cys Phe Thr Asn Val Tyr Ala Asp Ser Phe
385             390             395             400

Val Ile Arg Gly Asp Glu Val Arg Gln Ile Ala Pro Gly Gln Thr Gly
            405             410             415

Lys Ile Ala Asp Tyr Asn Tyr Lys Leu Pro Asp Asp Phe Thr Gly Cys
            420             425             430

Val Ile Ala Trp Asn Ser Asn Asn Leu Asp Ser Lys Val Gly Gly Asn
            435             440             445

Tyr Asn Tyr Leu Tyr Arg Leu Phe Arg Lys Ser Asn Leu Lys Pro Phe
    450             455             460

Glu Arg Asp Ile Ser Thr Glu Ile Tyr Gln Ala Gly Ser Thr Pro Cys
465             470             475             480

Asn Gly Val Glu Gly Phe Asn Cys Tyr Phe Pro Leu Gln Ser Tyr Gly
            485             490             495

Phe Gln Pro Thr Asn Gly Val Gly Tyr Gln Pro Tyr Arg Val Val Val
            500             505             510

Leu Ser Phe Glu Leu Leu His Ala Pro Ala Thr Val Cys Gly Pro Lys
    515             520             525

Lys Ser Thr Asn Leu Val Lys Asn Lys Cys Val Asn Phe Asn Phe Asn
    530             535             540

Gly Leu Thr Gly Thr Gly Val Leu Thr Glu Ser Asn Lys Lys Phe Leu
545             550             555             560

Pro Phe Gln Gln Phe Gly Arg Asp Ile Ala Asp Thr Thr Asp Ala Val
            565             570             575

Arg Asp Pro Gln Thr Leu Glu Ile Leu Asp Ile Thr Pro Cys Ser Phe
            580             585             590

Gly Gly Val Ser Val Ile Thr Pro Gly Thr Asn Thr Ser Asn Gln Val
            595             600             605

Ala Val Leu Tyr Gln Asp Val Asn Cys Thr Glu Val Pro Val Ala Ile
    610             615             620

His Ala Asp Gln Leu Thr Pro Thr Trp Arg Val Tyr Ser Thr Gly Ser
625             630             635             640

Asn Val Phe Gln Thr Arg Ala Gly Cys Leu Ile Gly Ala Glu His Val
            645             650             655

Asn Asn Ser Tyr Glu Cys Asp Ile Pro Ile Gly Ala Gly Ile Cys Ala
            660             665             670

Ser Tyr Gln Thr Gln Thr Asn Ser Pro Arg Arg Ala Arg Ser Val Ala
    675             680             685

Ser Gln Ser Ile Ile Ala Tyr Thr Met Ser Leu Gly Ala Glu Asn Ser
    690             695             700

Val Ala Tyr Ser Asn Asn Ser Ile Ala Ile Pro Thr Asn Phe Thr Ile
705             710             715             720

Ser Val Thr Thr Glu Ile Leu Pro Val Ser Met Thr Lys Thr Ser Val
            725             730             735

Asp Cys Thr Met Tyr Ile Cys Gly Asp Ser Thr Glu Cys Ser Asn Leu
            740             745             750

Leu Leu Gln Tyr Gly Ser Phe Cys Thr Gln Leu Asn Arg Ala Leu Thr
    755             760             765

Gly Ile Ala Val Glu Gln Asp Lys Asn Thr Gln Glu Val Phe Ala Gln
    770             775             780
```

```
Val Lys Gln Ile Tyr Lys Thr Pro Pro Ile Lys Asp Phe Gly Gly Phe
785             790             795             800

Asn Phe Ser Gln Ile Leu Pro Asp Pro Ser Lys Pro Ser Lys Arg Ser
            805             810             815

Phe Ile Glu Asp Leu Leu Phe Asn Lys Val Thr Leu Ala Asp Ala Gly
        820             825             830

Phe Ile Lys Gln Tyr Gly Asp Cys Leu Gly Asp Ile Ala Ala Arg Asp
        835             840             845

Leu Ile Cys Ala Gln Lys Phe Asn Gly Leu Thr Val Leu Pro Pro Leu
    850             855             860

Leu Thr Asp Glu Met Ile Ala Gln Tyr Thr Ser Ala Leu Leu Ala Gly
865             870             875             880

Thr Ile Thr Ser Gly Trp Thr Phe Gly Ala Gly Ala Ala Leu Gln Ile
            885             890             895

Pro Phe Ala Met Gln Met Ala Tyr Arg Phe Asn Gly Ile Gly Val Thr
        900             905             910

Gln Asn Val Leu Tyr Glu Asn Gln Lys Leu Ile Ala Asn Gln Phe Asn
        915             920             925

Ser Ala Ile Gly Lys Ile Gln Asp Ser Leu Ser Ser Thr Ala Ser Ala
    930             935             940

Leu Gly Lys Leu Gln Asp Val Val Asn Gln Asn Ala Gln Ala Leu Asn
945             950             955             960

Thr Leu Val Lys Gln Leu Ser Ser Asn Phe Gly Ala Ile Ser Ser Val
            965             970             975

Leu Asn Asp Ile Leu Ser Arg Leu Asp Lys Val Glu Ala Glu Val Gln
        980             985             990

Ile Asp Arg Leu Ile Thr Gly Arg  Leu Gln Ser Leu Gln  Thr Tyr Val
        995             1000            1005

Thr Gln  Gln Leu Ile Arg Ala  Ala Glu Ile Arg Ala  Ser Ala Asn
    1010            1015            1020

Leu Ala  Ala Thr Lys Met Ser  Glu Cys Val Leu Gly  Gln Ser Lys
    1025            1030            1035

Arg Val  Asp Phe Cys Gly Lys  Gly Tyr His Leu Met  Ser Phe Pro
    1040            1045            1050

Gln Ser  Ala Pro His Gly Val  Val Phe Leu His Val  Thr Tyr Val
    1055            1060            1065

Pro Ala  Gln Glu Lys Asn Phe  Thr Thr Ala Pro Ala  Ile Cys His
    1070            1075            1080

Asp Gly  Lys Ala His Phe Pro  Arg Glu Gly Val Phe  Val Ser Asn
    1085            1090            1095

Gly Thr  His Trp Phe Val Thr  Gln Arg Asn Phe Tyr  Glu Pro Gln
    1100            1105            1110

Ile Ile  Thr Thr Asp Asn Thr  Phe Val Ser Gly Asn  Cys Asp Val
    1115            1120            1125

Val Ile  Gly Ile Val Asn Asn  Thr Val Tyr Asp Pro  Leu Gln Pro
    1130            1135            1140

Glu Leu  Asp Ser Phe Lys Glu  Glu Leu Asp Lys Tyr  Phe Lys Asn
    1145            1150            1155

His Thr  Ser Pro Asp Val Asp  Leu Gly Asp Ile Ser  Gly Ile Asn
    1160            1165            1170

Ala Ser  Val Val Asn Ile Gln  Lys Glu Ile Asp Arg  Leu Asn Glu
    1175            1180            1185

Val Ala  Lys Asn Leu Asn Glu  Ser Leu Ile Asp Leu  Gln Glu Leu
```

-continued

```
        1190                1195                1200

Gly Lys  Tyr Glu Gln Tyr Ile  Lys Trp Pro Trp Tyr  Ile Trp Leu
        1205                1210                1215

Gly Phe  Ile Ala Gly Leu Ile  Ala Ile Val Met Val  Thr Ile Met
        1220                1225                1230

Leu Cys  Cys Met Thr Ser Cys  Cys Ser Cys Leu Lys  Gly Cys Cys
        1235                1240                1245

Ser Cys  Gly Ser Cys Cys Lys  Phe Asp Glu Asp Asp  Ser Glu Pro
        1250                1255                1260

Val Leu  Lys Gly Val Lys Leu  His Tyr Thr
        1265                1270
```

```
<210> SEQ ID NO 13
<211> LENGTH: 29903
<212> TYPE: DNA
<213> ORGANISM: Severe acute respiratory syndrome coronavirus 2

<400> SEQUENCE: 13
attaaaggtt tataccttcc caggtaacaa accaaccaac tttcgatctc ttgtagatct      60
gttctctaaa cgaactttaa aatctgtgtg gctgtcactc ggctgcatgc ttagtgcact     120
cacgcagtat aattaataac taattactgt cgttgacagg acacgagtaa ctcgtctatc     180
ttctgcaggc tgcttacggt ttcgtccgtg ttgcagccga tcatcagcac atctaggttt     240
cgtccgggtg tgaccgaaag gtaagatgga gagccttgtc cctggtttca acgagaaaac     300
acacgtccaa ctcagtttgc ctgttttaca ggttcgcgac gtgctcgtac gtggctttgg     360
agactccgtg gaggaggtct tatcagaggc acgtcaacat cttaaagatg gcacttgtgg     420
cttagtagaa gttgaaaaag gcgttttgcc tcaacttgaa cagccctatg tgttcatcaa     480
acgttcggat gctcgaactg cacctcatgg tcatgttatg gttgagctgg tagcagaact     540
cgaaggcatt cagtacggtc gtagtggtga cacttggt gtccttgtcc ctcatgtggg     600
cgaaatacca gtggcttacc gcaaggttct tcttcgtaag aacggtaata aaggagctgg     660
tggccatagt tacggcgccg atctaaagtc atttgactta ggcgacgagc ttggcactga     720
tccttatgaa gattttcaag aaaactggaa cactaaacat agcagtggtg ttacccgtga     780
actcatgcgt gagcttaacg gaggggcata cactcgctat gtcgataaca acttctgtgg     840
ccctgatggc taccttcttg agtgcattaa agaccttcta gcacgtgctg gtaaagcttc     900
atgcactttg tccgaacaac tggactttat tgacactaag aggggtgtat actgctgccg     960
tgaacatgag catgaaattg cttggtacac ggaacgttct gaaaagagct atgaattgca    1020
gacacctttt gaaattaaat tggcaaagaa atttgacacc ttcaatgggg aatgtccaaa    1080
ttttgtattt cccttaaatt ccataatcaa gactattcaa ccaagggttg aaaagaaaaa    1140
gcttgatggc tttatgggta gaattcgatc tgtctatcca gttgcgtcac caaatgaatg    1200
caaccaaatg tgcctttcaa ctctcatgaa gtgtgatcat gttggtgaaa cttcatggca    1260
gacgggcgat tttgttaaag ccacttgcga ttttgtggc actgagaatt tgactaaaga    1320
aggtgccact acttgtggtt acttacccca aaatgctgtt gttaaattt attgtccagc    1380 atgtcacaat tcagaagtag gacctgagca tagtcttgcc gaataccata tgaatctgg    1440 cttgaaaacc attcttcgta agggtggtcg cactattgcc tttggaggct gtgtgttctc    1500
ttatgttggt tgccataaca gtgtgccta ttgggttcca cgtgctagcg ctaacatagg    1560
ttgtaaccat acaggtgttg ttggagaagg ttccgaaggt cttaatgaca accttcttga    1620
```

-continued

```
aatactccaa aaagagaaag tcaacatcaa tattgttggt gactttaaac ttaatgaaga    1680
gatcgccatt attttggcat cttttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagttta gtggttattt    3360 aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
tatttttggt gctgacccta tacattcttt aagagtttgt gtagatactg ttcgcacaaa   3780
tgtctactta gctgtctttg ataaaaatct ctatgacaaa cttgtttcaa gcttttttgga  3840 aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
caaagcttgt gttgaagaag ttacaacaac tctggaagaa actaagttcc tcacagaaaa   4020
```

```
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga gtttaatcc   5340 acctgctcta caagatgctt attacagagc aagggctggt gaagctgcta acttttgtgc   5400
acttatctta gcctactgta ataagacagt aggtgagtta ggtgatgtta gagaaacaat   5460
gagttacttg tttcaacatg ccaatttaga ttcttgcaaa agagtcttga cgtggtgtg   5520 taaaacttgt ggacaacagc agacaacccct taagggtgta gaagctgtta tgtacatggg   5580
cacactttct tatgaacaat ttaagaaagg tgttcagata ccttgtacgt gtggtaaaca   5640
agctacaaaa tatctagtac aacaggagtc accttttgtt atgatgtcag caccacctgc   5700
tcagtatgaa cttaagcatg gtacatttac ttgtgctagt gagtacactg gtaattacca   5760
gtgtggtcac tataaacata taacttctaa agaaactttg tattgcatag acggtgcttt   5820
acttacaaag tcctcagaat acaaaggtcc tattacggat gttttctaca agagaaacag   5880
ttacacaaca accataaaac cagttactta taaattggat ggtgttgttt gtacagaaat   5940
tgaccctaag ttggacaatt attataagaa agacaattct tatttcacag agcaaccaat   6000
tgatcttgta ccaaaccaac atatccaaa cgcaagcttc gataatttta gtttgtatg   6060 tgataatatc aaatttgctg atgatttaaa ccagttaact ggttataaga aacctgcttc   6120
aagagagctt aaagttacat ttttccctga cttaaatggt gatgtggtgg ctattgatta   6180
taaacactac acaccctctt ttaagaaagg agctaaattg ttacataaac ctattgtttg   6240
gcatgttaac aatgcaacta ataaagccac gtataaacca aatacctggt gtatacgttg   6300
tctttggagc acaaaaccag ttgaaacatc aaattcgttt gatgtactga agtcagagga   6360
```

```
cgcgcaggga atggataatc ttgcctgcga agatctaaaa ccagtctctg aagaagtagt      6420
ggaaaatcct accatacaga aagacgttct tgagtgtaat gtgaaaacta ccgaagttgt      6480
aggagacatt atacttaaac cagcaaataa tagtttaaaa attacagaag aggttggcca      6540
cacagatcta atggctgctt atgtagacaa ttctagtctt actattaaga aacctaatga      6600
attatctaga gtattaggtt tgaaaaccct tgctactcat ggtttagctg ctgttaatag      6660
tgtcccttgg gatactatag ctaattatgc taagcctttt cttaacaaag ttgttagtac      6720
aactactaac atagttacac ggtgtttaaa ccgtgtttgt actaattata tgccttattt      6780
ctttacttta ttgctacaat gtgtgacttt tactagaagt acaaattcta gaattaaagc      6840
atctatgccg actactatag caaagaatac tgttaagagt gtcggtaaat tttgtctaga      6900
ggcttcattt aattatttga agtcacctaa ttttttctaaa ctgataaata ttataatttg      6960
gtttttacta ttaagtgttt gcctaggttc tttaatctac tcaaccgctg ctttaggtgt      7020
tttaatgtct aatttaggca tgccttctta ctgtactggt tacagagaag gctatttgaa      7080
ctctactaat gtcactattg caacctactg tactggttct ataccttgta gtgtttgtct      7140 tagtggtttta gattctttag acacctatcc ttctttagaa actatacaaa ttaccatttc      7200
atcttttaaa tgggatttaa ctgctttttgg cttagttgca gagtggtttt tggcatatat      7260
tcttttcact aggttttttct atgtacttgg attggctgca atcatgcaat tgttttttcag      7320 ctattttgca gtacatttta ttagtaattc ttggcttatg tggttaataa ttaatcttgt      7380
acaaatggcc ccgatttcag ctatggttag aatgtacatc ttctttgcat cattttatta      7440
tgtatggaaa agttatgtgc atgttgtaga cggttgtaat tcatcaactt gtatgatgtg      7500
ttacaaacgt aatagagcaa caagagtcga atgtacaact attgttaatg gtgttagaag      7560
gtccttttat gtctatgcta atggaggtaa aggcttttgc aaactacaca attggaattg      7620
tgttaattgt gatacattct gtgctggtag tacatttatt agtgatgaag ttgcgagaga      7680
cttgtcacta cagtttaaaa gaccaataaa tcctactgac cagtcttctt acatcgttga      7740
tagtgttaca gtgaagaatg gttccatcca tctttacttt gataaagctg gtcaaaagac      7800
ttatgaaaga cattctctct ctcattttgt taacttagac aacctgagag ctaataacac      7860
taaaggttca ttgcctatta atgttatagt ttttgatggt aaatcaaaat gtgaagaatc      7920
atctgcaaaa tcagcgtctg tttactacag tcagcttatg tgtcaaccta tactgttact      7980
agatcaggca ttagtgtctg atgttggtga tagtgcggaa gttgcagtta aaatgtttga      8040
tgcttacgtt aatacgtttt catcaacttt taacgtacca atggaaaaac tcaaaacact      8100
agttgcaact gcagaagctg aacttgcaaa gaatgtgtcc ttagacaatg tcttatctac      8160
ttttatttca gcagctcggc aagggtttgt tgattcagat gtagaaacta agatgttgt      8220 tgaatgtctt aaattgtcac atcaatctga catagaagtt actggcgata gttgtaataa      8280
ctatatgctc acctataaca agttgaaaa catgacaccc cgtgaccttg gtgcttgtat      8340
tgactgtagt gcgcgtcata ttaatgcgca ggtagcaaaa agtcacaaca ttgctttgat      8400
atggaacgtt aaagatttca tgtcattgtc tgaacaacta cgaaaacaaa tacgtagtgc      8460
tgctaaaaag aataacttac ctttttaagtt gacatgtgca actactagac aagttgttaa      8520
tgttgtaaca acaaagatag cacttaaggg tggtaaaatt gttaataatt ggttgaagca      8580
gttaattaaa gttacacttg tgttcctttt tgttgctgct attttctatt taataacacc      8640
tgttcatgtc atgtctaaac atactgactt ttcaagtgaa atcataggat acaaggctat      8700
tgatggtggt gtcactcgtg acatagcatc tacagatact tgttttgcta acaaacatgc      8760
```

```
tgattttgac acatggttta gccagcgtgg tggtagttat actaatgaca aagcttgccc   8820
attgattgct gcagtcataa caagagaagt gggtttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttatttt acttgtactt   9600 gacattttat cttactaatg atgtttctttt tttagcacat attcagtgga tggttatgtt   9660 cacacctttta gtacctttct ggataacaat tgcttatatc atttgtatttt ccacaaagca   9720 tttctattgg ttctttagta attacctaaa gagacgtgta gtctttaatg gtgtttcctt   9780
tagtactttt gaagaagctg cgctgtgcac cttttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc   10020
accacaaacc tctatcacct cagctgtttt gcagagtggt tttagaaaaa tggcattccc   10080
atctggtaaa gttgagggtt gtatggtaca agtaacttgt ggtacaacta cacttaacgg   10140
tctttggctt gatgacgtag tttactgtcc aagacatgtg atctgcacct ctgaagacat   10200
gcttaaccct aattatgaag atttactcat tcgtaagtct aatcataatt tcttggtaca   10260
ggctggtaat gttcaactca gggttattgg acattctatg caaaattgtg tacttaagct   10320
taaggttgat acagccaatc ctaagacacc taagtataag tttgttcgca ttcaaccagg   10380
acagactttt tcagtgttag cttgttacaa tggttcacca tctggtgttt accaatgtgc   10440
tatgaggccc aatttcacta ttaagggttc attccttaat ggttcatgtg gtagtgttgg   10500 tttttaacata gattatgact gtgtctcttt ttgttacatg caccatatgg aattaccaac   10560
tggagttcat gctggcacag acttagaagg taacttttat ggacctttttg ttgacaggca   10620 aacagcacaa gcagctggta cggacacaac tattacagtt aatgtttttag cttggttgta   10680 cgctgctgtt ataaatggag acaggtggtt tctcaatcga tttaccacaa ctcttaatga   10740
ctttaacctt gtggctatga agtacaatta tgaacctcta acacaagacc atgttgacat   10800
actaggacct ctttctgctc aaactggaat tgccgtttta gatatgtgtg cttcattaaa   10860
agaattactg caaaatggta tgaatggacg taccatattg ggtagtgctt tattagaaga   10920
tgaatttaca ccttttgatg ttgttagaca atgctcaggt gttactttcc aaagtgcagt   10980
gaaaagaaca atcaagggta cacaccactg gttgttactc acaattttga cttcactttt   11040
agttttagtc cagagtactc aatggtcttt gttcttttttt ttgtatgaaa atgccttttt   11100
```

-continued

```
acctttttgct atgggtatta ttgctatgtc tgctttttgca atgatgtttg tcaaacataa   11160
gcatgcattt ctctgtttgt ttttgttacc ttctcttgcc actgtagctt attttaatat   11220
ggtctatatg cctgctagtt gggtgatgcg tattatgaca tggttggata tggttgatac   11280
tagtttgtct ggttttaagc taaaagactg tgttatgtat gcatcagctg tagtgttact   11340
aatccttatg acagcaagaa ctgtgtatga tgatggtgct aggagagtgt ggacacttat   11400
gaatgtcttg acactcgttt ataaagttta ttatggtaat gctttagatc aagccatttc   11460
catgtgggct cttataatct ctgttacttc taactactca ggtgtagtta caactgtcat   11520 gttttttggcc agaggtattg ttttttatgtg tgttgagtat tgccctattt tcttcataac   11580
tggtaataca cttcagtgta taatgctagt ttattgtttc ttaggctatt tttgtacttg   11640
ttactttggc ctcttttgtt tactcaaccg ctactttaga ctgactcttg gtgtttatga   11700
ttacttagtt tctacacagg agtttagata tatgaattca cagggactac tcccacccaa   11760
gaatagcata gatgccttca aactcaacat taaattgttg ggtgttggtg gcaaaccttg   11820
tatcaaagta gccactgtac agtctaaaat gtcagatgta aagtgcacat cagtagtctt   11880
actctcagtt ttgcaacaac tcagagtaga atcatcatct aaattgtggg ctcaatgtgt   11940
ccagttacac aatgacattc tcttagctaa agatactact gaagcctttg aaaaaatggt   12000
ttcactactt tctgttttgc tttccatgca gggtgctgta gacataaaca agctttgtga   12060
agaaatgctg gacaacaggg caaccttaca agctatagcc tcagagttta gttcccttcc   12120
atcatatgca gcttttgcta ctgctcaaga agcttatgag caggctgttg ctaatggtga   12180
ttctgaagtt gttcttaaaa agttgaagaa gtctttgaat gtggctaaat ctgaatttga   12240
ccgtgatgca gccatgcaac gtaagttgga aaagatggct gatcaagcta tgacccaaat   12300
gtataaacag gctagatctg aggacaagag ggcaaaagtt actagtgcta tgcagacaat   12360
gcttttcact atgcttagaa agttggataa tgatgcactc aacaacatta tcaacaatgc   12420
aagagatggt tgtgttccct tgaacataat acctcttaca acagcagcca aactaatggt   12480
tgtcatacca gactataaca catataaaaa tacgtgtgat ggtacaacat ttacttatgc   12540
atcagcattg tgggaaatcc aacaggttgt agatgcagat agtaaaattg ttcaacttag   12600
tgaaattagt atggacaatt cacctaattt agcatggcct cttattgtaa cagctttaag   12660
ggccaattct gctgtcaaat tacagaataa tgagcttagt cctgttgcac tacgacagat   12720
gtcttgtgct gccggtacta cacaaactgc ttgcactgat gacaatgcgt tagcttacta   12780
caacacaaca aagggaggta ggtttgtact tgcactgtta tccgatttac aggatttgaa   12840
atgggctaga ttccctaaga gtgatggaac tggtactatc tatacagaac tggaaccacc   12900
ttgtaggttt gttacagaca cacctaaagg tcctaaagtg aagtatttat actttattaa   12960
aggattaaac aacctaaata gaggtatggt acttggtagt ttagctgcca cagtacgtct   13020
acaagctggt aatgcaacag aagtgcctgc caattcaact gtattatctt tctgtgcttt   13080
tgctgtagat gctgctaaag cttacaaaga ttatctagct agtgggggac aaccaatcac   13140
taattgtgtt aagatgttgt gtacacacac tggtactggt caggcaataa cagttacacc   13200
ggaagccaat atggatcaag aatcctttgg tggtgcatcg tgttgtctgt actgccgttg   13260
ccacatagat catccaaatc ctaaaggatt ttgtgactta aaaggtaagt atgtacaaat   13320
acctacaact tgtgctaatg accctgtggg ttttacactt aaaaacacag tctgtaccgt   13380
ctgcggtatg tggaaaggtt atggctgtag ttgtgatcaa ctccgcgaac ccatgcttca   13440
gtcagctgat gcacaatcgt ttttaaacgg gtttgcggtg taagtgcagc ccgtcttaca   13500
```

-continued

```
ccgtgcggca caggcactag tactgatgtc gtatacaggg cttttgacat ctacaatgat   13560
aaagtagctg gttttgctaa attcctaaaa actaattgtt gtcgcttcca agaaaaggac   13620
gaagatgaca atttaattga ttcttacttt gtagttaaga gacacacttt ctctaactac   13680
caacatgaag aaacaattta taatttactt aaggattgtc cagctgttgc taaacatgac   13740
ttctttaagt ttagaataga cggtgacatg gtaccacata tatcacgtca acgtcttact   13800
aaatacacaa tggcagacct cgtctatgct ttaaggcatt ttgatgaagg taattgtgac   13860
acattaaaag aaatacttgt cacatacaat tgttgtgatg atgattattt caataaaaag   13920
gactggtatg attttgtaga aaacccagat atattacgcg tatacgccaa cttaggtgaa   13980
cgtgtacgcc aagctttgtt aaaaacagta caattctgtg atgccatgcg aaatgctggt   14040
attgttggtg tactgacatt agataatcaa gatctcaatg gtaactggta tgatttcggt   14100
gatttcatac aaaccacgcc aggtagtgga gttcctgttg tagattctta ttattcattg   14160
ttaatgccta tattaacctt gaccagggct ttaactgcag agtcacatgt tgacactgac   14220
ttaacaaagc cttacattaa gtgggatttg ttaaaatatg acttcacgga agagaggtta   14280
aaactctttg accgttattt taaatattgg gatcagacat accacccaaa ttgtgttaac   14340
tgtttggatg acagatgcat tctgcattgt gcaaacttta atgttttatt ctctacagtg   14400
ttcccaccta caagttttgg accactagtg agaaaaatat ttgttgatgg tgttccattt   14460
gtagtttcaa ctggatacca cttcagagag ctaggtgttg tacataatca ggatgtaaac   14520
ttacatagct ctagacttag tttttaaggaa ttacttgtgt atgctgctga ccctgctatg   14580
cacgctgctt ctggtaatct attactagat aaacgcacta cgtgcttttc agtagctgca   14640
cttactaaca atgttgcttt tcaaactgtc aaacccggta attttaacaa agacttctat   14700
gactttgctg tgtctaaggg tttctttaag gaaggaagtt ctgttgaatt aaaaacacttc   14760 ttctttgctc aggatggtaa tgctgctatc agcgattatg actactatcg ttataatcta   14820
ccaacaatgt gtgatatcag acaactacta tttgtagttg aagttgttga taagtacttt   14880
gattgttacg atggtggctg tattaatgct aaccaagtca tcgtcaacaa cctagacaaa   14940
tcagctggtt ttccatttaa taaatggggt aaggctagac tttattatga ttcaatgagt   15000
tatgaggatc aagatgcact tttcgcatat acaaaacgta atgtcatccc tactataact   15060
caaatgaatc ttaagtatgc cattagtgca aagaatagag ctcgcaccgt agctggtgtc   15120
tctatctgta gtactatgac caatagacag tttcatcaaa aattattgaa atcaatagcc   15180
gccactagag gagctactgt agtaattgga acaagcaaat ctatggtgg ttggcacaac   15240 atgttaaaaa ctgtttatag tgatgtagaa aaccctcacc ttatgggttg ggattatcct   15300
aaatgtgata gagccatgcc taacatgctt agaattatgg cctcacttgt tcttgctcgc   15360
aaacatacaa cgtgttgtag cttgtcacac cgtttctata gattagctaa tgagtgtgct   15420
caagtattga gtgaaatggt catgtgtggc ggttcactat atgttaaacc aggtggaacc   15480
tcatcaggag atgccacaac tgcttatgct aatagtgttt ttaacatttg tcaagctgtc   15540
acggccaatg ttaatgcact tttatctact gatggtaaca aaattgccga taagtatgtc   15600
cgcaatttac aacacagact ttatgagtgt ctctataaga atagagatgt tgacacagac   15660
tttgtgaatg agttttacgc atatttgcgt aaacatttct caatgatgat actctctgac   15720
gatgctgttg tgtgtttcaa tagcacttat gcatctcaag gtctagtggc tagcataaag   15780
aactttaagt cagttctttta ttatcaaaac aatgttttta tgtctgaagc aaaatgttgg   15840
```

-continued

```
actgagactg accttactaa aggacctcat gaattttgct ctcaacatac aatgctagtt   15900
aaacagggtg atgattatgt gtaccttcct tacccagatc catcaagaat cctaggggcc   15960
ggctgttttg tagatgatat cgtaaaaaca gatggtacac ttatgattga acggttcgtg   16020
tctttagcta tagatgctta cccacttact aaacatccta atcaggagta tgctgatgtc   16080
tttcatttgt acttacaata cataagaaag ctacatgatg agttaacagg acacatgtta   16140
gacatgtatt ctgttatgct tactaatgat aacacttcaa ggtattggga acctgagttt   16200
tatgaggcta tgtacacacc gcatacagtc ttacaggctg ttggggcttg tgttctttgc   16260
aattcacaga cttcattaag atgtggtgct tgcatacgta gaccattctt atgttgtaaa   16320
tgctgttacg accatgtcat atcaacatca cataaattag tcttgtctgt taatccgtat   16380
gtttgcaatg ctccaggttg tgatgtcaca gatgtgactc aactttactt aggaggtatg   16440
agctattatt gtaaatcaca taaaccaccc attagttttc cattgtgtgc taatggacaa   16500 gttttttggtt tatataaaaa tacatgtgtt ggtagcgata atgttactga ctttaatgca   16560
attgcaacat gtgactggac aaatgctggt gattacattt tagctaacac ctgtactgaa   16620
agactcaagc tttttgcagc agaaacgctc aaagctactg aggagacatt taaactgtct   16680
tatggtattg ctactgtacg tgaagtgctg tctgacagag aattacatct ttcatgggaa   16740
gttggtaaac ctagaccacc acttaaccga aattatgtct ttactggtta tcgtgtaact   16800
aaaaacagta aagtacaaat aggagagtac acctttgaaa aaggtgacta tggtgatgct   16860
gttgtttacc gaggtacaac aacttacaaa ttaaatgttg gtgattattt tgtgctgaca   16920
tcacatacag taatgccatt aagtgcacct acactagtgc cacaagagca ctatgttaga   16980
attactggct tatacccaac actcaatatc tcagatgagt tttctagcaa tgttgcaaat   17040
tatcaaaagg ttggtatgca aaagtattct acactccagg gaccacctgg tactggtaag   17100
agtcattttg ctattggcct agctctctac taccccttctg ctcgcatagt gtatacagct   17160
tgctctcatg ccgctgttga tgcactatgt gagaaaggcat taaaatattt gcctatagat   17220
aaatgtagta gaattatacc tgcacgtgct cgtgtagagt gtttttgataa attcaaagtg   17280 aattcaacat tagaacagta tgtcttttgt actgtaaatg cattgcctga gacgacagca   17340
gatatagttg tctttgatga aatttcaatg gccacaaatt atgatttgag tgttgtcaat   17400
gccagattac gtgctaagca ctatgtgtac attggcgacc ctgctcaatt acctgcacca   17460
cgcacattgc taactaaggg cacactagaa ccagaatatt tcaattcagt gtgtagactt   17520
atgaaaacta taggtccaga catgttcctc ggaacttgtc ggcgttgtcc tgctgaaatt   17580
gttgacactg tgagtgcttt ggtttatgat aataagctta aagcacataa agacaaatca   17640
gctcaatgct ttaaaatgtt ttataagggg gttatcacgc atgatgtttc atctgcaatt   17700
aacaggccac aaataggcgt ggtaagagaa ttccttacac gtaaccctgc ttggagaaaa   17760
gctgtcttta tttcacctta taattcacag aatgctgtag cctcaaagat tttgggacta   17820
ccaactcaaa ctgttgattc atcacagggc tcagaatatg actatgtcat attcactcaa   17880
accactgaaa cagctcactc ttgtaatgta aacagattta atgttgctat taccagagca   17940
aaagtaggca tactttgcat aatgtctgat agagaccttt atgacaagtt gcaatttaca   18000
agtcttgaaa ttccacgtag gaatgtggca actttacaag ctgaaaatgt aacaggactc   18060
tttaaagatt gtagtaaggt aatcactggg ttacatccta cacaggcacc tacacacctc   18120
agtgttgaca ctaaattcaa aactgaaggt ttatgtgttg acatacctgg catacctaag   18180
gacatgacct atagaagact catctctatg atgggtttta aaatgaatta tcaagttaat   18240
```

-continued

```
ggttaccata acatgtttat cacccgcgaa gaagctataa gacatgtacg tgcatggatt   18300
ggcttcgatg tcgaggggtg tcatgctact agagaagctg ttggtaccaa tttaccttta   18360
cagctaggtt tttctacagg tgttaaccta gttgctgtac ctacaggtta tgttgataca   18420
cctaataata cagatttttc cagagttagt gctaaaccac cgcctggaga tcaatttaaa   18480
cacctcatac cacttatgta caaaggactt ccttggaatg tagtgcgtat aaagattgta   18540
caaatgttaa gtgacacact taaaaatctc tctgacagag tcgtatttgt cttatgggca   18600
catggctttg agttgacatc tatgaagtat tttgtgaaaa taggacctga gcgcacctgt   18660
tgtctatgtg atagacgtgc cacatgcttt tccactgctt cagacactta tgcctgttgg   18720
catcattcta ttggatttga ttacgtctat aatccgttta tgattgatgt tcaacaatgg   18780
ggttttacag gtaacctaca aagcaaccat gatctgtatt gtcaagtcca tggtaatgca   18840
catgtagcta gttgtgatgc aatcatgact aggtgtctag ctgtccacga gtgctttgtt   18900
aagcgtgttg actggactat tgaatatcct ataattggtg atgaactgaa gattaatgcg   18960
gcttgtagaa aggttcaaca catggttgtt aaagctgcat tattagcaga caaattccca   19020
gttcttcacg acattggtaa ccctaaagct attaagtgtg tacctcaagc tgatgtagaa   19080
tggaagttct atgatgcaca gccttgtagt gacaaagctt ataaaataga agaattattc   19140
tattcttatg ccacacattc tgacaaattc acagatggtg tatgcctatt ttggaattgc   19200
aatgtcgata gatatcctgc taattccatt gtttgtagat ttgacactag agtgctatct   19260
aaccttaact tgcctggttg tgatggtggc agtttgtatg taaataaaca tgcattccac   19320
acaccagctt ttgataaaag tgcttttgtt aatttaaaac aattaccatt tttctattac   19380
tctgacagtc catgtgagtc tcatggaaaa caagtagtgt cagatataga ttatgtacca   19440
ctaaagtctg ctacgtgtat aacacgttgc aatttaggtg gtgctgtctg tagacatcat   19500
gctaatgagt acagattgta tctcgatgct tataacatga tgatctcagc tggctttagc   19560
ttgtgggttt acaaacaatt tgatacttat aacctctgga acacttttac aagacttcag   19620
agtttagaaa atgtggcttt taatgttgta aataagggac actttgatgg acaacagggt   19680
gaagtaccag tttctatcat taataacact gtttacacaa aagttgatgg tgttgatgta   19740
gaattgtttg aaaataaaac aacattacct gttaatgtag catttgagct ttgggctaag   19800
cgcaacatta aaccagtacc agaggtgaaa atactcaata atttgggtgt ggacattgct   19860
gctaatactg tgatctggga ctacaaaaga gatgctccag cacatatatc tactattggt   19920
gtttgttcta tgactgacat agccaagaaa ccaactgaaa cgattgtgc accactcact   19980 gtcttttttg atggtagagt tgatggtcaa gtagacttat ttagaaatgc ccgtaatggt   20040
gttcttatta cagaaggtag tgttaaaggt ttacaaccat ctgtaggtcc caaacaagct   20100
agtcttaatg gagtcacatt aattggagaa gccgtaaaaa cacagttcaa ttattataag   20160
aaagttgatg gtgttgtcca acaattacct gaaacttact ttactcagag tagaaattta   20220
caagaattta aacccaggag tcaaatggaa attgatttct tagaattagc tatggatgaa   20280
ttcattgaac ggtataaatt agaaggctat gccttcgaac atatcgttta tggagatttt   20340
agtcatagtc agttaggtgg tttacatcta ctgattggac tagctaaacg tttttaaggaa   20400 tcacctttg aattagaaga ttttattcct atggacagta cagttaaaaa ctatttcata   20460
acagatgcgc aaacaggttc atctaagtgt gtgtgttctg ttattgattt attacttgat   20520
gattttgttg aaataataaa atcccaagat ttatctgtag tttctaaggt tgtcaaagtg   20580
```

-continued

```
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccccct gcatacacta attctttcac  21660
acgtggtgtt tattaccctg acaaagtttt cagatcctca gttttacatt caactcagga  21720
cttgttctta ccttcttttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata tgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca tcttgattc taaggttggt ggtaattata attacctgta  22920
tagattgttt aggaagtcta atctcaaacc ttttgagaga gatatttcaa ctgaaatcta  22980
```

```
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt aatagggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagttttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgattttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
```

-continued

```
ctgcaaattt gatgaagacg actctgagcc agtgctcaaa ggagtcaaat tacattacac    25380
ataaacgaac ttatggattt gtttatgaga atcttcacaa ttggaactgt aactttgaag    25440
caaggtgaaa tcaaggatgc tactccttca gattttgttc gcgctactgc aacgataccg    25500
atacaagcct cactcccttt cggatggctt attgttggcg ttgcacttct tgctgttttt    25560
cagagcgctt ccaaaatcat aaccctcaaa aagagatggc aactagcact ctccaagggt    25620
gttcactttg tttgcaactt gctgttgttg tttgtaacag tttactcaca ccttttgctc    25680
gttgctgctg gccttgaagc cccttttctc tatctttatg ctttagtcta cttcttgcag    25740
agtataaact ttgtaagaat aataatgagg ctttggcttt gctggaaatg ccgttccaaa    25800
aacccattac tttatgatgc caactatttt ctttgctggc atactaattg ttacgactat    25860
tgtatacctt acaatagtgt aacttcttca attgtcatta cttcaggtga tggcacaaca    25920
agtcctattt ctgaacatga ctaccagatt ggtggttata ctgaaaaatg ggaatctgga    25980
gtaaaagact gtgttgtatt acacagttac ttcacttcag actattacca gctgtactca    26040
actcaattga gtacagacac tggtgttgaa catgttacct tcttcatcta caataaaatt    26100
gttgatgagc ctgaagaaca tgtccaaatt cacacaatcg acggttcatc cggagttgtt    26160
aatccagtaa tggaaccaat ttatgatgaa ccgacgacga ctactagcgt gcctttgtaa    26220
gcacaagctg atgagtacga acttatgtac tcattcgttt cggaagagac aggtacgtta    26280
atagttaata gcgtacttct tttctcttgct ttcgtggtat tcttgctagt tacactagcc    26340
atccttactg cgcttcgatt gtgtgcgtac tgctgcaata ttgttaacgt gagtcttgta    26400
aaaccttctt tttacgttta ctctcgtgtt aaaaatctga attcttctag agttcctgat    26460
cttctggtct aaacgaacta aatattatat tagtttttct gtttggaact ttaattttag    26520
ccatggcaga ttccaacggt actattaccg ttgaagagct taaaaagctc cttgaacaat    26580
ggaacctagt aataggtttc ctattcctta catggatttg tcttctacaa tttgcctatg    26640
ccaacaggaa taggttttg tatataatta agttaatttt cctctggctg ttatggccag    26700
taactttagc ttgttttgtg cttgctgctg tttacagaat aaattggatc accggtggaa    26760
ttgctatcgc aatggcttgt cttgtaggct tgatgtggct cagctacttc attgcttctt    26820
tcagactgtt tgcgcgtacg cgttccatgt ggtcattcaa tccagaaact aacattcttc    26880
tcaacgtgcc actccatggc actattctga ccagaccgct tctagaaagt gaactcgtaa    26940
tcggagctgt gatccttcgt ggacatcttc gtattgctgg acaccatcta ggacgctgtg    27000
acatcaagga cctgcctaaa gaaatcactg ttgctacatc acgaacgctt tcttattaca    27060
aattgggagc ttcgcagcgt gtagcaggtg actcaggttt tgctgcatac agtcgctaca    27120
ggattggcaa ctataaatta aacacagacc attccagtag cagtgacaat attgctttgc    27180
ttgtacagta agtgacaaca gatgtttcat ctcgttgact ttcaggttac tatagcagag    27240
atattactaa ttattatgag gactttttaaa gtttccattt ggaatcttga ttacatcata    27300
aacctcataa ttaaaaattt atctaagtca ctaactgaga ataaatattc tcaattagat    27360
gaagagcaac caatggagat tgattaaacg aacatgaaaa ttattctttt cttggcactg    27420
ataacactcg ctacttgtga gctttatcac taccaagagt gtgttagagg tacaacagta    27480
cttttaaaag aaccttgctc ttctggaaca tacgagggca attcaccatt tcatcctcta    27540
gctgataaca aatttgcact gacttgcttt agcactcaat ttgcttttgc ttgtcctgac    27600
ggcgtaaaac acgtctatca gttacgtgcc agatcagttt cacctaaact gttcatcaga    27660
caagaggaag ttcaagaact ttactctcca atttttctta ttgttgcggc aatagtgttt    27720
```

-continued

```
ataacacttt gcttcacact caaaagaaag acagaatgat tgaactttca ttaattgact   27780
tctatttgtg ctttttagcc tttctgctat tccttgtttt aattatgctt attatctttt   27840
ggttctcact tgaactgcaa gatcataatg aaacttgtca cgcctaaacg aacatgaaat   27900
ttcttgtttt cttaggaatc atcacaactg tagctgcatt tcaccaagaa tgtagtttac   27960
agtcatgtac tcaacatcaa ccatatgtag ttgatgaccc gtgtcctatt cacttctatt   28020
ctaaatggta tattagagta ggagctagaa aatcagcacc tttaattgaa ttgtgcgtgg   28080
atgaggctgg ttctaaatca cccattcagt acatcgatat cggtaattat acagtttcct   28140
gtttaccttt tacaattaat tgccaggaac ctaaattggg tagtcttgta gtgcgttgtt   28200
cgttctatga agactttta gagtatcatg acgttcgtgt tgttttagat ttcatctaaa   28260
cgaacaaact aaaatgtctg ataatggacc ccaaaatcag cgaaatgcac cccgcattac   28320
gtttggtgga ccctcagatt caactggcag taaccagaat ggagaacgca gtggggcgcg   28380
atcaaaacaa cgtcggcccc aaggtttacc caataatact gcgtcttggt tcaccgctct   28440
cactcaacat ggcaaggaag accttaaatt ccctcgagga caaggcgttc caattaacac   28500
caatagcagt ccagatgacc aaattggcta ctaccgaaga gctaccagac gaattcgtgg   28560
tggtgacggt aaaatgaaag atctcagtcc aagatggtat ttctactacc taggaactgg   28620
gccagaagct ggacttccct atggtgctaa caaagacggc atcatatggg ttgcaactga   28680
gggagccttg aatacaccaa aagatcacat tggcacccgc aatcctgcta caatgctgc   28740 aatcgtgcta caacttcctc aaggaacaac attgccaaaa ggcttctacg cagaagggag   28800
cagaggcggc agtcaagcct cttctcgttc ctcatcacgt agtcgcaaca gttcaagaaa   28860
ttcaactcca ggcagcagta ggggaacttc tcctgctaga atggctggca atggcggtga   28920
tgctgctctt gctttgctgc tgcttgacag attgaaccag cttgagagca aaatgtctgg   28980
taaaggccaa caacaacaag gccaaactgt cactaagaaa tctgctgctg aggcttctaa   29040
gaagcctcgg caaaaacgta ctgccactaa agcatacaat gtaacacaag ctttcggcag   29100
acgtggtcca gaacaaaccc aaggaaattt tggggaccag gaactaatca gacaaggaac   29160
tgattacaaa cattggccgc aaattgcaca atttgccccc agcgcttcag cgttcttcgg   29220
aatgtcgcgc attggcatgg aagtcacacc ttcgggaacg tggttgacct acacaggtgc   29280
catcaaattg gatgacaaag atccaaattt caaagatcaa gtcattttgc tgaataagca   29340
tattgacgca tacaaaacat tcccaccaac agagcctaaa aaggacaaaa agaagaaggc   29400
tgatgaaact caagccttac cgcagagaca gaagaaacag caaactgtga ctcttcttcc   29460
tgctgcagat ttggatgatt ctccaaaca attgcaacaa tccatgagca gtgctgactc   29520
aactcaggcc taaactcatg cagaccacac aaggcagatg ggctatataa acgttttcgc   29580
ttttccgttt acgatatata gtctactctt gtgcagaatg aattctcgta actacatagc   29640
acaagtagat gtagttaact ttaatctcac atagcaatct ttaatcagtg tgtaacatta   29700
gggaggactt gaaagagcca ccacattttc accgaggcca cgcggagtac gatcgagtgt   29760
acagtgaaca atgctaggga gagctgccta tatggaagag ccctaatgtg taaaattaat   29820
tttagtagtg ctatccccat gtgattttaa tagcttctta ggagaatgac aaaaaaaaaa   29880
aaaaaaaaaa aaaaaaaaaa aaa                                           29903
```